US011312772B2

(12) United States Patent
Cemerski et al.

(10) Patent No.: US 11,312,772 B2
(45) Date of Patent: *Apr. 26, 2022

(54) COMBINATIONS OF PD-1 ANTAGONISTS AND BENZO [B] THIOPHENE STING AGONISTS FOR CANCER TREATMENT

(71) Applicants: Merck Sharp & Dohme Corp., Rahway, NJ (US); Saso Cemerski, Norfolk, MA (US); Jared N. Cumming, Winchester, MA (US); Johnny E. Kopinja, Newton, MA (US); Samanthi A. Perera, Lexington, MA (US); Benjamin Wesley Trotter, Medfield, MA (US); Archie Ngai-Chiu Tse, Long Island City, NY (US)

(72) Inventors: Saso Cemerski, Norfolk, MA (US); Jared N. Cumming, Winchester, MA (US); Johnny E. Kopinja, Newton, MA (US); Samanthi A. Perera, Lexington, MA (US); Benjamin Wesley Trotter, Medfield, MA (US); Archie Ngai-Chiu Tse, Long Island City, NY (US)

(73) Assignee: MERCK SHARP & DOHME CORP., Rahway, NJ (US)

( * ) Notice: Subject to any disclaimer, the term of this patent is extended or adjusted under 35 U.S.C. 154(b) by 23 days.

This patent is subject to a terminal disclaimer.

(21) Appl. No.: 16/635,059

(22) PCT Filed: Jul. 30, 2018

(86) PCT No.: PCT/US2018/044275
§ 371 (c)(1),
(2) Date: Jan. 29, 2020

(87) PCT Pub. No.: WO2019/027857
PCT Pub. Date: Feb. 7, 2019

(65) Prior Publication Data
US 2021/0130466 A1 May 6, 2021

Related U.S. Application Data

(60) Provisional application No. 62/541,180, filed on Aug. 4, 2017.

(51) Int. Cl.
*A61P 35/00* (2006.01)
*A61K 31/381* (2006.01)
*A61K 39/00* (2006.01)
*C07K 16/28* (2006.01)

(52) U.S. Cl.
CPC ........ *C07K 16/2818* (2013.01); *A61K 31/381* (2013.01); *A61P 35/00* (2018.01); *A61K 2039/505* (2013.01)

(58) Field of Classification Search
CPC .. A61K 31/381; A61K 2039/505; A61P 35/00
See application file for complete search history.

(56) References Cited

U.S. PATENT DOCUMENTS

| | | |
|---|---|---|
| 4,299,769 A | 11/1981 | McEvoy et al. |
| 4,342,689 A | 8/1982 | McEvoy et al. |
| 4,342,690 A | 8/1982 | McEvoy et al. |
| 4,342,691 A | 8/1982 | McEvoy et al. |
| 4,952,571 A | 8/1990 | Redpath et al. |
| 5,569,655 A | 10/1996 | Dority, Jr. et al. |
| 6,262,055 B1 | 7/2001 | Young et al. |
| 7,288,567 B2 | 10/2007 | Delorme et al. |
| 7,488,802 B2 | 2/2009 | Collins et al. |
| 7,521,051 B2 | 4/2009 | Collins et al. |
| 7,595,048 B2 | 9/2009 | Honjo et al. |
| 8,008,449 B2 | 8/2011 | Korman et al. |
| 8,168,757 B2 | 5/2012 | Finnefroch et al. |
| 8,354,509 B2 | 1/2013 | Carven et al. |
| 8,383,796 B2 | 2/2013 | Korman et al. |
| 8,664,255 B2 | 3/2014 | Freundlich et al. |
| 9,724,408 B2 | 8/2017 | Dubensky, Jr. et al. |
| 10,414,747 B2 | 9/2019 | Altman et al. |
| 10,703,738 B2 * | 7/2020 | Altman ............... C07D 333/60 |
| 10,730,849 B2 * | 8/2020 | Altman ............... C07D 498/04 |
| 2002/0115826 A1 | 8/2002 | Delorme et al. |

(Continued)

FOREIGN PATENT DOCUMENTS

| | | |
|---|---|---|
| EP | 0146243 | 6/1985 |
| EP | 0350990 A1 | 1/1990 |

(Continued)

OTHER PUBLICATIONS

Ablasser et al., Cell intrinsic immunity spreads to bystander cells via the intercellular transfer of cGAMP, Nature, Nov. 28, 2013, 530-546, 503.
Ablasser et al., cGAS produces a 2'-5'-linked cyclic dinucleotide second messenger that activates STING, Nature, Jun. 20, 2013, 380-385, 498.
Ausmees et al., Genetic Data Indicate that Proteins Containing the GGDEF Domain Possess Diguanylate Cyclase Activity, FEMS Microbiology, 2001, 163-167, Letters 204.
Berge, S.M., et al.,, "Pharmaceutical Salts", J. Pharm. Sci, 1977, pp. 1-19, vol. 66, No. 1.
Bookser et al., High-Throughput Five Minute Microwave Accelerated Glycosylation Approach to the Synthesis of Nucleoside Libraries, JOC Article, 2007, 173-179, 72.
Bruno et al., N-Substituted 2-aminobiphenylpalladium Methanesulfonate Precatalysts and Their Use in C—C and C—N Cross Couplings, The Journal of Organic Chamistry, 2014, 4161-4166, 79.

(Continued)

*Primary Examiner* — James D. Anderson
(74) *Attorney, Agent, or Firm* — Julie M. Lake; Catherine D. Fitch

(57) ABSTRACT

Therapeutic combinations that comprise at least one antagonist of the Programmed Death 1 receptor (PD-1) and at least one benzo[b]thiophene compound that activates the Stimulator of Interferon Genes (STING) pathway are disclosed herein. Also disclosed is the use of such therapeutic combinations for the treatment of cancers.

11 Claims, 9 Drawing Sheets

Specification includes a Sequence Listing.

(56) References Cited

U.S. PATENT DOCUMENTS

| | | |
|---|---|---|
| 2006/0040887 A1 | 2/2006 | Karaolls |
| 2008/0025979 A1 | 1/2008 | Honjo et al. |
| 2008/0286296 A1 | 11/2008 | Ebensen et al. |
| 2009/0181971 A1 | 7/2009 | Delorme et al. |
| 2010/0113477 A1 | 5/2010 | Freundlich et al. |
| 2011/0271358 A1 | 11/2011 | Freeman et al. |
| 2014/0017444 A1 | 1/2014 | Shimizu et al. |
| 2014/0206640 A1 | 7/2014 | Girijavallabhan et al. |
| 2014/0329889 A1 | 11/2014 | Vance et al. |
| 2014/0341976 A1 | 11/2014 | Dubensky, Jr. et al. |
| 2015/0056224 A1 | 2/2015 | Dubensky, Jr. et al. |
| 2015/0158886 A1 | 6/2015 | Jones et al. |
| 2016/0287698 A1 | 10/2016 | Yan et al. |
| 2016/0362441 A1 | 12/2016 | Vernejoul et al. |
| 2017/0050967 A1 | 2/2017 | Burai et al. |
| 2017/0146519 A1 | 5/2017 | DeFilippis et al. |
| 2017/0158724 A1* | 6/2017 | Adams ................ C07F 9/65746 |

FOREIGN PATENT DOCUMENTS

| | | |
|---|---|---|
| EP | 0350990 B1 | 9/1995 |
| EP | 3135290 A1 | 1/2018 |
| GB | 532822 | 1/1941 |
| RU | 2273476 C2 | 4/2006 |
| RU | 2540490 C2 | 2/2015 |
| WO | 1994008962 | 4/1994 |
| WO | 199962897 | 12/1999 |
| WO | 2001002369 A2 | 1/2001 |
| WO | 2001070675 | 9/2001 |
| WO | 2001087297 A1 | 11/2001 |
| WO | 2002010192 A2 | 2/2002 |
| WO | 2002068470 A2 | 9/2002 |
| WO | 2004004771 A1 | 1/2004 |
| WO | 2004056875 A1 | 7/2004 |
| WO | 2004072286 A1 | 8/2004 |
| WO | 2005020917 | 3/2005 |
| WO | 2007048088 A2 | 4/2007 |
| WO | 2008083174 A2 | 7/2008 |
| WO | 2010027827 A2 | 3/2010 |
| WO | 2010047774 | 4/2010 |
| WO | 2010077634 A1 | 7/2010 |
| WO | 2011066342 A2 | 6/2011 |
| WO | 2012068702 A1 | 5/2012 |
| WO | 2013019906 A1 | 2/2013 |
| WO | 2013185052 A1 | 12/2013 |
| WO | 2014093936 | 6/2014 |
| WO | 2014099824 | 6/2014 |
| WO | 2014099941 | 6/2014 |
| WO | 2014139388 A1 | 9/2014 |
| WO | 2014179335 | 11/2014 |
| WO | 2014179760 | 11/2014 |
| WO | 2014189805 A1 | 11/2014 |
| WO | 2014189806 | 11/2014 |
| WO | 2015017652 | 2/2015 |
| WO | 2015074145 A1 | 5/2015 |
| WO | 2015077354 A1 | 5/2015 |
| WO | 2015148746 A1 | 10/2015 |
| WO | 2015161137 A1 | 10/2015 |
| WO | 2015185565 | 12/2015 |
| WO | 2015189117 | 12/2015 |
| WO | 2016032927 A1 | 3/2016 |
| WO | 2016096174 | 6/2016 |
| WO | 2016096577 | 6/2016 |
| WO | 2016100261 | 6/2016 |
| WO | 2016120305 A1 | 8/2016 |
| WO | 2016145102 A1 | 9/2016 |
| WO | 2017011622 | 1/2017 |
| WO | 2017011920 | 1/2017 |
| WO | 2017019896 A1 | 2/2017 |
| WO | 2017027645 | 2/2017 |
| WO | 2017027646 A1 | 2/2017 |
| WO | 2017075477 A1 | 5/2017 |
| WO | 2017093933 A1 | 6/2017 |
| WO | 2017100305 | 6/2017 |
| WO | 2017106656 A1 | 6/2017 |
| WO | 2017123657 | 7/2017 |
| WO | 2017123669 | 7/2017 |
| WO | 2017161349 A1 | 9/2017 |
| WO | 2017175147 | 10/2017 |
| WO | 2017175156 | 10/2017 |
| WO | 2017216726 | 12/2017 |
| WO | 2018009466 | 1/2018 |
| WO | 2018067423 A1 | 4/2018 |

OTHER PUBLICATIONS

Burdette, Dara L., STING and the innate immune response to nucleic acids in the cytosol, Nature Immunology, Jan. 2013, 19-26, 14(1).

Burtner, et al., Synthetic Choleretics. I. Naphthol Derivatives, Journal of the American Chemical Society, 1951, 897-900, vol. 73.

Cagniant, et al., Condensed sulfur heterocycles. III. 1,2,3,4-Tetrahydrodibenzothiophene and, Bulletin de la Societe Chimique de France, 1952, 336-343.

Cagniant, et al., Condensed sulfur heterocycles. IV. Condensation of thianaphthene with glutaric anhydride and the, Bulletin de la Societe Chimique de France, 1952, 629-633, -.

Cagniant, et al., Condensed sulfur heterocycles. XIX. Synthesis of some ω-thionaphthenylalkanoic acids, Bulletin de la Societe Chimique de France, 1962, 576-581, -.

Child, et al., A New Non-steroidal Anti-Inflammatory Analgesic: γ-Oxo.(1,1'-biphenyl)-4-butanoic Acid (Fenbufen), Arzneimittel-Forschung, 1980, 695-702, vol. 30; Issue 4A.

Dande et al., Improving RNA Interference in Mammalian Cells by 4'-Thio-Modified Small Interfering RNA (siRNA): Effect on siRNA Activity and Nuclease Stability When Used in Combination with 2'-0-Alkyl Modifications, Journal of Medicinal Chemistry, 2006, 1624-1634, 49(5).

Diner et al., The Innate Immune DNA Sensor cGAS Produces a Noncanonical Cyclic Dinucleotide that Activates Human STING, 3 Cell Reports, Cell Reports, 2013, 1355-1361, 3.

Downey et al., DMXAA Causes Tumor Site-Specific Vascular Disruption in Murine Non-Small Molecule Lung Cancer, and Like the Endogenous Non-Canonical Cyclic Dinucleotide STING Agonist, 2'3'-cGAMP, Induces M2 Macrophage Repolarization, PLOS ONE, 2014, 1-14, 9-6-e99988.

English language translation of Markert, Jurgen et al., Darstellung von 1,2-Benzisothiazolen und einige Folgereaktionen, Liebigs Ann. Chem., 1980, 768-778, 5.

Ertem et al., Synthesis of RNA oligomers on heterogeneous templates, Nature, 1996, 238-240, 379-18.

Fagundes et al., Building unique bonds to fight misplaced DNA, Cell Research, 2013, 1065-1066, 2-9.

Fu, Juan, et al., Sting agonist formulated cancer vaccines can cure established tumors resistant to PD-1 blockade, Science Translational Medicine, 2015, 1-13, 7.

Gadthula et al., Synthesis and Anti-HIV Activity of β-D-3'-Azido-2',3'-unsaturated Nucleosides and β-D-3'-Azido-3'deoxyribofuranosylnucleosides, Nucleoside, Nucleotides, Nucleic Acids, 2005, 1707-1727, 24.

Gao et al., Cyclic [G(2',5')pA(3',5")p] Is the Metazoan Second Messenger Produced by DNA-Activated Cyclic GMP-AMP Synthase, CELL, 2013, 1094-1107, 153.

Gao et al., Structure-Function Ananlysis of STING Activation by c[G(2',5')pA(3',5')p] and Targeting by Antiviral DMXAA, Cell, 2013, 748-762, 154.

Goerlitzer, et al., 1,3-Dicarbonyl Compounds. XIV: 4-Oxo-4H-[1]benzofuro[3,2-b]pyrans, Archiv der Pharmazie, 1980, 385-398, vol. 313; Issue 5.

Gopinath et al., As many as six tandem reactions in one step! Unprecendented formation of highly functionalized benzothiophenes, Chemical Communication, Jul. 17, 2009, 7131-7133, vol. 46.

Gopinath, et al., Highly chemoselective Esterification Reactions and Boc/THP/TBDMS Discriminating Deprotections Under Samarium(III) Catalysis, Organic Letters, 2011, 1932-1935, vol. 13, Issue No. 8.

(56) References Cited

OTHER PUBLICATIONS

Gosselin et al., Systematic Synthesis and Biological Evaluation of 60 - and β-D-lyxofuranosyl Nucleosides of the Five Naturally Occurring Nucleic Acid Bases, J. Med. Chem, 1987, 982-991, 30.
Gould, Salt Selections for Basic Drugs, Intl. J. Pharmaceutics, 1986, pp. 201-217, vol. 33.
Hornfeldt, et al., Unsaturted γ-thiolactones II*. The Structures of 3-and 4-Methyl-2-thienols, Acta chem. Scand., 1962, 789-791, vol. 16; Issue No. 2.
Ikeuchi et al., Practical synthesis of natural plant-growth regulator 2-azahypoxanthine, its derivatives, and biotin-labeled probes, Organic & Biomolecular Chemistry, 2014, 3813, 12(23).
Joshi et al., Selectivity of montmorillonite catalyzed prebiotic reactions of D, L-nucleotides, Orig Life Evol Biosph, 2007, 3-26, 37-3.
Kim et al., A Convenient and Versatile Syntheses of 2' (and 3') amino (and azido)-2'(and 3') deoxyadenosine as Diverse Synthetic Precursors of Cyclic Adenosine Diphosphate Ribose (cADPR), Bull. Korean Chem. Soc., 2004, 243, 25-2.
Kobayashi et al., Bacterial c-di-GMP Affects Hematopoietic Stem/Progenitors and their Niches through STING, Cell Reports, 2015, 71-84, 11.
Kranzusch et al., Structure-Guided Reporgramming of Human cGAS Dinucleotide Linkage Specificity, Cell Inc., Elsevier Inc., 2014, 1011-1021, 158.
Kudo, et al., Synthesis of Monoamino and Monohydroxydibenzothiophenes, J. Heterocyclic Chem., 1985, 215218, vol. 22.
Li et al., Cyclic GMP-AMP Synthase is Activated by Double-Stranded DNA-lnduced Oligomerization, Immunity, 2013, 1019-1031, 39.
Li et al., Hydrolysis of 2'3'-cGAMP by ENPPI and Design of Nonhydrolyzable Analogs, 10 Nature Chemical Biology 1043 (Dec. 2014); Li et al., Hydrolysis of 2'3'-cGAMP by ENPPI and Design of Nonhydrolyzable Analogs ERRATUM, Nature Chemical Biology, 2014, 1043, 10.
Liu et al., Activated STING in a Vascular and Pulmonary Syndrome, The New England Journal of Medicine, 2015, 507, 371-6.
Liu et al., Hepatitis B Virus Polymerase Disrupts K63-Linked Ubiquitination of STING to Block Inate Cytosolic DNA-Sensing Pathways, Journal of Virology, 2015, 2287, 89-4.
Lolicato et al., Cyclic Dinucleotides Bind the C-Linker of HCN4 to Control Channel cGAMP Responsiveness, 10 Nature Chemical Biology 457 (Jun. 2014); Lolicato et al., Cyclic Dinucleotides Bind the C-Linker of HCN4 to Control Channel cGAMP Responsiveness, Nature Chemical Biology, 2014, 457, 10.
Markert, Jurgen et al., Darstellung von 1,2-Benzisothiazolen und einige Folgereaktionen, Liebigs Ann. Chem., 1980, 768-778, 5.
Mikhailov et al., Conformational Peculiarities of 5'-C-methylnucleosides, Bioorganicheskaya Khimiya, 1989, 969-975, 15(7).
Minakawa et al., Nucleosides and nucleotides. 116. Convenient syntheses of 3-deazaadenosine, 3-deazaguanosine, and 3-deazainosine via ring closure of 5-ethynyl-1-B-D-ribofuranosylimidazole-4-carboxamide or -carbonitrile. Tetrahedron, 1993, 557-570, 49(3).
O'Neill et al., Sensing the Dark Side of DNA, Sceince, 2013, 763, 339.
Ora et al., Hydrolytic reactions of cyclic bis(3'-5') diadenylic acid (c-di-AMP), J. Phys. Org. Chem, 2013, 218-225, 26.
Panne et al., Cytosolic DNA sensing unraveled, Nature Chemical Biology, 2013, 533, 9.
Patil et al., 4-aza-7,9-dideazaadenosine, a new cytotoxic synthetic C-nucleoside analogue of adenosine, Tetrahedron Letters, 1994, 5339-5342, 35(30).
PUBCHEM 23035231 deposited on Dec. 5, 2007 (Dec. 5, 2007), pp. 1-12. p. 4.
Puech et al., Synthesis of 9-(3-deoxy- and 2,3-dideoxy-3-fluoro-β-D-xylofuranosyl)guanines as potential antiviral agents, Tetrahedron Letters, 1989, 3171-3174, 30-24.
Ramesh et al., A convenient synthesis of 1-(β-D-ribofuranosyl)imidazo[4,5-d]pyridazin-4(5H)-one (2-aza-3-deazainosine) and its 2'-deoxy counterpart by ring closure of imidazole nucleosides, Journal of the Chemical Society, Perkin Transaction 1, 1989, 1769-1774, 10.
Roembke et al., A cyclic dinucleotide contianing 2-aminopurine is a general fluorescent sensor for c-di-GMP and 3'-3'-cGAMP, Molecular BioSystems, 2014, 1568-1575, 10.
Sali, et al., Characterization of a Novel Human-Specific STING Agonist that Elicits Antiviral Activity Against Emerging Alphaviruses, PLOS Pathogens, 2015, 1-30.
Sheridan, Cormac, Drug Developers Switch Gears to Inhibit STING, Nature Biotechnology, Mar. 4, 2019, 199-208, 37.
Simm et al., Phenotypic Convergence Mediated by GGDEF-Domain-Containing Proteins, Journal of Bacteriology, 2005, 6816-6823, 187(19).
Stahl et al., Aminoquinazoline Compounds as A2A Antagonist, Handbook of Pharmaceutical Salts Properties, Selection, and Use, 2002, 330-331.
Sun et al., Cyclic GMP-AMP Synthase Is a Cytosolic DNA Sensor That Activates the Type I Interferon Pathway, Science, 2013, 786, 339.
Tang et al., Single Amino Acid change in STING Leads to Constitutive Active Signaling, PLOS ONE, 2015, 1-10, (10)3.
Tosolini et al., Human Monocyte Recognition of Adenosine-Based Cyclic Dinucleotides Unveils the A2a G∞s Protein-Coupled Receptor Tonic Inhibition of Mitochondrially Induced Cell Death, Molecular and Cellular Biology, 2015, 479-495, 35-2.
Urata et al., Regio- and Diastereo-Selectivity of Montmorillonite-Catalyzed Oligomerization of Racemic Adenosine 5'-Phosphorimidazolide, Nucleosides, Nucleotides and Nucleic Acids, Nucleosides, Nucleotides and Nucleic Acids, 2008, 421-430, 27.
Wang et al., Synthesis and Biological Activity of 5-Fluorotubercidin, Nucleosides, Nucleotides and Nucleic Acids, 2004, 161-170, 23(1).
Wu et al., Cyclic GMP-AMP Is an Endogenous Second Messenger in Innate Immune Signaling by Cytosolic DNA, Science 826, 2013, 826-830, 339.
Zeng et al., MAVS, cGAS, and Endogenous Retroviruses in T-Independent B Cell Responses, Science, 2014, 1486-1492, 346-6216.
Zhang et al., Cyclic GMP-AMP Containing Mixed Phosphodiester Linkages Is An Endogenous High-Affinity Ligand for STING, Molecular Cell, 2013, 226-235, 51.
Zhou et al., The ER-Associated Protein ZDHHC1 Is a Positive Regulator of DNA Virus-Triggered, MITA/STING-Dependent Innate Immune Signaling, Cell Host & Microbe, 2014, 450-461, 16.
Belikov, V.G., Pharmaceutical Chemistry, Moscow MEDpress-inform, 2007, 27-29, 4th Edition.
Belikov, V.G, Pharmaceutical Chemistry, Moscow MEDpress-inform, 2007, 27-29, 4th Edition (English Translation).
Durnov, L.A. et al., Pediatric Oncology, Moscow, Medicine, 2002, 139, N/A.
Durnov, L.A. et al., Pediatric Oncology, Moscow, Medicine, 2002, 139, N/A (English Translation).
Dyson, G. and May, P., Chemistry of Synthetic Medicinal Substances, M: World, 1964, 12-19, N/A.
Dyson, G. and May, P., Chemistry of Synthetic Medicinal Substances, M: World, 1964, 12-19, N/A (English Translation).
Pokrovsky, V.I., Renal Stone Disease—Toxicomania, Small Medical Encyclopedia, Moscow, Meditcina, 1996, 90-96, 5.
Pokrovsky, V.I., Renal Stone Disease—Toxicomania, Small Medical Encyclopedia, Moscow, Meditcina, 1996, 90-96, 5 (English Translation).
Zakharova, N.M. et al., Physiologic Significance of Proliferative and Alterative Processes, Successes of Physiological Sciences, 2013, 33-53, 44(3).
Zakharova, N.M. et al., Physiologic Significance of Proliferative and Alterative Processes, Successes of Physiological Sciences, 2013, 33-53, 44(3) (English Translation).
Zhulenko, V.N. et al., Pharmacology, M.: KolosS, 2008, 34-35, N/A.
Zhulenko, V.N. et al., Pharmacology, M.: KolosS, 2008, 34-35, N/A (English Translation).
Bhattacharjee et al., Synthesis of heterocyclic steroids-III: An unsuccessful attempt at the Synthesis of B-Nor-6-thiaequilenin through 3-cyano-7-methoxy-4-oxo-1,2,3,4-Tetrahydrodibenzothiophene, Tetrahedron, 1960, 215-222, 10.

(56) References Cited

OTHER PUBLICATIONS

Burdette, Dara L., STING is a direct innate immune sensor of cyclic di-GMP, Nature, Oct. 27, 2011, 515-519, 178.
Internet source https://www.vidal.ru/drugs/leucovorin-teva-4924,published in Wayback Internet Archive Machine on Aug. 18, 2016, 2 pages.
Internet source https://www.vidal.ru/drugs/leucovorin-teva-4924, published in Wayback Internet Archive Machine on Aug. 18, 2016, 1 page.
Minakawa et al., Nucleosides and Nucleotides. 143. Synthesis of 5-Amino-4-imidazolecarboxamide (AICA) Deoxyribosides from Deoxyinosines and Their Conversion into 3-Deazapurine Derivatives, Chemical & Pharmaceutical Bulletin, 1996, 288-295, 44(2).
Mlochowski, et al., A Simple Route to Benzo[b]thiophenes: Sulfanylation-acylation of C-H Acids With 2-(Chlorosulfanyl)benzoyl Chloride, Phosphorus, Sulfur, and Silicon, 2009, 1115-1123, vol. 184; Issue 5.
Shi, Heping, et al., Molecular basis for the specific recognition of the metazoan cyclic GMP-AMP by the innate immune adaptor protein STING, PNAS, 2015, 8947-8952, vol. 112/No. 29.
Yi, Guanghui et al., Single Nucleotide Polymorphisms of Human STING Can Affect Innate Immune Response to Cyclic Dinucleotides, PLOS ONE, 2013, 1-16, 8-10-e77846.

\* cited by examiner

SEQ ID NO 1: Pembrolizumab, Variable Light chain, amino acid
Glu Ile Val Leu Thr Gln Ser Pro Ala Thr Leu Ser Leu Ser Pro Gly Glu Arg Ala Thr Leu Ser Cys
Arg Ala Ser Lys Gly Val Ser Thr Ser Gly Tyr Ser Tyr Leu His Trp Tyr Gln Gln Lys Pro Gly Gln
Ala Pro Arg Leu Leu Ile Tyr Leu Ala Ser Tyr Leu Glu Ser Gly Val Pro Ala Arg Phe Ser Gly Ser
Gly Ser Gly Thr Asp Phe Thr Leu Thr Ile Ser Ser Leu Glu Pro Glu Asp Phe Ala Val Tyr Tyr Cys
Gln His Ser Arg Asp Leu Pro Leu Thr Phe Gly Gly Gly Thr Lys Val Glu Ile Lys SEQ ID NO 2: Pembrolizumab, Variable Heavy chain, amino acid
Gln Val Gln Leu Val Gln Ser Gly Val Glu Val Lys Lys Pro Gly Ala Ser Val Lys Val Ser Cys
Lys Ala Ser Gly Tyr Thr Phe Thr Asn Tyr Tyr Met Tyr Trp Val Arg Gln Ala Pro Gly Gln Gly
Leu Glu Trp Met Gly Gly Ile Asn Pro Ser Asn Gly Gly Thr Asn Phe Asn Glu Lys Phe Lys Asn
Arg Val Thr Leu Thr Thr Asp Ser Ser Thr Thr Thr Ala Tyr Met Glu Leu Lys Ser Leu Gln Phe
Asp Asp Thr Ala Val Tyr Tyr Cys Ala Arg Arg Asp Tyr Arg Phe Asp Met Gly Phe Asp Tyr Trp
Gly Gln Gly Thr Thr Val Thr Val Ser Ser

FIG.1

SEQ ID NO 3: Pembrolizumab, Light chain, amino acid
Glu Ile Val Leu Thr Gln Ser Pro Ala Thr Leu Ser Leu Ser Pro Gly Glu Arg Ala Thr Leu Ser Cys
Arg Ala Ser Lys Gly Val Ser Thr Ser Gly Tyr Ser Tyr Leu His Trp Tyr Gln Gln Lys Pro Gly Gln
Ala Pro Arg Leu Leu Ile Tyr Leu Ala Ser Tyr Leu Glu Ser Gly Val Pro Ala Arg Phe Ser Gly Ser
Gly Ser Gly Thr Asp Phe Thr Leu Thr Ile Ser Ser Leu Glu Pro Glu Asp Phe Ala Val Tyr Tyr Cys
Gln His Ser Arg Asp Leu Pro Leu Thr Phe Gly Gly Gly Thr Lys Val Glu Ile Lys Arg Thr Val Ala
Ala Pro Ser Val Phe Ile Phe Pro Pro Ser Asp Glu Gln Leu Lys Ser Gly Thr Ala Ser Val Val Cys
Leu Leu Asn Asn Phe Tyr Pro Arg Glu Ala Lys Val Gln Trp Lys Val Asp Asn Ala Leu Gln Ser Gly
Asn Ser Gln Glu Ser Val Thr Glu Gln Asp Ser Lys Asp Ser Thr Tyr Ser Leu Ser Ser Thr Leu Thr
Leu Ser Lys Ala Asp Tyr Glu Lys His Lys Val Tyr Ala Cys Glu Val Thr His Gln Gly Leu Ser Ser
Pro Val Thr Lys Ser Phe Asn Arg Gly Glu Cys

FIG.2

SEQ ID NO 4: Pembrolizumab, Heavy chain, amino acid
Gln Val Gln Leu Val Gln Ser Gly Val Glu Val Lys Lys Pro Gly Ala Ser Val Lys Val Ser Cys
Lys Ala Ser Gly Tyr Thr Phe Thr Asn Tyr Tyr Met Tyr Trp Val Arg Gln Ala Pro Gly Gln Gly
Leu Glu Trp Met Gly Gly Ile Asn Pro Ser Asn Gly Gly Thr Asn Phe Asn Glu Lys Phe Lys Asn
Arg Val Thr Leu Thr Thr Asp Ser Ser Thr Thr Thr Ala Tyr Met Glu Leu Lys Ser Leu Gln Phe
Asp Asp Thr Ala Val Tyr Tyr Cys Ala Arg Arg Asp Tyr Arg Phe Asp Met Gly Phe Asp Tyr Trp
Gly Gln Gly Thr Thr Val Thr Val Ser Ser Ala Ser Thr Lys Gly Pro Ser Val Phe Pro Leu Ala
Pro Cys Ser Arg Ser Thr Ser Glu Ser Thr Ala Ala Leu Gly Cys Leu Val Lys Asp Tyr Phe Pro
Glu Pro Val Thr Val Ser Trp Asn Ser Gly Ala Leu Thr Ser Gly Val His Thr Phe Pro Ala Val
Leu Gln Ser Ser Gly Leu Tyr Ser Leu Ser Ser Val Val Thr Val Pro Ser Ser Ser Leu Gly Thr
Lys Thr Tyr Thr Cys Asn Val Asp His Lys Pro Ser Asn Thr Lys Val Asp Lys Arg Val Glu Ser
Lys Tyr Gly Pro Pro Cys Pro Pro Cys Pro Ala Pro Glu Phe Leu Gly Gly Pro Ser Val Phe Leu
Phe Pro Pro Lys Pro Lys Asp Thr Leu Met Ile Ser Arg Thr Pro Glu Val Thr Cys Val Val Val
Asp Val Ser Gln Glu Asp Pro Glu Val Gln Phe Asn Trp Tyr Val Asp Gly Val Glu Val His Asn
Ala Lys Thr Lys Pro Arg Glu Glu Gln Phe Asn Ser Thr Tyr Arg Val Val Ser Val Leu Thr Val
Leu His Gln Asp Trp Leu Asn Gly Lys Glu Tyr Lys Cys Lys Val Ser Asn Lys Gly Leu Pro Ser
Ser Ile Glu Lys Thr Ile Ser Lys Ala Lys Gly Gln Pro Arg Glu Pro Gln Val Tyr Thr Leu Pro
Pro Ser Gln Glu Glu Met Thr Lys Asn Gln Val Ser Leu Thr Cys Leu Val Lys Gly Phe Tyr Pro
Ser Asp Ile Ala Val Glu Trp Glu Ser Asn Gly Gln Pro Glu Asn Asn Tyr Lys Thr Thr Pro Pro
Val Leu Asp Ser Asp Gly Ser Phe Phe Leu Tyr Ser Arg Leu Thr Val Asp Lys Ser Arg Trp Gln
Glu Gly Asn Val Phe Ser Cys Ser Val Met His Glu Ala Leu His Asn His Tyr Thr Gln Lys Ser
Leu Ser Leu Ser Leu Gly Lys

FIG.3

SEQ ID NO 5: Pembrolizumab, CDRL1
Arg Ala Ser Lys Gly Val Ser Thr Ser Gly Tyr Ser Tyr Leu His SEQ ID NO 6: Pembrolizumab, CDRL2
Leu Ala Ser Tyr Leu Glu Ser SEQ ID NO 7: Pembrolizumab, CDRL3
Gln His Ser Arg Asp Leu Pro Leu Thr SEQ ID NO 8: Pembrolizumab, CDRH1
Asn Tyr Tyr Met Tyr SEQ ID NO 9: Pembrolizumab, CDRH2
Gly Ile Asn Pro Ser Asn Gly Gly Thr Asn Phe Asn Glu Lys Phe Lys SEQ ID NO 10: Pembrolizumab, CDRH3
Arg Asp Tyr Arg Phe Asp Met Gly Phe Asp Tyr

FIG.4

SEQ ID NO 11: Nivolumab, Variable Light chain, amino acid
Glu Ile Val Leu Thr Gln Ser Pro Ala Thr Leu Ser Leu Ser Pro Gly Glu Arg Ala Thr Leu Ser Cys
Arg Ala Ser Gln Ser Val Ser Ser Tyr Leu Ala Trp Tyr Gln Gln Lys Pro Gly Gln Ala Pro Arg Leu
Leu Ile Tyr Asp Ala Ser Asn Arg Ala Thr Gly Ile Pro Ala Arg Phe Ser Gly Ser Gly Ser Gly Thr
Asp Phe Thr Leu Thr Ile Ser Ser Leu Glu Pro Glu Asp Phe Ala Val Tyr Tyr Cys Gln Gln Ser Ser
Asn Trp Pro Arg Thr Phe Gly Gln Gly Thr Lys Val Glu Ile Lys SEQ ID NO 12: Nivolumab, Variable Heavy chain, amino acid
Gln Val Gln Leu Val Glu Ser Gly Gly Gly Val Val Gln Pro Gly Arg Ser Leu Arg Leu Asp Cys Lys
Ala Ser Gly Ile Thr Phe Ser Asn Ser Gly Met His Trp Val Arg Gln Ala Pro Gly Lys Gly Leu Glu
Trp Val Ala Val Ile Trp Tyr Asp Gly Ser Lys Arg Tyr Tyr Ala Asp Ser Val Lys Gly Arg Phe Thr
Ile Ser Arg Asp Asn Ser Lys Asn Thr Leu Phe Leu Gln Met Asn Ser Leu Arg Ala Glu Asp Thr Ala
Val Tyr Tyr Cys Ala Thr Asn Asp Asp Tyr Trp Gly Gln Gly Thr Leu Val Thr Val Ser Ser

FIG.5

SEQ ID NO 13: Nivolumab, Light chain, amino acid
Glu Ile Val Leu Thr Gln Ser Pro Ala Thr Leu Ser Leu Ser Pro Gly Glu Arg Ala Thr Leu Ser Cys
Arg Ala Ser Gln Ser Val Ser Ser Tyr Leu Ala Trp Tyr Gln Gln Lys Pro Gly Gln Ala Pro Arg Leu
Leu Ile Tyr Asp Ala Ser Asn Arg Ala Thr Gly Ile Pro Ala Arg Phe Ser Gly Ser Gly Ser Gly Thr
Asp Phe Thr Leu Thr Ile Ser Ser Leu Glu Pro Glu Asp Phe Ala Val Tyr Tyr Cys Gln Gln Ser Ser
Asn Trp Pro Arg Thr Phe Gly Gln Gly Thr Lys Val Glu Ile Lys Arg Thr Val Ala Ala Pro Ser Val
Phe Ile Phe Pro Pro Ser Asp Glu Gln Leu Lys Ser Gly Thr Ala Ser Val Val Cys Leu Leu Asn Asn
Phe Tyr Pro Arg Glu Ala Lys Val Gln Trp Lys Val Asp Asn Ala Leu Gln Ser Gly Asn Ser Gln Glu
Ser Val Thr Glu Gln Asp Ser Lys Asp Ser Thr Tyr Ser Leu Ser Ser Thr Leu Thr Leu Ser Lys Ala
Asp Tyr Glu Lys His Lys Val Tyr Ala Cys Glu Val Thr His Gln Gly Leu Ser Ser Pro Val Thr Lys
Ser Phe Asn Arg Gly Glu Cys

SEQ ID NO 14: Nivolumab, Heavy chain, amino acid
Gln Val Gln Leu Val Glu Ser Gly Gly Val Val Gln Pro Gly Arg Ser Leu Arg Leu Asp Cys Lys
Ala Ser Gly Ile Thr Phe Ser Asn Ser Gly Met His Trp Val Arg Gln Ala Pro Gly Lys Gly Leu Glu
Trp Val Ala Val Ile Trp Tyr Asp Gly Ser Lys Arg Tyr Tyr Ala Asp Ser Val Lys Gly Arg Phe Thr
Ile Ser Arg Asp Asn Ser Lys Asn Thr Leu Phe Leu Gln Met Asn Ser Leu Arg Ala Glu Asp Thr Ala
Val Tyr Tyr Cys Ala Thr Asn Asp Asp Tyr Trp Gly Gln Gly Thr Leu Val Thr Val Ser Ser Ala Ser
Thr Lys Gly Pro Ser Val Phe Pro Leu Ala Pro Cys Ser Arg Ser Thr Ser Glu Ser Thr Ala Ala Leu
Gly Cys Leu Val Lys Asp Tyr Phe Pro Glu Pro Val Thr Val Ser Trp Asn Ser Gly Ala Leu Thr Ser
Gly Val His Thr Phe Pro Ala Val Leu Gln Ser Ser Gly Leu Tyr Ser Leu Ser Ser Val Val Thr Val
Pro Ser Ser Leu Gly Thr Lys Thr Tyr Thr Cys Asn Val Asp His Lys Pro Ser Asn Thr Lys Val
Asp Lys Arg Val Glu Ser Lys Tyr Gly Pro Pro Cys Pro Pro Cys Pro Ala Pro Glu Phe Leu Gly Gly
Pro Ser Val Phe Leu Phe Pro Pro Lys Pro Lys Asp Thr Leu Met Ile Ser Arg Thr Pro Glu Val Thr
Cys Val Val Val Asp Val Ser Gln Glu Asp Pro Glu Val Gln Phe Asn Trp Tyr Val Asp Gly Val Glu
Val His Asn Ala Lys Thr Lys Pro Arg Glu Glu Gln Phe Asn Ser Thr Tyr Arg Val Val Ser Val Leu
Thr Val Leu His Gln Asp Trp Leu Asn Gly Lys Glu Tyr Lys Cys Lys Val Ser Asn Lys Gly Leu Pro
Ser Ser Ile Glu Lys Thr Ile Ser Lys Ala Lys Gly Gln Pro Arg Glu Pro Gln Val Tyr Thr Leu Pro
Pro Ser Gln Glu Glu Met Thr Lys Asn Gln Val Ser Leu Thr Cys Leu Val Lys Gly Phe Tyr Pro Ser
Asp Ile Ala Val Glu Trp Glu Ser Asn Gly Gln Pro Glu Asn Asn Tyr Lys Thr Thr Pro Pro Val Leu
Asp Ser Asp Gly Ser Phe Phe Leu Tyr Ser Arg Leu Thr Val Asp Lys Ser Arg Trp Gln Glu Gly Asn
Val Phe Ser Cys Ser Val Met His Glu Ala Leu His Asn His Tyr Thr Gln Lys Ser Leu Ser Leu Ser
Leu Gly Lys SEQ ID NO 15: Nivolumab, CDRL1
Arg Ala Ser Gln Ser Val Ser Ser Tyr Leu Ala SEQ ID NO 16: Nivolumab, CDRL2
Asp Ala Ser Asn Arg Ala Thr SEQ ID NO 17: Nivolumab, CDRL3
Gln Gln Ser Ser Asn Trp Pro Arg Thr SEQ ID NO 18: Nivolumab, CDRH1
Asn Ser Gly Met His SEQ ID NO 19: Nivolumab, CDRH2
Val Ile Trp Tyr Asp Gly Ser Lys Arg Tyr Tyr Ala Asp Ser Val Lys Gly SEQ ID NO 20: Nivolumab, CDRH3
Asn Asp Asp Tyr

FIG.8

SEQ ID NO 21: Human PD-L1
Met Arg Ile Phe Ala Val Phe Ile Phe Met Thr Tyr Trp His Leu Leu Asn Ala Phe Thr Val
Pro Lys Asp Leu Tyr Val Val Glu Tyr Gly Ser Asn Met Thr Ile Glu Cys Lys Phe Pro Val Lys
Gln Leu Asp Leu Ala Ala Leu Ile Val Tyr Trp Glu Met Glu Asp Lys Asn Ile Ile Gln Phe Val His
Gly Glu Glu Asp Leu Lys Val Gln His Ser Ser Tyr Arg Gln Arg Ala Arg Leu Leu Lys Asp Gln Leu
Ser Leu Gly Asn Ala Ala Leu Gln Ile Thr Asp Val Lys Leu Gln Asp Ala Gly Val Tyr Arg Cys Met
Ile Ser Tyr Gly Gly Ala Asp Tyr Lys Arg Ile Thr Val Lys Val Asn Ala Pro Tyr Asn Lys Ile Asn
Gln Arg Ile Leu Val Val Asp Pro Val Thr Ser Glu His Glu Leu Thr Cys Gln Ala Glu Gly Tyr Pro
Lys Ala Glu Val Ile Trp Thr Ser Ser Asp His Gln Val Leu Ser Gly Lys Thr Thr Thr Asn Ser
Lys Arg Glu Glu Lys Leu Phe Asn Val Thr Ser Thr Leu Arg Ile Asn Thr Thr Thr Asn Glu Ile Phe
Tyr Cys Thr Phe Arg Arg Leu Asp Pro Glu Glu Asn His Thr Ala Glu Leu Val Ile Pro Glu Leu Pro
Leu Ala His Pro Pro Asn Glu Arg Thr His Leu Val Ile Leu Gly Ala Ile Leu Leu Cys Leu Gly Val
Ala Leu Thr Phe Ile Phe Arg Leu Arg Lys Gly Arg Met Met Asp Val Lys Lys Cys Gly Ile Gln Asp
Thr Asn Ser Lys Lys Gln Ser Asp Thr His Leu Glu Glu Thr

FIG.9

COMBINATIONS OF PD-1 ANTAGONISTS AND BENZO [B] THIOPHENE STING AGONISTS FOR CANCER TREATMENT

CROSS-REFERENCE TO RELATED APPLICATIONS

This application is a National Stage application of International Patent Application No. PCT/US2018/044275, filed Jul. 30, 2018, which claims priority to U.S. Provisional Patent Application No. 62/541,180, filed Aug. 4, 2017.

FIELD OF THE INVENTION

The present disclosure relates to combinations of therapeutic compounds that are useful to treat cancer. In particular, this disclosure relates to combination therapies comprising at least one antagonist of a Programmed Death 1 protein (PD-1) and at least one benzo[b]thiophene compounds that is useful as a STING (Stimulator of Interferon Genes) agonist and activates the STING pathway.

REFERENCE TO SEQUENCE LISTING SUBMITTED ELECTRONICALLY

The sequence listing of the present application is submitted electronically via EFS-Web as an ASCII-formatted sequence listing, with a file name of "24492W0PCT-SEQLIST-29JUNE2018", a creation date of Jun. 29, 2018, and a size of 21 KB. This sequence listing submitted via EFS-Web is part of the specification and is herein incorporated by reference in its entirety.

BACKGROUND OF THE INVENTION

The cytotoxic T-lymphocyte-associated antigen 4 (CLTA-4) and PD-1 pathways are important negative regulators of immune response. Activated T-cells up-regulate CTLA-4, which binds on antigen-presenting cells and inhibits T-cell stimulation, IL-2 gene expression, and T-cell proliferation. These anti-tumor effects have been observed in mouse models of colon carcinoma, metastatic prostate cancer, and metastatic melanoma. PD-1 binds to active T-cells and suppresses T-cell activation. PD-1 antagonists have demonstrated anti-tumor effects as well. PD-1 is moderately expressed on naïve T-, B- and natural killer (NK) T-cells and is upregulated by T/B cell receptor signaling on lymphocytes, monocytes, and myeloid cells.

Two known ligands for PD-1, PD-L1 (B7-H1) and PD-L2 (B7-DC), are expressed in human cancers that arise in various tissues. In large sample sets of, for example, ovarian, renal, colorectal, pancreatic, and liver cancers, and of melanoma, it was shown that PD-L1 expression correlated with poor prognosis and reduced overall patient survival irrespective of subsequent treatment. Similarly, PD-1 expression on tumor infiltrating lymphocytes was found to mark dysfunctional T-cells in breast cancer and melanoma and to correlate with poor prognosis in renal cancer patients. Thus, it has been proposed that PD-L1 expressing tumor cells interact with PD-1 expressing T-cells to attenuate T-cell activation and evasion of immune surveillance, thereby contributing to an impaired immune response against the tumor.

Several monoclonal antibodies that inhibit the interaction between PD-1 and one or both of its ligands PD-L1 and PD-L2 are in clinical development for treating cancer. It has been proposed that the efficacy of such antibodies might be enhanced if administered in combination with other approved or experimental cancer therapies, e.g., radiation, surgery, chemotherapeutic agents, targeted therapies, agents that inhibit other signaling pathways that are disregulated in tumors, and other immune enhancing agents. See Morrissey et al., Clinical and Translational Science 9(2): 89-104 (2016).

Another potential immune therapy for cancers and for other cell-proliferation disorders is related to the immune system response to certain danger signals associated with cellular or tissue damage. The innate immune system has no antigen specificity but does respond to a variety of effector mechanisms, such as the damage-associated molecular patterns (DAMPs) or pathogen-associated molecular patterns (PAMPs), such as those associated with opsonization, phagocytosis, activation of the complement system, and production of soluble bioactive molecules such as cytokines or chemokines. These are all mechanisms by which the innate immune system mediates its response. In this way, the innate immune system is able to provide broad protection against a wide range of threats to the host.

Free cytosolic DNA and RNA are among these PAMPs and DAMPs. It has recently been demonstrated that the main sensor for cytosolic DNA is cGAS (cyclic GMP-AMP synthase). Upon recognition of cytosolic DNA, cGAS catalyzes the generation of the cyclic-dinucleotide 2'-3' cGAMP, an atypical second messenger that strongly binds to the ER-transmembrane adaptor protein STING. A conformational change is undergone by cGAMP-bound STING, which translocates to a perinuclear compartment and induces the activation of critical transcription factors IRF-3 and NF-κB. This leads to a strong induction of type I interferons and production of pro-inflammatory cytokines such as IL-6, TNF-α and IFN-γ.

The importance of type I interferons and pro-inflammatory cytokines on various cells of the immune system has been very well established. In particular, these molecules strongly potentiate T-cell activation by enhancing the ability of dendritic cells and macrophages to uptake, process, present and cross-present antigens to T-cells. The T-cell stimulatory capacity of these antigen-presenting cells is augmented by the up-regulation of critical co-stimulatory molecules, such as CD80 or CD86. Finally, type I interferons can rapidly engage their cognate receptors and trigger the activation of interferon-responsive genes that can significantly contribute to adaptive immune cell activation.

From a therapeutic perspective, interferons, and compounds that can induce interferon production, have potential use in the treatment of human cancers. Such molecules are potentially useful as anti-cancer agents with multiple pathways of activity. Interferons can inhibit human tumor cell-proliferation directly and may be synergistic with various approved chemotherapeutic agents. Type I interferons can significantly enhance anti-tumor immune responses by inducing activation of both the adaptive and innate immune cells. Finally, tumor invasiveness may be inhibited by interferons by modulating enzyme expression related to tissue remodeling.

In view of the potential of type I interferons and type I interferon-inducing compounds as anti-viral and anti-cancer agents, there remains a need for new agents that can induce potent type I interferon production. With the growing body of data demonstrating that the cGAS-STING cytosolic DNA sensory pathway has a significant capacity to induce type I interferons, STING activating agents are rapidly taking an important place in today's anti-tumor therapy landscape.

SUMMARY OF THE INVENTION

Embodiments of the disclosure include combination therapies, or therapeutic combinations, comprising at least one PD-1 antagonist and at least one benzo[b]thiophene STING agonist.

Another embodiment includes a method of treating a cell-proliferation disorder in a subject in need thereof, comprising administering a combination therapy comprising at least one PD-1 antagonist and at least one benzo[b]thiophene STING agonist.

Other embodiments, aspects and features of the present invention are either further described in or will be apparent from the ensuing description, examples and appended claims.

BRIEF DESCRIPTION OF THE DRAWINGS

FIG. 1 shows the amino acid sequences of the light chain and heavy chain variable regions for pembrolizumab that may be used in the combinations disclosed herein.

FIG. 2 shows the amino acid sequence of the light chain for pembrolizumab.

FIG. 3 shows the amino acid sequence of the heavy chain for pembrolizumab.

FIG. 4 shows the amino acid sequences of the CDRs 1, 2, and 3 of the light chain variable region (CDRL1, CDRL2, and CDRL3) and of the CDRs 1, 2, and 3 of the heavy chain variable region (CDRH1, CDRH2, and CDRH3) for pembrolizumab.

FIG. 5 shows the amino acid sequences of the light chain and heavy chain variable regions for nivolumab that may be used in the combinations disclosed herein.

FIG. 6 shows the amino acid sequence of the light chain for nivolumab.

FIG. 7 shows the amino acid sequence of the heavy chain for nivolumab.

FIG. 8 shows the amino acid sequences of the CDRs 1, 2, and 3 of the light chain variable region (CDRL1, CDRL2, and CDRL3) and of the CDRs 1, 2, and 3 of the heavy chain variable region (CDRH1, CDRH2, and CDRH3) nivolumab.

FIG. 9 shows the amino acid sequence for the human PD-L1 molecule (amino acids 19-290).

DETAILED DESCRIPTION OF THE INVENTION

Abbreviations

μg, ug Microgram
Anti-PD-1 Antagonist of a Programmed Death 1 protein
BID One dose twice daily
C57Bl/6 Common inbred strain of laboratory mouse, also "C57 black 6", "C57", "black 6", or "B6"
CDR Complementary determining region
CR Complete regression
Ctrl Control
DFS Disease free survival
DLT Dose limiting toxicity
FFPE Formalin-fixed, paraffin-embedded
FR Framework region
IgG Immunoglobulin G
IgG1 Immunoglobulin G subclass 1
IHC Immunohistochemistry or immunohistochemical
IP Intraperitoneal
IT Intratumoral
kg Kilogram
mAb Monoclonal antibody
MC38 Murine Carcinoma-38 Mouse colon adenocarcinoma cell line
mg Milligram
mIgG1 Murine immunoglobulin G subclass 1, Isotype control mAb for anti-PD-1 antibody muDX400
mL Milliliter
mm Millimeter
$mm^3$ Cubic millimeter, 0.001 mL
MPK Milligram per kilogram
MTD Maximum tolerated dose
n Number of subjects in a treatment group
NCI National Cancer Institute
OR Overall response
OS Overall survival
PBS Phosphate-buffered saline, vehicle control for benzo[b]thiophene STING agonists
PD-1 Programmed cell death protein 1
PFS Progression free survival
PR Partial response
p-values Calculated probability
QD One dose per day
RECIST Response Evaluation Criteria in Solid Tumors
SD Stable disease
SEM Standard error of the mean
TGI Tumor growth inhibition
T/C Median tumor volume of the treated animal/Median tumor volume of the control animal Additional abbreviations may be defined throughout this disclosure.

Definitions

Certain technical and scientific terms are specifically defined below. Unless specifically defined elsewhere in this document, all other technical and scientific terms used herein have the meaning commonly understood by one of ordinary skill in the art to which this disclosure relates.

"About" when used to modify a numerically defined parameter (e.g., the dose of a PD-1 antagonist or benzo[b]thiophene STING agonist, or the length of treatment time with a combination therapy described herein) means that the parameter may vary by as much as 10% below or above the stated numerical value for that parameter; where appropriate, the stated parameter may be rounded to the nearest whole number. For example, a dose of about 5 mg/kg may vary between 4.5 mg/kg and 5.5 mg/kg.

As used herein, including the appended claims, the singular forms of words such as "a," "an," and "the," include their corresponding plural references unless the context clearly dictates otherwise.

The terms "administration of" and or "administering" a compound should be understood to include providing a compound described herein, or a pharmaceutically acceptable salt thereof, and compositions of the foregoing to a subject.

As used herein, the term "antibody" refers to any form of immunoglobulin molecule that exhibits the desired biological or binding activity. Thus, it is used in the broadest sense and specifically covers, but is not limited to, monoclonal antibodies (including full length monoclonal antibodies), polyclonal antibodies, multispecific antibodies (e.g., bispecific antibodies), humanized, fully human antibodies, chimeric antibodies, and camelized single domain antibodies. "Parental antibodies" are antibodies obtained by exposure of an immune system to an antigen prior to modification of the antibodies for an intended use, such as humanization of an antibody for use as a human therapeutic. As used herein, the term "antibody" encompasses not only intact polyclonal or monoclonal antibodies, but also, unless otherwise specified, any antigen binding portion thereof that competes with the intact antibody for specific binding, fusion proteins comprising an antigen binding portion, and any other modified configuration of the immunoglobulin molecule that comprises an antigen recognition site.

As used herein, unless otherwise indicated, "antibody fragment" or "antigen binding fragment" refers to a fragment of an antibody that retains the ability to bind specifically to the antigen, e.g. fragments that retain one or more CDR regions. An antibody that "specifically binds to" PD-1 or PD-L1 is an antibody that exhibits preferential binding to PD-1 or PD-L1 (as appropriate) as compared to other proteins, but this specificity does not require absolute binding specificity. An antibody is considered "specific" for its intended target if its binding is determinative of the presence of the target protein in a sample, e.g. without producing undesired results such as false positives. Antibodies, or binding fragments thereof, will bind to the target protein with an affinity that is at least two fold greater, preferably at least ten times greater, more preferably at least 20-times greater, and most preferably at least 100-times greater than the affinity with non-target proteins.

Antigen binding portions include, for example, Fab, Fab', F(ab')2, Fd, Fv, domain antibodies (dAbs, e.g., shark and camelid antibodies), fragments including complementarity determining regions (CDRs), single chain variable fragment antibodies (scFv), maxibodies, minibodies, intrabodies, diabodies, triabodies, tetrabodies, v-NAR, and bis-scFv, and polypeptides that contain at least a portion of an immunoglobulin that is sufficient to confer specific antigen binding to the PD-1 or PD-L1. An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1, and IgA2. The heavy-chain constant regions that correspond to the different classes of immunoglobulins are called alpha, delta, epsilon, gamma, and mu, respectively. The subunit structures and three-dimensional configurations of different classes of immunoglobulins are well known.

As used herein, the terms "at least one" item or "one or more" item each include a single item selected from the list as well as mixtures of two or more items selected from the list.

As used herein, the term "immune response" relates to any one or more of the following: specific immune response, non-specific immune response, both specific and non-specific response, innate response, primary immune response, adaptive immunity, secondary immune response, memory immune response, immune cell activation, immune cell-proliferation, immune cell differentiation, and cytokine expression.

The term "pharmaceutically acceptable carrier" refers to any inactive substance that is suitable for use in a formulation for the delivery of a therapeutic agent. A carrier may be an antiadherent, binder, coating, disintegrant, filler or diluent, preservative (such as antioxidant, antibacterial, or antifungal agent), sweetener, absorption delaying agent, wetting agent, emulsifying agent, buffer, and the like. Examples of suitable pharmaceutically acceptable carriers include water, ethanol, polyols (such as glycerol, propylene glycol, polyethylene glycol, and the like), dextrose, vegetable oils (such as olive oil), saline, buffer, buffered saline, and isotonic agents such as sugars, polyalcohols, sorbitol, and sodium chloride.

The term "subject" (alternatively "patient") as used herein refers to a mammal that has been the object of treatment, observation, or experiment. The mammal may be male or female. The mammal may be one or more selected from the group consisting of humans, bovine (e.g., cows), porcine (e.g., pigs), ovine (e.g., sheep), capra (e.g., goats), equine (e.g., horses), canine (e.g., domestic dogs), feline (e.g., house cats), Lagomorpha (rabbits), rodents (e.g., rats or mice), *Procyon lotor* (e.g., raccoons). In particular embodiments, the subject is human.

The term "subject in need thereof" as used herein refers to a subject diagnosed with, or suspected of having, a cell-proliferation disorder, such as a cancer, as defined herein.

As used herein, the terms "treatment" and "treating" refer to all processes in which there may be a slowing, interrupting, arresting, controlling, or stopping of the progression of a disease or disorder described herein. The terms do not necessarily indicate a total elimination of all disease or disorder symptoms.

"Variable regions" or "V region" or "V chain" as used herein means the segment of IgG chains which is variable in sequence between different antibodies. A "variable region" of an antibody refers to the variable region of the antibody light chain or the variable region of the antibody heavy chain, either alone or in combination. Typically, the variable regions of both the heavy and light chains comprise three hypervariable regions, also called complementarity determining regions (CDRs), which are located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3, CDR3, and FR4. The assignment of amino acids to each domain is, generally, in accordance with the definitions of Sequences of Proteins of Immunological Interest, Kabat, et al.; National Institutes of Health, Bethesda, Md.; 5th ed.; NIH Publ. No. 91-3242 (1991); Kabat (1978) Adv. Prot. Chem. 32:1-75; Kabat, et al., (1977) J. Biol. Chem. 252:6609-6616; Chothia, et al., (1987) J Mol. Biol. 196:901-917 or Chothia, et al., (1989) Nature 342: 878-883.

"Chimeric antibody" refers to an antibody in which a portion of the heavy and/or light chain contains sequences derived from a particular species (e.g., human) or belonging to a particular antibody class or subclass, while the remainder of the chain(s) is derived from another species (e.g., mouse) or belonging to another antibody class or subclass, as well as fragments of such antibodies, so long as they exhibit the desired biological activity.

"Human antibody" refers to an antibody that comprises human immunoglobulin protein sequences or derivatives thereof. A human antibody may contain murine carbohydrate chains if produced in a mouse, in a mouse cell, or in a hybridoma derived from a mouse cell. Similarly, "mouse antibody" or "rat antibody" refer to an antibody that comprises only mouse or rat immunoglobulin sequences or derivatives thereof, respectively.

"Humanized antibody" refers to forms of antibodies that contain sequences from non-human (e.g., murine) antibodies as well as human antibodies. Such antibodies contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. The prefix "hum", "hu" or "h" may be added to antibody clone designations when necessary to distinguish humanized antibodies from parental rodent antibodies. The humanized forms of rodent antibodies will generally comprise the same CDR sequences of the parental rodent antibodies, although certain amino acid substitutions may be included to increase affinity, increase stability of the humanized antibody, or for other reasons.

"Biotherapeutic agent" means a biological molecule, such as an antibody or fusion protein, that blocks ligand/receptor signaling in any biological pathway that supports tumor maintenance and/or growth or suppresses the anti-tumor immune response.

"Chemotherapeutic agent" refers to a chemical or biological substance that can cause death of cancer cells, or interfere with growth, division, repair, and/or function of cancer cells. Examples of chemotherapeutic agents include those that are disclosed in WO2006/129163, and US20060153808, the disclosures of which are incorporated herein by reference. Classes of chemotherapeutic agents include, but are not limited to: alkylating agents, antimetabolites, kinase inhibitors, spindle poison, plant alkaloids, cytoxic/antitumor antibiotics, topisomerase inhibitors, photosensitizers, anti-estrogens and selective estrogen receptor modulators (SERMs), anti-progesterones, estrogen receptor down-regulators (ERDs), estrogen receptor antagonists, leutinizing hormone-releasing hormone agonists, anti-androgens, aromatase inhibitors, EGFR inhibitors, VEGF inhibitors, and anti-sense oligonucleotides that inhibit expression of genes implicated in abnormal cell-proliferation or tumor growth. Chemotherapeutic agents useful in the treatment methods of the present disclosure include cytostatic and/or cytotoxic agents.

The therapeutic agents and compositions provided by the present disclosure can be administered via any suitable enteral route or parenteral route of administration. The term "enteral route" of administration refers to the administration via any part of the gastrointestinal tract. Examples of enteral routes include oral, mucosal, buccal, and rectal route, or intragastric route. "Parenteral route" of administration refers to a route of administration other than enteral route. Examples of parenteral routes of administration include intravenous, intramuscular, intradermal, intraperitoneal, intratumor, intravesical, intraarterial, intrathecal, intracapsular, intraorbital, intracardiac, transtracheal, intraarticular, subcapsular, subarachnoid, intraspinal, epidural and intrasternal, subcutaneous, or topical administration. The therapeutic agents and compositions of the disclosure can be administered using any suitable method, such as by oral ingestion, nasogastric tube, gastrostomy tube, injection, infusion, implantable infusion pump, and osmotic pump. The suitable route and method of administration may vary depending on a number of factors such as the specific antibody being used, the rate of absorption desired, specific formulation or dosage form used, type or severity of the disorder being treated, the specific site of action, and conditions of the patient, and can be readily selected by a person skilled in the art.

The term "simultaneous administration" as used herein in relation to the administration of medicaments refers to the administration of medicaments such that the individual medicaments are present within a subject at the same time. In addition to the concomitant administration of medicaments (via the same or alternative routes), simultaneous administration may include the administration of the medicaments (via the same or an alternative route) at different times.

"Chothia" as used herein means an antibody numbering system described in Al-Lazikani et al., *JMB* 273:927-948 (1997).

"Conservatively modified variants" or "conservative substitution" refers to substitutions of amino acids in a protein with other amino acids having similar characteristics (e.g., charge, side-chain size, hydrophobicity/hydrophilicity, backbone conformation and rigidity, etc.), such that the changes can frequently be made without altering the biological activity or other desired property of the protein, such as antigen affinity and/or specificity. Those of skill in this art recognize that, in general, single amino acid substitutions in non-essential regions of a polypeptide do not substantially alter biological activity (see, e.g., Watson et al. (1987) *Molecular Biology of the Gene*, The Benjamin/Cummings Pub. Co., p. 224 (4th Ed.)). In addition, substitutions of structurally or functionally similar amino acids are less likely to disrupt biological activity. Exemplary conservative substitutions are set forth in Table 1 below.

TABLE 1

Exemplary Conservative Amino Acid Substitutions

| Original residue | Conservative substitution |
|---|---|
| Ala (A) | Gly; Ser |
| Arg (R) | Lys; His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

"Consists essentially of," and variations such as "consist essentially of" or "consisting essentially of," as used throughout the specification and claims, indicate the inclusion of any recited elements or group of elements, and the optional inclusion of other elements, of similar or different nature than the recited elements, that do not materially change the basic or novel properties of the specified dosage regimen, method, or composition.

"Diagnostic anti-PD-L monoclonal antibody" means a mAb that specifically binds to the mature form of the designated PD-L (PD-L1 or PDL2) expressed on the surface of certain mammalian cells. A mature PD-L lacks the presecretory leader sequence, also referred to as leader peptide. The terms "PD-L" and "mature PD-L" are used interchangeably herein, and shall be understood to mean the same molecule unless otherwise indicated or readily apparent from the context.

As used herein, a diagnostic anti-human PD-L1 mAb or an anti-hPD-L1 mAb refers to a monoclonal antibody that specifically binds to mature human PD-L1. A mature human PD-L1 molecule consists of amino acids 19-290 set forth in SEQ ID NO 21.

Specific examples of diagnostic anti-human PD-L1 mAbs useful as diagnostic mAbs for IHC detection of PD-L1 expression in FFPE tumor tissue sections are antibodies 20C3 and 22C3, which are described in PCT International Patent Application Publication No. WO2014/100079. Another anti-human PD-L1 mAb that has been reported to be useful for IHC detection of PD-L1 expression in FFPE tissue sections (Chen, B. J. et al., *Clin Cancer Res* 19: 3462-3473 (2013)) is a rabbit anti-human PD-L1 mAb publicly available from Sino Biological, Inc. (Beijing, P. R. China; Catalog number 10084-R015).

"Homology" refers to sequence similarity between two polypeptide sequences when they are optimally aligned. When a position in both of the two compared sequences is occupied by the same amino acid monomer subunit, e.g., if a position in a light chain CDR of two different Abs is occupied by alanine, then the two Abs are homologous at that position. The percent of homology is the number of homologous positions shared by the two sequences divided by the total number of positions compared×100. For example, if 8 of 10 of the positions in two sequences are matched when the sequences are optimally aligned then the two sequences are 80% homologous. Generally, the comparison is made when two sequences are aligned to give maximum percent homology. For example, the comparison can be performed by a BLAST algorithm wherein the parameters of the algorithm are selected to give the largest match between the respective sequences over the entire length of the respective reference sequences.

The following references relate to BLAST algorithms often used for sequence analysis: BLAST ALGORITHMS: Altschul, S. F., et al., (1990) J. Mol. Biol. 215:403-410; Gish, W., et al., (1993) Nature Genet. 3:266-272; Madden, T. L., et al., (1996) Meth. Enzymol. 266:131-141; Altschul, S. F., et al., (1997) Nucleic Acids Res. 25:3389-3402; Zhang, J., et al., (1997) Genome Res. 7:649-656; Wootton, J. C., et al., (1993) Comput. Chem. 17:149-163; Hancock, J. M. et al., (1994) Comput. Appl. Biosci. 10:67-70; ALIGNMENT SCORING SYSTEMS: Dayhoff, M. O., et al., "A model of evolutionary change in proteins." in Atlas of Protein Sequence and Structure, (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships." in Atlas of Protein Sequence and Structure, (1978) vol. 5, suppl. 3." M. O. Dayhoff (ed.), pp. 353-358, Natl. Biomed. Res. Found., Washington, D.C.; Altschul, S. F., (1991) J. Mol. Biol. 219:555-565; States, D. J., et al., (1991) Methods 3:66-70; Henikoff, S., et al., (1992) Proc. Natl. Acad. Sci. USA 89:10915-10919; Altschul, S. F., et al., (1993) J. Mol. Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci. USA 90:5873-5877; Dembo, A., et al., (1994) Ann. Prob. 22:2022-2039; and Altschul, S. F. "Evaluating the statistical significance of multiple distinct local alignments." in Theoretical and Computational Methods in Genome Research (S. Suhai, ed.), (1997) pp. 1-14, Plenum, N.Y.

The term "isolated" as used in reference to an antibody or fragment thereof refers to the purification status and, in such context, means the named molecule is substantially free of other biological molecules such as nucleic acids, proteins, lipids, carbohydrates, or other material such as cellular debris and growth media. Generally, the term "isolated" is not intended to refer to a complete absence of such material or to an absence of water, buffers, or salts, unless they are present in amounts that substantially interfere with experimental or therapeutic use of the binding compound as described herein.

"Kabat" as used herein means an immunoglobulin alignment and numbering system pioneered by Elvin A. Kabat ((1991) Sequences of Proteins of Immunological Interest, 5th Ed. Public Health Service, National Institutes of Health, Bethesda, Md.).

"Monoclonal antibody" or "mAb" or "Mab", as used herein, refers to a population of substantially homogeneous antibodies, i.e., the antibody molecules comprising the population are identical in amino acid sequence except for possible naturally occurring mutations that may be present in minor amounts. In contrast, conventional (polyclonal) antibody preparations typically include a multitude of different antibodies having different amino acid sequences in their variable domains, particularly their CDRs, which are often specific for different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by the hybridoma method first described by Kohler et al. (1975) *Nature* 256: 495, or may be made by recombinant DNA methods (see, e.g., U.S. Pat. No. 4,816,567). The "monoclonal antibodies" may also be isolated from phage antibody libraries using the techniques described in Clackson et al. (1991) *Nature* 352: 624-628 and Marks et al. (1991) *J. Mol. Biol.* 222: 581-597, for example. See also Presta (2005) *J. Allergy Clin. Immunol.* 116:731.

"RECIST 1.1 Response Criteria" as used herein means the definitions set forth in Eisenhauer, E. A. et al., *Eur. J. Cancer* 45:228-247 (2009) for target lesions or nontarget lesions, as appropriate based on the context in which response is being measured.

"Sustained response" means a sustained therapeutic effect after cessation of treatment as described herein. In some embodiments, the sustained response has a duration that is at least the same as the treatment duration, or at least 1.5, 2.0, 2.5 or 3 times longer than the treatment duration.

"Tissue Section" refers to a single part or piece of a tissue, e.g., a thin slice of tissue cut from a sample of a normal tissue or of a tumor.

"Treat" or "treating" a cell-proliferation disorder as used herein means to administer a combination therapy of a PD-1 antagonist and a benzo[b]thiophene STING agonist to a subject having a cell-proliferation disorder, such as cancer, or diagnosed with a cell-proliferation disorder, such as cancer, to achieve at least one positive therapeutic effect, such as for example, reduced number of cancer cells, reduced tumor size, reduced rate of cancer cell infiltration into peripheral organs, or reduced rate of tumor metastasis or tumor growth. Such "treatment" may result in a slowing, interrupting, arresting, controlling, or stopping of the progression of a cell-proliferation disorder as described herein but does not necessarily indicate a total elimination of the cell-proliferation disorder or the symptoms of the cell-proliferation disorder. Positive therapeutic effects in cancer can be measured in a number of ways (See, W. A. Weber, *J. Nucl. Med.* 50:1S-10S (2009)). For example, with respect to tumor growth inhibition, according to NCI standards, a T/C≤42% is the minimum level of anti-tumor activity. A T/C<10% is considered a high anti-tumor activity level, with T/C (%)=Median tumor volume of the treated/Median tumor volume of the control×100. In some embodiments, the treatment achieved by a combination therapy of the disclosure is any of PR, CR, OR, PFS, DFS, and OS. PFS, also referred to as "Time to Tumor Progression" indicates the length of time during and after treatment that the cancer does not grow, and includes the amount of time patients have experienced a CR or PR, as well as the amount of time patients have experienced SD. DFS refers to the length of time during and after treatment that the patient remains free of disease. OS refers to a prolongation in life expectancy as compared to naive or untreated individuals or patients. In some embodiments, response to a combination therapy of the disclosure is any of PR, CR, PFS, DFS, or OR that is assessed using RECIST 1.1 response criteria. The treatment regimen for a combination therapy of the disclosure that is effective to treat a cancer patient may vary according to factors such as the disease state, age, and weight of the patient, and the ability of the therapy to elicit an anti-cancer response in the subject. While an embodiment of any of the aspects of the disclosure may not be effective in achieving a positive therapeutic effect in every subject, it should do so in a statistically significant number of subjects as determined by any statistical test known in the art such as the Student's t-test, the chi$^2$-test, the U-test according to Mann and Whitney, the Kruskal-Wallis test (H-test), Jonckheere-Terpstra-test and the Wilcoxon-test.

As used herein, the terms "combination therapy" and "therapeutic combination" refer to treatments in which at least one PD-1 antagonist and at least one benzo[b]thiophene STING agonist, and optionally additional therapeutic agents, each are administered to a patient in a coordinated manner, over an overlapping period of time. The period of treatment with the at least one PD-1 antagonist (the "anti-PD-1 treatment") is the period of time that a patient undergoes treatment with the PD-1 antagonist; that is, the period of time from the initial dosing with the PD-1 antagonist through the final day of a treatment cycle. Similarly, the period of treatment with the at least one benzo[b]thiophene STING agonist (the "benzo[b]thiophene STING agonist treatment") is the period of time that a patient undergoes treatment with the CDN STING agonist; that is, the period of time from the initial dosing with the benzo[b]thiophene STING agonist through the final day of a treatment cycle. In the therapeutic combinations described herein, the anti-PD-1 treatment overlaps by at least one day the benzo[b]thiophene STING agonist treatment. In certain embodiments, the anti-PD-1 treatment and the benzo[b]thiophene STING agonist treatment are coextensive. In embodiments, the anti-PD-1 treatment begins prior to the benzo[b]thiophene STING agonist treatment. In embodiments, the benzo[b]thiophene STING agonist treatment begins prior to the anti-PD-1 treatment. In embodiments, the anti-PD-1 treatment is terminated prior to termination of the benzo[b]thiophene STING agonist treatment. In embodiments, the benzo[b]thiophene STING agonist treatment is terminated prior to termination of the anti-PD-1 treatment.

The terms "treatment regimen", "dosing protocol", and "dosing regimen" are used interchangeably to refer to the dose and timing of administration of each therapeutic agent in a combination therapy of the disclosure.

"Tumor" as it applies to a subject diagnosed with, or suspected of having, a cancer refers to a malignant or potentially malignant neoplasm or tissue mass of any size, and includes primary tumors and secondary neoplasms. A solid tumor is an abnormal growth or mass of tissue that usually does not contain cysts or liquid areas. Different types of solid tumors are named for the type of cells that form them. Examples of solid tumors are sarcomas, carcinomas, and lymphomas. Leukemias (cancers of the blood) generally do not form solid tumors (National Cancer Institute, Dictionary of Cancer Terms).

"Advanced solid tumor malignancy" and "advanced solid tumor" are used interchangeably to refer to a tumor for which curative resection is not possible. Advanced solid tumors include, but are not limited to, metastatic tumors in bone, brain, breast, liver, lungs, lymph node, pancreas, prostate, and soft tissue (sarcoma).

"Tumor burden" also referred to as "tumor load", refers to the total amount of tumor material distributed throughout the body. Tumor burden refers to the total number of cancer cells or the total size of tumor(s), throughout the body, including lymph nodes and bone narrow. Tumor burden can be determined by a variety of methods known in the art, such as, e.g., by measuring the dimensions of tumor(s) upon removal from the subject, e.g., using calipers, or while in the body using imaging techniques, e.g., ultrasound, bone scan, computed tomography (CT) or magnetic resonance imaging (MRI) scans.

The term "tumor size" refers to the total size of the tumor which can be measured as the length and width of a tumor. Tumor size may be determined by a variety of methods known in the art, such as, e.g., by measuring the dimensions of tumor(s) upon removal from the subject, e.g., using calipers, or while in the body using imaging techniques, e.g., bone scan, ultrasound, CT or MRI scans.

It is understood that wherever embodiments are described herein with the language "comprising," otherwise analogous embodiments described in terms of "consisting of" and/or "consisting essentially of" are also provided.

The term "alkyl" refers to a monovalent straight or branched chain, saturated aliphatic hydrocarbon radical having a number of carbon atoms in the specified range. Thus, for example, "$C_{1-6}$ alkyl" (or "$C_1$-$C_6$ alkyl") refers to any of the hexyl alkyl and pentyl alkyl isomers as well as n-, iso-, sec-, and tert-butyl, n- and iso-propyl, ethyl, and methyl. As another example, "$C_{1-4}$ alkyl" refers to n-, iso-, sec-, and tert-butyl, n- and isopropyl, ethyl, and methyl.

As used herein, the term "alkylene" refers to a bivalent straight chain, saturated aliphatic hydrocarbon radical having a number of carbon atoms in the specified range.

As used herein, the term "alkenyl" refers to a monovalent straight or branched chain, unsaturated aliphatic hydrocarbon radical having a number of carbon atoms in the specified range and including one or more double bond.

As used herein, the term "alkenylene" refers to a bivalent straight chain, unsaturated aliphatic hydrocarbon radical having a number of carbon atoms in the specified range and including one or more double bond.

As used herein, the term "alkynyl" refers to a monovalent straight or branched chain, unsaturated aliphatic hydrocarbon radical having a number of carbon atoms in the specified range and including one or more triple bond.

As used herein, the term "alkynylene" refers to a bivalent straight chain, unsaturated aliphatic hydrocarbon radical having a number of carbon atoms in the specified range and including one or more triple bond.

The term "halogen" (or "halo") refers to fluorine, chlorine, bromine, and iodine (alternatively referred to as fluoro, chloro, bromo, and iodo or F, Cl, Br, and I).

The term "haloalkyl" refers to an alkyl group as defined above in which one or more of the hydrogen atoms have been replaced with a halogen. Thus, for example, "$C_{1-6}$ haloalkyl" (or "$C_1$-$C_6$ haloalkyl") refers to a $C_1$ to $C_6$ linear or branched alkyl group as defined above with one or more halogen substituents. The term "fluoroalkyl" has an analogous meaning except the halogen substituents are restricted to fluoro. Suitable fluoroalkyls include the series $(CH_2)_{0-4}CF_3$ (i.e., trifluoromethyl, 2,2,2-trifluoroethyl, 3,3,3-trifluoro-n-propyl, etc.).

As used herein, the term "haloalkenyl" refers to an alkenyl group as defined above in which one or more of the hydrogen atoms have been replaced with a halogen.

As used herein, the term "haloalkynyl" refers to an alkynyl group as defined above in which one or more of the hydrogen atoms have been replaced with a halogen.

As used herein, the term "alkoxy" as used herein, alone or in combination, includes an alkyl group connected to the oxy connecting atom. The term "alkoxy" also includes alkyl ether groups, where the term 'alkyl' is defined above, and 'ether' means two alkyl groups with an oxygen atom between them. Examples of suitable alkoxy groups include methoxy, ethoxy, n-propoxy, i-propoxy, n-butoxy, s-butoxy, t-butoxy, methoxymethane (also referred to as 'dimethyl ether'), and methoxyethane (also referred to as 'ethyl methyl ether').

As used herein, the term "cycloalkyl" refers to a saturated hydrocarbon containing one ring having a specified number of carbon atoms. Examples of cycloalkyl include cyclopropyl, cyclobutyl, cyclopentyl, and cyclohexyl.

As used herein, the term "heterocycle", "heterocyclyl", or "heterocyclic", as used herein, represents a stable 3- to 6-membered monocyclic that is either saturated or unsaturated, and that consists of carbon atoms and from one to two heteroatoms selected from the group consisting of N, O, and S. The heterocyclic ring may be attached at any heteroatom or carbon atom which results in the creation of a stable structure. The term includes heteroaryl moieties. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, triazolyl and thienyl.

As used herein, the term "fused ring" refers to a cyclic group formed by substituents on separate atoms in a straight or branched alkane, or to a cyclic group formed by substituents on separate atoms in another ring.

As used herein, the term "spirocycle" or "spirocyclic ring" refers to a pendant cyclic group formed by substituents on a single atom.

Unless expressly stated to the contrary, all ranges cited herein are inclusive; i.e., the range includes the values for the upper and lower limits of the range as well as all values in between. As an example, temperature ranges, percentages, ranges of equivalents, and the like described herein include the upper and lower limits of the range and any value in the continuum there between. Numerical values provided herein, and the use of the term "about", may include variations of ±1%, ±2%, ±3%, ±4%, ±5%, ±10%, ±15%, and ±20% and their numerical equivalents. All ranges also are intended to include all included sub-ranges, although not necessarily explicitly set forth. For example, a range of 3 to 7 days is intended to include 3, 4, 5, 6, and 7 days. In addition, the term "or," as used herein, denotes alternatives that may, where appropriate, be combined; that is, the term "or" includes each listed alternative separately as well as their combination.

Where aspects or embodiments of the disclosure are described in terms of a Markush group or other grouping of alternatives, the present disclosure encompasses not only the entire group listed as a whole, but each member of the group individually and all possible subgroups of the main group, but also the main group absent one or more of the group members. The present disclosure also envisages the explicit exclusion of one or more of any of the group members in the claims.

Unless otherwise defined, all technical and scientific terms used herein have the same meaning as commonly understood by one of ordinary skill in the art to which this disclosure relates. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular. Any example(s) following the term "e.g." or "for example" is not meant to be exhaustive or limiting.

Exemplary methods and materials are described herein, although methods and materials similar or equivalent to those described herein can also be used in the practice or testing of the present disclosure. The materials, methods, and examples are illustrative only and not intended to be limiting.

The present disclosure relates to methods of treating a cell-proliferation disorder as defined herein, wherein the method comprises administering to a subject in need thereof a combination therapy that comprises (a) a PD-1 antagonist; and (b) a benzo[b]thiophene STING agonist.

The present disclosure relates to methods of treating a cell-proliferation disorder, wherein the method comprises administering to a subject in need thereof a combination therapy that comprises (a) a PD-1 antagonist; and (b) a benzo[b]thiophene STING agonist; wherein the cell-proliferation disorder is selected from the group consisting of solid tumors and lymphomas.

PD-1 Antagonist

"PD-1 antagonist" or "PD-1 pathway antagonist" means any chemical compound or biological molecule that blocks binding of PD-L1 expressed on a cancer cell to PD-1 expressed on an immune cell (T-cell, B-cell, or NKT-cell) and preferably also blocks binding of PD-L2 expressed on a cancer cell to the immune-cell expressed PD-1. Alternative names or synonyms for PD-1 and its ligands include: PDCD1, PD1, CD279, and SLEB2 for PD-1; PDCD1L1, PDL1, B7H1, B7-4, CD274, and B7-H for PD-L1; and PDCD1L2, PDL2, B7-DC, Btdc, and CD273 for PD-L2. In any of the treatment methods, medicaments and uses of the present disclosure in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively, and in SEQ ID NO: 21.

PD-1 antagonists useful in any of the treatment methods, medicaments and uses of the present disclosure include a mAb, or antigen binding fragment thereof, which specifically binds to PD-1 or PD-L1, and preferably specifically binds to human PD-1 or human PD-L1. The mAb may be a human antibody, a humanized antibody, or a chimeric antibody and may include a human constant region. In some embodiments, the human constant region is selected from the group consisting of IgG1, IgG2, IgG3, and IgG4 constant regions, and in specific embodiments, the human constant region is an IgG1 or IgG4 constant region. In some embodiments, the antigen binding fragment is selected from the group consisting of Fab, Fab'-SH, F(ab')$_2$, scFv, and Fv fragments.

Examples of mAbs that bind to human PD-1, and that may be useful in the treatment methods, medicaments, and uses of the present disclosure, are described in U.S. Pat. Nos. U.S. Pat. Nos. 7,488,802, 7,521,051, 8,008,449, 8,354,509, and 8,168,757, PCT International Patent Application Publication Nos. WO2004/004771, WO2004/072286, and WO2004/056875, and U.S. Patent Application Publication No. US20110271358.

Examples of mAbs that bind to human PD-L1, and that may be useful in the treatment methods, medicaments and uses of the present disclosure, are described in PCT International Patent Application Nos. WO2013/019906 and WO2010/077634 and in U.S. Pat. No. 8,383,796. Specific anti-human PD-L1 mAbs useful as the PD-1 antagonist in the treatment methods, medicaments, and uses of the present disclosure include MPDL3280A, BMS-936559, MEDI4736, MSB0010718C, and an antibody that comprises the heavy chain and light chain variable regions of SEQ ID NO:24 and SEQ ID NO:21, respectively, of WO2013/019906. In particular embodiments, the PD-1 antagonist is an antigen binding fragment having variable regions comprising the heavy and light chain CDRs of WO2013/019906.

Other PD-1 antagonists useful in any of the treatment methods, medicaments, and uses of the present disclosure include an immune-adhesion molecule that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immune-adhesion molecules that specifically bind to PD-1 are described in PCT International Patent Application Publication Nos. WO2010/027827 and WO2011/066342. Specific fusion proteins useful as the PD-1 antagonist in the treatment methods, medicaments, and uses of the present disclosure include AMP-224 (also known as B7-DCIg), which is a PD-L2-FC fusion protein and binds to human PD-1.

In embodiments, the PD-1 antagonist can be conjugated, e.g., to small drug molecules, enzymes, liposomes, polyethylene glycol (PEG).

In some embodiments of the treatment methods, medicaments, and uses of the present disclosure, the PD-1 antagonist is a monoclonal antibody, or antigen binding fragment thereof, which specifically binds to human PD-1 and comprises (a) a heavy chain variable region comprising CDRH1 of SEQ ID NO 8, CDRH2 of SEQ ID NO 9, and CDRH3 of SEQ ID NO 10, and (b) a light chain variable region comprising CDRL1 of SEQ ID NO 5, CDRL2 of SEQ ID NO 6, and CDRL3 of SEQ ID NO 7. In specific embodiments, the PD-1 antagonist is a monoclonal antibody, or antigen binding fragment thereof, which specifically binds to human PD-1 and comprises (a) a heavy chain variable region comprising SEQ ID NO 2, and (b) a light chain variable region comprising SEQ ID NO 1. In specific embodiments, the PD-1 antagonist is a monoclonal antibody, or antigen binding fragment thereof, which specifically binds to human PD-1 and comprises (a) a heavy chain comprising SEQ ID NO 4, and (b) a light chain comprising SEQ ID NO 3.

In some embodiments of the treatment methods, medicaments, and uses of the present disclosure, the PD-1 antagonist is a monoclonal antibody, or antigen binding fragment thereof, which specifically binds to human PD-1 and comprises (a) a heavy chain variable region comprising CDRH1 of SEQ ID NO 18, CDRH2 of SEQ ID NO 19, and CDRH3 of SEQ ID NO 20, and (b) a light chain variable region comprising CDRL1 of SEQ ID NO 15, CDRL2 of SEQ ID NO 16, and CDRL3 of SEQ ID NO 17. In specific embodiments, the PD-1 antagonist is a monoclonal antibody, or antigen binding fragment thereof, which specifically binds to human PD-1 and comprises (a) a heavy chain variable region comprising SEQ ID NO 12, and (b) a light chain variable region comprising SEQ ID NO 11. In specific embodiments, the PD-1 antagonist is a monoclonal antibody, or antigen binding fragment thereof, which specifically binds to human PD-1 and comprises (a) a heavy chain comprising SEQ ID NO 14, and (b) a light chain comprising SEQ ID NO 13.

In some embodiments of the treatment methods, medicaments, and uses of the present disclosure, the PD-1 antagonist is an anti-PD-1 monoclonal antibody. In aspects of these embodiments, the PD-1 antagonist is selected from the group consisting of nivolumab, pembrolizumab, pidilizumab, and AMP-224. In specific aspects, the PD-1 antagonist is selected from nivolumab and pembrolizumab. In a more specific aspect, the PD-1 antagonist is nivolumab. In a further specific aspect, the PD-1 antagonist is pembrolizumab.

The present disclosure relates to PD-1 antagonists that are monoclonal antibodies, or antigen binding fragments thereof, which specifically bind to human PD-1 as described herein. In embodiments, PD-1 antagonists may comprise variant heavy chain variable region sequence and/or variant light chain variable region sequence identical to the reference sequence except having up to 17 conservative amino acid substitutions in the framework region (i.e., outside of the CDRs), and preferably have less than ten, nine, eight, seven, six, or five conservative amino acid substitutions in the framework region.

Table 2 below provides a list of the amino acid sequences of exemplary anti-PD-1 mAbs for use in the treatment methods, medicaments, and uses of the present disclosure, and the sequences are shown in FIGS. 1-9.

TABLE 2

Description of Sequences in Sequence Listing

| SEQ ID NO: | Description |
|---|---|
| 1 | Pembrolizumab, variable light chain, amino acid |
| 2 | Pembrolizumab, variable heavy chain, amino acid |

TABLE 2-continued

Description of Sequences in Sequence Listing

| SEQ ID NO: | Description |
|---|---|
| 3 | Pembrolizumab, light chain, amino acid |
| 4 | Pembrolizumab, heavy chain, amino acid |
| 5 | Pembrolizumab, CDRL1 |
| 6 | Pembrolizumab, CDRL2 |
| 7 | Pembrolizumab, CDRL3 |
| 8 | Pembrolizumab, CDRH1 |
| 9 | Pembrolizumab, CDRH2 |
| 10 | Pembrolizumab, CDRH3 |
| 11 | Nivolumab, variable light chain, amino acid |
| 12 | Nivolumab, variable heavy chain, amino acid |
| 13 | Nivolumab, light chain, amino acid |
| 14 | Nivolumab, heavy chain, amino acid |
| 15 | Nivolumab, CDRL1 |
| 16 | Nivolumab, CDRL2 |
| 17 | Nivolumab, CDRL3 |
| 18 | Nivolumab, CDRH1 |
| 19 | Nivolumab, CDRH2 |
| 20 | Nivolumab, CDRH3 |
| 21 | Human PD-L1 |

"PD-L1" expression or "PD-L2" expression as used herein means any detectable level of expression of the designated PD-L protein on the cell surface or of the designated PD-L mRNA within a cell or tissue. PD-L protein expression may be detected with a diagnostic PD-L antibody in an IHC assay of a tumor tissue section or by flow cytometry. Alternatively, PD-L protein expression by tumor cells may be detected by PET imaging, using a binding agent (e.g., antibody fragment, affibody, and the like) that specifically binds to the desired PD-L target, e.g., PD-L1 or PD-L2. Techniques for detecting and measuring PD-L mRNA expression include RT-PCR and realtime quantitative RT-PCR.

Several approaches have been described for quantifying PD-L1 protein expression in IHC assays of tumor tissue sections. See, e.g., Thompson, R. H., et al., *PNAS* 101 (49); 17174-17179 (2004); Thompson, R. H. et al., *Cancer Res.* 66:3381-3385 (2006); Gadiot, J., et al., *Cancer* 117:2192-2201 (2011); Taube, J. M. et al., *Sci Transl Med* 4, 127ra37 (2012); and Toplian, S. L. et al., *New Eng. J. Med.* 366 (26): 2443-2454 (2012).

One approach employs a simple binary end-point of positive or negative for PD-L1 expression, with a positive result defined in terms of the percentage of tumor cells that exhibit histologic evidence of cell-surface membrane staining. A tumor tissue section is counted as positive for PD-L1 expression is at least 1%, and preferably 5% of total tumor cells.

In another approach, PD-L1 expression in the tumor tissue section is quantified in the tumor cells as well as in infiltrating immune cells, which predominantly comprise lymphocytes. The percentage of tumor cells and infiltrating immune cells that exhibit membrane staining are separately quantified as <5%, 5 to 9%, and then in 10% increments up to 100%. For tumor cells, PD-L1 expression is counted as negative if the score is <5% score and positive if the score is ≥5%. PD-L1 expression in the immune infiltrate is reported as a semi-quantitative measurement called the adjusted inflammation score (AIS), which is determined by multiplying the percent of membrane staining cells by the intensity of the infiltrate, which is graded as none (0), mild (score of 1, rare lymphocytes), moderate (score of 2, focal infiltration of tumor by lymphohistiocytic aggregates), or severe (score of 3, diffuse infiltration). A tumor tissue section is counted as positive for PD-L1 expression by immune infiltrates if the AIS is ≥5.

The level of PD-L1 mRNA expression may be compared to the mRNA expression levels of one or more reference genes that are frequently used in quantitative RT-PCR, such as ubiquitin C.

In some embodiments, a level of PD-L1 expression (protein and/or mRNA) by malignant cells and/or by infiltrating immune cells within a tumor is determined to be "overexpressed" or "elevated" based on comparison with the level of PD-L1 expression (protein and/or mRNA) by an appropriate control. For example, a control PD-L1 protein or mRNA expression level may be the level quantified in nonmalignant cells of the same type or in a section from a matched normal tissue. In some embodiments, PD-L1 expression in a tumor sample is determined to be elevated if PD-L1 protein (and/or PD-L1 mRNA) in the sample is at least 10%, 20%, or 30% greater than in the control.

Benzo[b]Thiophene Sting Agonists

As used herein, "benzo[b]thiophene STING agonist" means any benzo[b]thiophene STING agonist chemical compound that activates the STING pathway, and in particular, the benzo[b]thiophene STING agonist STING agonists as disclosed in U.S. Provisional Patent Application No. 62/404,062, filed Oct. 4, 2016, which is incorporated herein in its entirety. Benzo[b]thiophene STING agonist STING agonists, and particularly the compounds of formulas (I), (Ia), and (Ib), may be used in the therapeutic combinations of this disclosure.

In embodiments, the benzo[b]thiophene STING agonist is selected from benzo[b]thiophene compounds of formula (Ia):

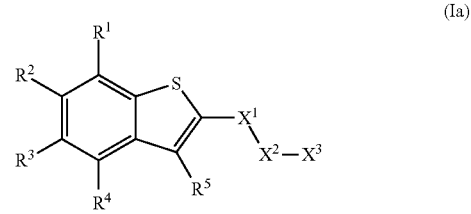

(Ia)

or a pharmaceutically acceptable salt thereof, wherein $R^1$ is selected from the group consisting of H, halogen, $OR^6$, $N(R^6)_2$, $C_1$-$C_6$ alkyl, $C_1$-$C_6$ haloalkyl, $C_1$-$C_6$ alkyl substituted by $OR^6$, $C_1$-$C_6$ alkyl substituted by $N(R^6)_2$, $COOR^6$, and $C(O)N(R^6)_2$; $R^2$ is selected from the group consisting of halogen, CN, $OR^6$, $N(R^6)_2$, $COOR^6$, $C(O)N(R^6)_2$, $SO_2R^6$, $C_1$-$C_6$ alkyl, $C_1$-$C_6$ haloalkyl, $C_1$-$C_6$ alkyl substituted by $OR^6$, $C_2$-$C_6$ alkenyl, $C_2$-$C_6$ haloalkenyl, $C_2$-$C_6$ alkenyl substituted by $OR^6$, $C_2$-$C_6$ alkynyl, $C_2$-$C_6$ haloalkynyl, $C_2$-$C_6$ alkynyl substituted by $OR^6$, $C_3$-$C_6$ cycloalkyl, and a 3- to 6-membered heterocyclic ring including 1 to 2 ring members selected from the group consisting of O, S, N, and $N(R^6)$; $R^3$ is selected from the group consisting of halogen, CN, $OR^6$, $N(R^6)_2$, $COOR^6$, $C(O)N(R^6)_2$, $SO_2R^6$, $C_1$-$C_6$ alkyl, $C_1$-$C_6$ haloalkyl, $C_1$-$C_6$ alkyl substituted by $OR^6$, $C_2$-$C_6$ alkenyl, $C_2$-$C_6$ haloalkenyl, $C_2$-$C_6$ alkenyl substituted by $OR^6$, $C_2$-$C_6$ alkynyl, $C_2$-$C_6$ haloalkynyl, $C_2$-$C_6$ alkynyl substituted by $OR^6$, $C_3$-$C_6$ cycloalkyl, and a 3- to 6-membered heterocyclic ring including 1 to 2 ring members selected from the group consisting of O, S, N, and $N(R^6)$; $R^4$ is selected from the group consisting of H, halogen, $OR^6$, $N(R^6)_2$, $C_1$-$C_6$ alkyl, $C_1$-$C_6$ haloalkyl, $C_1$-$C_6$ alkyl substituted by $OR^6$, $C_1$-$C_6$ alkyl substituted by $N(R^6)_2$, $COOR^6$, and $C(O)N(R^6)_2$; $R^5$ is selected from H, halogen, $OR^6$, $N(R^6)_2$, CN, $C_1$-$C_6$ alkyl, $C_1$-$C_6$ haloalkyl, $C_1$-$C_6$ alkyl substituted by $OR^6$, $COOR^6$, and $C(O)N(R^6)_2$; each $R^6$ is independently selected from the group consisting of H, $C_1$-$C_6$ alkyl, and $C_1$-$C_6$ haloalkyl; $X^1$ is $C(O)$; $X^2$ is $(C(R^8)_2)_{(1-3)}$; each $R^8$ is independently selected from the group consisting of H, halogen, $C_1$-$C_6$ alkyl, CN, $OR^6$, $N(R^6)_2$, $C_1$-$C_6$ haloalkyl, $C_3$-$C_6$ cycloalkyl, $C_1$-$C_6$ alkyl substituted by $OR^6$, and $C_1$-$C_6$ alkyl substituted by $N(R^6)_2$; optionally 2 $R^8$ may be taken together, along with the atoms to which they are attached, to form a 3- to 6-membered fused ring; optionally 2 $R^8$ may be taken together, along with the atoms to which they are attached, to form a 3- to 6-membered spirocycle; $X^3$ is selected from the group consisting of $COOR^6$, $C(O)SR^6$, $C(S)OR^6$, $SO_2R^6$, and $C(O)N(R^9)_2$; and each $R^9$ is independently selected from the group consisting of H, $COOR^6$, and $SO_2R^6$; wherein when $X^1$—$X^2$—$X^3$ is $X^1$—$CHR^8$—$X^3$ or $X^1$—$CHR^8CH_2$—$X^3$, at least one of $R^2$ and $R^3$ is not selected from the group consisting of halogen, $OR^6$, $C_1$-$C_6$ alkyl, and $C_1$-$C_6$ haloalkyl.

In aspects of this embodiment, $R^1$ is selected from the group consisting of H, halogen, $OR^6$, $N(R^6)_2$, $C_1$-$C_6$ alkyl, $C_1$-$C_6$ haloalkyl, $C_1$-$C_6$ alkyl substituted by $OR^6$, $C_1$-$C_6$ alkyl substituted by $N(R^6)_2$, $COOR^6$, and $C(O)N(R^6)_2$. In instances of this aspect, $R^1$ is selected from the group consisting of H, F, Cl, $C_1$-$C_3$ alkyl, and $C_1$-$C_3$ haloalkyl. In particular instances of this aspect, $R^1$ is selected from the group consisting of H and F. In this aspect, all other groups are as provided in the general formula (Ia) above.

In aspects of this embodiment, $R^2$ is selected from the group consisting of halogen, CN, $OR^6$, $N(R^6)_2$, $COOR^6$, $C(O)N(R^6)_2$, $SO_2R^6$, $C_1$-$C_6$ alkyl, $C_1$-$C_6$ haloalkyl, $C_1$-$C_6$ alkyl substituted by $OR^6$, $C_2$-$C_6$ alkenyl, $C_2$-$C_6$ haloalkenyl, $C_2$-$C_6$ alkenyl substituted by $OR^6$, $C_2$-$C_6$ alkynyl, $C_2$-$C_6$ haloalkynyl, $C_2$-$C_6$ alkynyl substituted by $OR^6$, $C_3$-$C_6$ cycloalkyl, and a 3- to 6-membered heterocyclic ring including 1 to 2 ring members selected from the group consisting of O, S, N, and $N(R^6)$. In instances of this aspect, $R^2$ is selected from the group consisting of halogen, $C_1$-$C_3$ alkyl, $C_1$-$C_3$ haloalkyl, $OC_1$-$C_3$ alkyl, $C_2$-$C_3$ alkenyl, and $N(R^6)_2$. In particular instances of this aspect, $R^2$ is selected from the group consisting of Br, Cl, $CH_3$, $CH_2CH_3$, $CH=CH_2$, $OCH_3$, and $N(R^6)_2$. In this aspect, all other groups are as provided in the general formula (Ia) or aspects described above.

In aspects of this embodiment, $R^3$ is selected from the group consisting of halogen, CN, $OR^6$, $N(R^6)_2$, $COOR^6$, $C(O)N(R^6)_2$, $SO_2R^6$, $C_1$-$C_6$ alkyl, $C_1$-$C_6$ haloalkyl, $C_1$-$C_6$ alkyl substituted by $OR^6$, $C_2$-$C_6$ alkenyl, $C_2$-$C_6$ haloalkenyl, $C_2$-$C_6$ alkenyl substituted by $OR^6$, $C_2$-$C_6$ alkynyl, $C_2$-$C_6$ haloalkynyl, $C_2$-$C_6$ alkynyl substituted by $OR^6$, $C_3$-$C_6$ cycloalkyl, and a 3- to 6-membered heterocyclic ring including 1 to 2 ring members selected from the group consisting of O, S, N, and $N(R^6)$. In instances of this aspect, $R^3$ is selected from the group consisting of halogen, $C_1$-$C_3$ alkyl, $C_1$-$C_3$ haloalkyl, $OC_1$-$C_3$ alkyl, $C_2$-$C_3$ alkenyl, and $N(R^6)_2$. In particular instances of this aspect, $R^3$ is selected from the group consisting of Br, Cl, $CH_3$, $CH_2CH_3$, $CH=CH_2$, $OCH_3$, and $N(R^6)_2$. In this aspect, all other groups are as provided in the general formula (Ia) or aspects described above.

In aspects of this embodiment, $R^4$ is selected from the group consisting of H, halogen, $OR^6$, $N(R^6)_2$, $C_1$-$C_6$ alkyl, $C_1$-$C_6$ haloalkyl, $C_1$-$C_6$ alkyl substituted by $OR^6$, $C_1$-$C_6$ alkyl substituted by $N(R^6)_2$, $COOR^6$, and $C(O)N(R^6)_2$. In instances of this aspect, $R^4$ is selected from the group consisting of H, F, Cl, $C_1$-$C_3$ alkyl, and $C_1$-$C_3$ haloalkyl. In particular instances of this aspect, $R^4$ is selected from the group consisting of H and F. In this aspect, all other groups are as provided in the general formula (Ia) or aspects described above.

In aspects of this embodiment, $R^5$ is selected from the group consisting of H, halogen, $OR^6$, $N(R^6)_2$, CN, $C_1$-$C_6$ alkyl, $C_1$-$C_6$ haloalkyl, $C_1$-$C_6$ alkyl substituted by $OR^6$, $COOR^6$, and $C(O)N(R^6)_2$. In instances of this aspect, $R^5$ is selected from the group consisting of H, F, Cl, $C_1$-$C_3$ alkyl, and $C_1$-$C_3$ haloalkyl. In particular instances of this aspect, $R^5$ is H. In this aspect, all other groups are as provided in the general formula (Ia) or aspects described above.

In aspects of this embodiment, each $R^6$ is independently selected from the group consisting of H, $C_1$-$C_6$ alkyl, and $C_1$-$C_6$ haloalkyl. In instances of this aspect, each $R^6$ is independently selected from the group consisting of H, $C_1$-$C_3$ alkyl, and $C_1$-$C_3$ haloalkyl. In particular instances of this aspect, each $R^6$ is independently selected from the group consisting of H and $CH_3$. In this aspect, all other groups are as provided in the general formula (Ia) or aspects described above.

In aspects of this embodiment, $X^3$ is selected from the group consisting of $COOR^6$, $C(O)SR^6$, $C(S)OR^6$, $SO_2R^6$, and $C(O)N(R^9)_2$. In instances of this aspect, $X^3$ is selected from the group consisting of $COOR^6$, $SO_2R^6$, and $C(O)N(R^9)_2$. In particular instances of this aspect, $X^3$ is $COOR^6$. In even more particular instances of this aspect, $X^3$ is COOH. In this aspect, all other groups are as provided in the general formula (Ia) or aspects described above.

In aspects of this embodiment, each $R^9$ is independently selected from the group consisting of H, $COOR^6$, and $SO_2R^6$. In instances of this aspect, each $R^9$ is independently H. In this aspect, all other groups are as provided in the general formula (Ia) or aspects described above.

In aspects of this embodiment, $X^2$ is $(C(R^8)_2)_{(1-3)}$, wherein each $R^8$ is independently selected from the group consisting of H, halogen, $C_1$-$C_6$ alkyl, CN, $OR^6$, $N(R^6)_2$, $C_1$-$C_6$ haloalkyl, $C_3$-$C_6$ cycloalkyl, $C_1$-$C_6$ alkyl substituted by $OR^6$, and $C_1$-$C_6$ alkyl substituted by $N(R^6)_2$; optionally 2 $R^8$ may be taken together, along with the atoms to which they are attached, to form a 3- to 6-membered fused ring; optionally 2 $R^8$ may be taken together, along with the atoms to which they are attached, to form a 3- to 6-membered spirocycle. In a first instance of this aspect, $X^2$ is $CH_2CHR^8$, where $R^8$ is selected from the group consisting of H, $C_1$-$C_3$ alkyl, $C_1$-$C_3$ alkyl substituted by OH, $C_1$-$C_3$ alkyl substituted by $OC_1$-$C_3$ alkyl, and $C_3$-$C_6$ cycloalkyl. In particular occurrences of this first instance, $X^2$ is $CH_2CHR^8$, wherein $R^8$ is selected from the group consisting of H, $CH_3$, $CH_2OH$, $CH_2CH_3$, $CH_2CH_2CH_3$, $CH(CH_3)_2$, $CH_2OCH_3$, and cyclopropyl. In a second instance of this aspect, $X^2$ is $CHR^8CHR^8$, where $R^8$ is selected from the group consisting of H, $C_1$-$C_3$ alkyl, $C_1$-$C_3$ alkyl substituted by OH, $C_1$-$C_3$ alkyl substituted by $OC_1$-$C_3$ alkyl, and $C_3$-$C_6$ cycloalkyl, and optionally 2 $R^8$ are taken together, along with the atoms to which they are attached, to form a 3- to 6-membered fused ring. In particular occurrences of this second instance, $X^2$ is $CHR^8CHR^8$, where $R^8$ is selected from the group consisting of H and $C_1$-$C_3$ alkyl, and optionally 2 $R^8$ are taken together, along with the atoms to which they are attached, to form a 3- to 6-membered fused ring. In a third instance of this aspect, $X^2$ is $CH_2C(R^8)_2$, where $R^8$ is selected from the group consisting of H, $C_1$-$C_3$ alkyl, $C_1$-$C_3$ alkyl substituted by OH, $C_1$-$C_3$ alkyl substituted by $OC_1$-$C_3$ alkyl, and $C_3$-$C_6$ cycloalkyl, and optionally 2 $R^8$ are taken together, along with the atoms to which they are attached, to form a 3- to 6-membered spirocycle. In particular occurrences of this third instance, $X^2$ is $CH_2C(R^8)_2$, where $R^8$ is selected from the group consisting of H and $C_1$-$C_3$ alkyl, and optionally 2 $R^8$ are taken together, along with the atoms to which they are attached, to form a 3- to 6-membered spirocycle. In this aspect, all other groups are as provided in the general formula (Ia) or aspects described above.

In aspects of this embodiment, 1e is selected from the group consisting of H, F, Cl, $C_1$-$C_3$ alkyl, and $C_1$-$C_3$ haloalkyl; $R^2$ is selected from the group consisting of halogen, $C_1$-$C_3$ alkyl, $C_1$-$C_3$ haloalkyl, $OC_1$-$C_3$ alkyl, $C_2$-$C_3$ alkenyl, and $N(R^6)_2$; $R^3$ is selected from the group consisting of halogen, $C_1$-$C_3$ alkyl, $C_1$-$C_3$ haloalkyl, $OC_1$-$C_3$ alkyl, $C_2$-$C_3$ alkenyl, and $N(R^6)_2$; $R^4$ is selected from the group consisting of H, F, Cl, $C_1$-$C_3$ alkyl, and $C_1$-$C_3$ haloalkyl; $R^5$ is selected from the group consisting of H, F, Cl, $OR^6$, $C_1$-$C_3$ alkyl, and $C_1$-$C_3$ haloalkyl; each $R^6$ is independently selected from the group consisting of H, $C_1$-$C_3$ alkyl, and $C_1$-$C_3$ haloalkyl; $X^1$—$X^2$—$X^3$ is selected from the group consisting of C(O)—$CH_2CHR^8$—$COOR^6$, C(O)—$CH_2CHR^8$—$SO_2R^6$, and C(O)—$CH_2CHR^8$—$C(O)N(R^9)_2$; and each $R^8$ is selected from the group consisting of H, $C_1$-$C_3$ alkyl, $C_1$-$C_3$ alkyl substituted by OH, $C_1$-$C_3$ alkyl substituted by $OC_1$-$C_3$ alkyl, and $C_3$-$C_6$ cycloalkyl. In instances of this aspect, 1e is selected from the group consisting of H and F; $R^2$ is selected from the group consisting of Br, Cl, $CH_3$, $CH_2CH_3$, CH=$CH_2$, $OCH_3$, and $N(R^6)_2$; $R^3$ is selected from the group consisting of Br, Cl, $CH_3$, $CH_2CH_3$, CH=$CH_2$, $OCH_3$, and $N(R^6)_2$; $R^4$ is selected from the group consisting of H and F; $R^5$ is H; each $R^6$ is independently selected from the group consisting of H and $CH_3$; $X^1$—$X^2$—$X^3$ is C(O)—$CH_2CHR^8$—COOH; and $R^8$ is selected from the group consisting of H, $CH_3$, $CH_2CH_3$, $CH_2CH_2CH_3$, $CH(CH_3)_2$, $CH_2OCH_3$, and cyclopropyl. In this aspect, all other groups are as provided in the general formula (Ia) above.

In aspects of this embodiment, 1e is selected from the group consisting of H, F, Cl, $C_1$-$C_3$ alkyl, and $C_1$-$C_3$ haloalkyl; $R^2$ is selected from the group consisting of halogen, $C_1$-$C_3$ alkyl, $C_1$-$C_3$ haloalkyl, $OC_1$-$C_3$ alkyl, $C_2$-$C_3$ alkenyl, and $N(R^6)_2$; $R^3$ is selected from the group consisting of halogen, $C_1$-$C_3$ alkyl, $C_1$-$C_3$ haloalkyl, $OC_1$-$C_3$ alkyl, $C_2$-$C_3$ alkenyl, and $N(R^6)_2$; $R^4$ is selected from the group consisting of H, F, Cl, $C_1$-$C_3$ alkyl, and $C_1$-$C_3$ haloalkyl; $R^5$ is selected from the group consisting of H, F, Cl, $OR^6$, $C_1$-$C_3$ alkyl, and $C_1$-$C_3$ haloalkyl; each $R^6$ is independently selected from the group consisting of H, $C_1$-$C_3$ alkyl, and $C_1$-$C_3$ haloalkyl; $X^{1-}$—$X^2$—$X^3$ is selected from the group consisting of C(O)—$CHR^8CHR^8$—$COOR^6$, C(O)—$CHR^8CHR^8$—$SO_2R^6$, and C(O)—$CHR^8CHR^8$—$C(O)N(R^9)_2$; and each $R^8$ is selected from the group consisting of H, $C_1$-$C_3$ alkyl, $C_1$-$C_3$ alkyl substituted by OH, $C_1$-$C_3$ alkyl substituted by $OC_1$-$C_3$ alkyl, and $C_3$-$C_6$ cycloalkyl, and where optionally 2 $R^8$ are taken together, along with the atoms to which they are attached, to form a 3- to 6-membered fused ring. In instances of this aspect, 1e is selected from the group consisting of H and F; $R^2$ is selected from the group consisting of Br, Cl, $CH_3$, $CH_2CH_3$, CH=$CH_2$, $OCH_3$, and $N(R^6)_2$; $R^3$ is selected from the group consisting of Br, Cl, $CH_3$, $CH_2CH_3$, CH=$CH_2$, $OCH_3$, and $N(R^6)_2$; $R^4$ is selected from the group consisting of H and F; $R^5$ is H; each $R^6$ is independently selected from the group consisting of H and $CH_3$; $X^1$—$X^2$—$X^3$ is C(O)—$CHR^8CHR^8$—COOH; and each $R^8$ is selected from the group consisting of H and $C_1$-$C_3$ alkyl, and where optionally 2 $R^8$ are taken together, along with the atoms to which they are attached, to form a 3- to 6-membered fused ring. In this aspect, all other groups are as provided in the general formula (Ia) above.

In aspects of this embodiment, 1e is selected from the group consisting of H, F, Cl, $C_1$-$C_3$ alkyl, and $C_1$-$C_3$ haloalkyl; $R^2$ is selected from the group consisting of halogen, $C_1$-$C_3$ alkyl, $C_1$-$C_3$ haloalkyl, $OC_1$-$C_3$ alkyl, $C_2$-$C_3$ alkenyl, and $N(R^6)_2$; $R^3$ is selected from the group consisting of halogen, $C_1$-$C_3$ alkyl, $C_1$-$C_3$ haloalkyl, $OC_1$-$C_3$ alkyl, $C_2$-$C_3$ alkenyl, and $N(R^6)_2$; $R^4$ is selected from the group consisting of H, F, Cl, $C_1$-$C_3$ alkyl, and $C_1$-$C_3$ haloalkyl; $R^5$ is selected from the group consisting of H, F, Cl, $OR^6$, $C_1$-$C_3$ alkyl, and $C_1$-$C_3$ haloalkyl; each $R^6$ is independently selected from the group consisting of H, $C_1$-$C_3$ alkyl, and $C_1$-$C_3$ haloalkyl; $X^1$—$X^2$—$X^3$ is selected from the group consisting of C(O)—$CH_2C(R^8)_2$—$COOR^6$, C(O)—$CH_2C(R)_2$—$SO_2R^6$, and C(O)—$CH_2C(R^8)_2$—$C(O)N(R^9)_2$; and each $R^8$ is selected from the group consisting of H, $C_1$-$C_3$ alkyl, $C_1$-$C_3$ alkyl substituted by OH, $C_1$-$C_3$ alkyl substituted by $OC_1$-$C_3$ alkyl, and $C_3$-$C_6$ cycloalkyl, and where optionally 2 $R^8$ are taken together, along with the atoms to which they are attached, to form a 3- to 6-membered spirocycle. In instances of this aspect, 1e is selected from the group consisting of H and F; $R^2$ is selected from the group consisting of Br, Cl, $CH_3$, $CH_2CH_3$, CH=$CH_2$, $OCH_3$, and $N(R^6)_2$; $R^3$ is selected from the group consisting of Br, Cl, $CH_3$, $CH_2CH_3$, CH=$CH_2$, $OCH_3$, and $N(R^6)_2$; $R^4$ is selected from the group consisting of H and F; $R^5$ is H; each $R^6$ is independently selected from the group consisting of H and $CH_3$; $X^1$—$X^2$—$X^3$ is C(O)—$CH_2C(R^8)_2$—COOH; and each $R^8$ is selected from the group consisting of H and $C_1$-$C_3$ alkyl, and where optionally 2 $R^8$ are taken together, along with the atoms to which they are attached, to form a 3- to 6-membered spirocycle. In this aspect, all other groups are as provided in the general formula (Ia) above.

An additional aspect of this embodiment relates to a pharmaceutical composition, said pharmaceutical composition comprising (a) a compound according to general formula (Ia) or aspects described above or a pharmaceutically acceptable salt thereof; and (b) a pharmaceutically acceptable carrier.

An additional aspect of this embodiment relates to methods of inducing an immune response in a subject, comprising administering a therapeutically effective amount of a compound according to general formula (Ia) or aspects described above or a pharmaceutically acceptable salt thereof to the subject.

An additional aspect of this embodiment relates to methods of inducing an immune response in a subject, comprising administering a therapeutically effective amount of a composition described above to the subject.

An additional aspect of this embodiment relates to methods of inducing a STING-dependent type I interferon production in a subject, comprising administering a therapeutically effective amount of a compound according to general formula (Ia) or aspects described above or a pharmaceutically acceptable salt thereof to the subject.

An additional aspect of this embodiment relates to methods of inducing STING-dependent type I interferon production in a subject, comprising administering a therapeutically effective amount of a composition described above to the subject.

An additional aspect of this embodiment relates to methods of inducing STING-dependent cytokine production in a subject, comprising administering a therapeutically effective amount of a compound according to general formula (Ia) or aspects described above or a pharmaceutically acceptable salt thereof to the subject.

An additional aspect of this embodiment relates to methods of inducing a STING-dependent cytokine production in a subject, comprising administering a therapeutically effective amount of a composition according described above to the subject.

In each embodiment described herein, variables $R^1$, $R^2$, $R^3$, $R^4$, $R^5$, $R^6$, $R^8$, $R^9$, $X^1$, $X^2$, and $X^3$ of general formula (Ia), and the various aspects and instances thereof, are each selected independently from each other, with the proviso that at least one of R', $R^2$, $R^3$, $R^4$, $R^5$, $R^6$, $R^8$, and $R^9$ is not H.

A second embodiment relates to compounds of general formula (Ib):

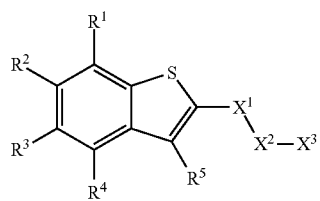

or a pharmaceutically acceptable salt thereof, wherein $R^1$ is selected from the group consisting of H, halogen, $OR^6$, $N(R^6)_2$, $C_1$-$C_6$ alkyl, $C_1$-$C_6$ haloalkyl, $C_1$-$C_6$ alkyl substituted by $OR^6$, $C_1$-$C_6$ alkyl substituted by $N(R^6)_2$, $COOR^6$, and $C(O)N(R^6)_2$; $R^2$ is selected from the group consisting of halogen, CN, $OR^6$, $N(R^6)_2$, $COOR^6$, $C(O)N(R^6)_2$, $SO_2R^6$, $C_1$-$C_6$ alkyl, $C_1$-$C_6$ haloalkyl, $C_1$-$C_6$ alkyl substituted by $OR^6$, $C_2$-$C_6$ alkenyl, $C_2$-$C_6$ haloalkenyl, $C_2$-$C_6$ alkenyl substituted by $OR^6$, $C_2$-$C_6$ alkynyl, $C_2$-$C_6$ haloalkynyl, $C_2$-$C_6$ alkynyl substituted by $OR^6$, $C_3$-$C_6$ cycloalkyl, and a 3- to 6-membered heterocyclic ring including 1 to 2 ring members selected from the group consisting of O, S, N, and $N(R^6)$; $R^3$ is selected from the group consisting of halogen, CN, $OR^6$, $N(R^6)_2$, $COOR^6$, $C(O)N(R^6)_2$, $SO_2R^6$, $C_1$-$C_6$ alkyl, $C_1$-$C_6$ haloalkyl, $C_1$-$C_6$ alkyl substituted by $OR^6$, $C_2$-$C_6$ alkenyl, $C_2$-$C_6$ haloalkenyl, $C_2$-$C_6$ alkenyl substituted by $OR^6$, $C_2$-$C_6$ alkynyl, $C_2$-$C_6$ haloalkynyl, $C_2$-$C_6$ alkynyl substituted by $OR^6$, $C_3$-$C_6$ cycloalkyl, and a 3- to 6-membered heterocyclic ring including 1 to 2 ring members selected from the group consisting of O, S, N, and $N(R^6)$; $R^4$ is selected from the group consisting of H, halogen, $OR^6$, $N(R^6)_2$, $C_1$-$C_6$ alkyl, $C_1$-$C_6$ haloalkyl, $C_1$-$C_6$ alkyl substituted by $OR^6$, $C_1$-$C_6$ alkyl substituted by $N(R^6)_2$, $COOR^6$, and $C(O)N(R^6)_2$; $R^5$ is selected from H, halogen, $OR^6$, $N(R^6)_2$, CN, $C_1$-$C_6$ alkyl, $C_1$-$C_6$ haloalkyl, $C_1$-$C_6$ alkyl substituted by $OR^6$, $COOR^6$, and $C(O)N(R^6)_2$; each $R^6$ is independently selected from the group consisting of H, $C_1$-$C_6$ alkyl, and $C_1$-$C_6$ haloalkyl; $X^1$ is $C(O)$; $X^2$ is $CH_2CHR^8$; each $R^8$ is independently selected from the group consisting of halogen, $C_1$-$C_6$ alkyl, CN, $OR^6$, $N(R^6)_2$, $C_1$-$C_6$ haloalkyl, $C_3$-$C_6$ cycloalkyl, $C_1$-$C_6$ alkyl substituted by $OR^6$, and $C_1$-$C_6$ alkyl substituted by $N(R^6)_2$; $X^3$ is selected from the group consisting of $COOR^6$, $C(O)SR^6$, $C(S)OR^6$, $SO_2R^6$, and $C(O)N(R^9)_2$; and each $R^9$ is independently selected from the group consisting of H, $COOR^6$, and $SO_2R^6$; wherein $X^1$—$X^2$—$X^3$ is $X^1$—$CH_2CHR^8$—$X^3$.

In aspects of this embodiment, le is selected from the group consisting of H, halogen, $OR^6$, $N(R^6)_2$, $C_1$-$C_6$ alkyl, $C_1$-$C_6$ haloalkyl, $C_1$-$C_6$ alkyl substituted by $OR^6$, $C_1$-$C_6$ alkyl substituted by $N(R^6)_2$, $COOR^6$, and $C(O)N(R^6)_2$. In instances of this aspect, le is selected from the group consisting of H, F, Cl, $C_1$-$C_3$ alkyl, and $C_1$-$C_3$ haloalkyl. In particular instances of this aspect, le is selected from the group consisting of H and F. In this aspect, all other groups are as provided in the general formula (Ib) above.

In aspects of this embodiment, $R^2$ is selected from the group consisting of halogen, CN, $OR^6$, $N(R^6)_2$, $COOR^6$, $C(O)N(R^6)_2$, $SO_2R^6$, $C_1$-$C_6$ alkyl, $C_1$-$C_6$ haloalkyl, $C_1$-$C_6$ alkyl substituted by $OR^6$, $C_2$-$C_6$ alkenyl, $C_2$-$C_6$ haloalkenyl, $C_2$-$C_6$ alkenyl substituted by $OR^6$, $C_2$-$C_6$ alkynyl, $C_2$-$C_6$ haloalkynyl, $C_2$-$C_6$ alkynyl substituted by $OR^6$, $C_3$-$C_6$ cycloalkyl, and a 3- to 6-membered heterocyclic ring including 1 to 2 ring members selected from the group consisting of O, S, N, and $N(R^6)$. In instances of this aspect, $R^2$ is selected from the group consisting of halogen, $C_1$-$C_3$ alkyl, $C_1$-$C_3$ haloalkyl, $OC_1$-$C_3$ alkyl, $C_2$-$C_3$ alkenyl, and $N(R^6)_2$. In particular instances of this aspect, $R^2$ is selected from the group consisting of Br, Cl, $CH_3$, $CH_2CH_3$, $CH=CH_2$, $OCH_3$, and $N(R^6)_2$. In this aspect, all other groups are as provided in the general formula (Ib) or aspects described above.

In aspects of this embodiment, $R^3$ is selected from the group consisting of halogen, CN, $OR^6$, $N(R^6)_2$, $COOR^6$, $C(O)N(R^6)_2$, $SO_2R^6$, $C_1$-$C_6$ alkyl, $C_1$-$C_6$ haloalkyl, $C_1$-$C_6$ alkyl substituted by $OR^6$, $C_2$-$C_6$ alkenyl, $C_2$-$C_6$ haloalkenyl, $C_2$-$C_6$ alkenyl substituted by $OR^6$, $C_2$-$C_6$ alkynyl, $C_2$-$C_6$ haloalkynyl, $C_2$-$C_6$ alkynyl substituted by $OR^6$, $C_3$-$C_6$ cycloalkyl, and a 3- to 6-membered heterocyclic ring including 1 to 2 ring members selected from the group consisting of O, S, N, and $N(R^6)$. In instances of this aspect, $R^3$ is selected from the group consisting of halogen, $C_1$-$C_3$ alkyl, $C_1$-$C_3$ haloalkyl, $OC_1$-$C_3$ alkyl, $C_2$-$C_3$ alkenyl, and $N(R^6)_2$. In particular instances of this aspect, $R^3$ is selected from the group consisting of Br, Cl, $CH_3$, $CH_2CH_3$, $CH=CH_2$, $OCH_3$, and $N(R^6)_2$. In this aspect, all other groups are as provided in the general formula (Ib) or aspects described above.

In aspects of this embodiment, $R^4$ is selected from the group consisting of H, halogen, $OR^6$, $N(R^6)_2$, $C_1$-$C_6$ alkyl, $C_1$-$C_6$ haloalkyl, $C_1$-$C_6$ alkyl substituted by $OR^6$, $C_1$-$C_6$ alkyl substituted by $N(R^6)_2$, $COOR^6$, and $C(O)N(R^6)_2$. In instances of this aspect, $R^4$ is selected from the group consisting of H, F, Cl, $C_1$-$C_3$ alkyl, and $C_1$-$C_3$ haloalkyl. In particular instances of this aspect, $R^4$ is selected from the group consisting of H and F. In this aspect, all other groups are as provided in the general formula (Ib) or aspects described above.

In aspects of this embodiment, $R^5$ is selected from the group consisting of H, halogen, $OR^6$, $N(R^6)_2$, CN, $C_1$-$C_6$ alkyl, $C_1$-$C_6$ haloalkyl, $C_1$-$C_6$ alkyl substituted by $OR^6$, $COOR^6$, and $C(O)N(R^6)_2$. In instances of this aspect, $R^5$ is selected from the group consisting of H, F, Cl, $C_1$-$C_3$ alkyl, and $C_1$-$C_3$ haloalkyl. In particular instances of this aspect, $R^5$ is H. In this aspect, all other groups are as provided in the general formula (Ib) or aspects described above.

In aspects of this embodiment, each $R^6$ is independently selected from the group consisting of H, $C_1$-$C_6$ alkyl, and $C_1$-$C_6$ haloalkyl. In instances of this aspect, each $R^6$ is independently selected from the group consisting of H, $C_1$-$C_3$ alkyl, and $C_1$-$C_3$ haloalkyl. In particular instances of this aspect, each $R^6$ is independently selected from the group consisting of H and $CH_3$. In this aspect, all other groups are as provided in the general formula (Ib) or aspects described above.

In aspects of this embodiment, $X^3$ is selected from the group consisting of $COOR^6$, $C(O)SR^6$, $C(S)OR^6$, $SO_2R^6$, and $C(O)N(R^9)_2$. In instances of this aspect, $X^3$ is selected from the group consisting of $COOR^6$, $SO_2R^6$, and $C(O)N(R^9)_2$. In particular instances of this aspect, $X^3$ is $COOR^6$. In even more particular instances of this aspect, $X^3$ is COOH. In this aspect, all other groups are as provided in the general formula (Ib) or aspects described above.

In aspects of this embodiment, each $R^9$ is independently selected from the group consisting of H, $COOR^6$, and $SO_2R^6$. In instances of this aspect, each $R^9$ is independently H. In this aspect, all other groups are as provided in the general formula (Ib) or aspects described above.

In aspects of this embodiment, $X^2$ is $CH_2CHR^8$, wherein each $R^8$ is independently selected from the group consisting of halogen, $C_1$-$C_6$ alkyl, CN, $OR^6$, $N(R^6)_2$, $C_1$-$C_6$ haloalkyl, $C_3$-$C_6$ cycloalkyl, $C_1$-$C_6$ alkyl substituted by $OR^6$, and $C_1$-$C_6$ alkyl substituted by $N(R^6)_2$. In instances of this aspect, $R^8$ is selected from the group consisting of $C_1$-$C_3$ alkyl, $C_1$-$C_3$ alkyl substituted by OH, $C_1$-$C_3$ alkyl substituted by $OC_1$-$C_3$ alkyl, and $C_3$-$C_6$ cycloalkyl. In particular instances, $R^8$ is selected from the group consisting of $CH_3$, $CH_2CH_3$, $CH_2CH_2CH_3$, $CH(CH_3)_2$, $CH_2OCH_3$, and cyclopropyl. In this aspect, all other groups are as provided in the general formula (Ib) or aspects described above.

In aspects of this embodiment, le is selected from the group consisting of H, F, Cl, $C_1$-$C_3$ alkyl, and $C_1$-$C_3$ haloalkyl; $R^2$ is selected from the group consisting of halogen, $C_1$-$C_3$ alkyl, $C_1$-$C_3$ haloalkyl, $OC_1$-$C_3$ alkyl, $C_2$-$C_3$ alkenyl, and $N(R^6)_2$; $R^3$ is selected from the group consisting of halogen, $C_1$-$C_3$ alkyl, $C_1$-$C_3$ haloalkyl, $OC_1$-$C_3$ alkyl, $C_2$-$C_3$ alkenyl, and $N(R^6)_2$; $R^4$ is selected from the group consisting of H, F, Cl, $C_1$-$C_3$ alkyl, and $C_1$-$C_3$ haloalkyl; $R^5$ is selected from the group consisting of H, F, Cl, $OR^6$, $C_1$-$C_3$ alkyl, and $C_1$-$C_3$ haloalkyl; each $R^6$ is independently selected from the group consisting of H, $C_1$-$C_3$ alkyl, and $C_1$-$C_3$ haloalkyl; $X^1$—$X^2$—$X^3$ is selected from the group consisting of C(O)—$CH_2CHR^8$—$COOR^6$, C(O)—$CH_2CHR^8$—$SO_2R^6$, and C(O)—$CH_2CHR^8$—$C(O)N(R^9)_2$; $R^8$ is selected from the group consisting of $C_1$-$C_3$ alkyl, $C_1$-$C_3$ alkyl substituted by OH, $C_1$-$C_3$ alkyl substituted by $OC_1$-$C_3$ alkyl, and $C_3$-$C_6$ cycloalkyl. In instances of this aspect, le is selected from the group consisting of H and F; $R^2$ is selected from the group consisting of Br, Cl, $CH_3$, $CH_2CH_3$, CH=$CH_2$, $OCH_3$, and $N(R^6)_2$; $R^3$ is selected from the group consisting of Br, Cl, $CH_3$, $CH_2CH_3$, CH=$CH_2$, $OCH_3$, and $N(R^6)_2$; $R^4$ is selected from the group consisting of H and F; $R^5$ is H; each $R^6$ is independently selected from the group consisting of H and $CH_3$; $X^1$—$X^2$—$X^3$ is C(O)—$CH_2CHR^8$—COOH; and $R^8$ is selected from the group consisting of $CH_3$, $CH_2CH_3$, $CH_2CH_2CH_3$, $CH(CH_3)_2$, $CH_2OCH_3$, and cyclopropyl. In this aspect, all other groups are as provided in the general formula (Ib) above.

An additional aspect of this embodiment relates to a pharmaceutical composition, said pharmaceutical composition comprising (a) a compound according to general formula (Ib) or aspects described above or a pharmaceutically acceptable salt thereof; and (b) a pharmaceutically acceptable carrier.

An additional aspect of this embodiment relates to methods of inducing an immune response in a subject, comprising administering a therapeutically effective amount of a compound according to general formula (Ib) or aspects described above or a pharmaceutically acceptable salt thereof to the subject.

An additional aspect of this embodiment relates to methods of inducing an immune response in a subject, comprising administering a therapeutically effective amount of a composition described above to the subject.

An additional aspect of this embodiment relates to methods of inducing a STING-dependent type I interferon production in a subject, comprising administering a therapeutically effective amount of a compound according to general formula (Ib) or aspects described above or a pharmaceutically acceptable salt thereof to the subject.

An additional aspect of this embodiment relates to methods of inducing a STING-dependent type I interferon production in a subject, comprising administering a therapeutically effective amount of a composition described above to the subject.

An additional aspect of this embodiment relates to methods of inducing STING-dependent cytokine production in a subject, comprising administering a therapeutically effective amount of a compound according to general formula (Ib) or aspects described above or a pharmaceutically acceptable salt thereof to the subject.

An additional aspect of this embodiment relates to methods of inducing STING-dependent cytokine production in a subject, comprising administering a therapeutically effective amount of a composition described above to the subject.

In each embodiment described herein, variables $R^1$, $R^2$, $R^3$, $R^4$, $R^5$, $R^6$, $R^8$, $R^9$, $X^1$, $X^2$, and $X^3$ of general formula (Ib), and the various aspects and instances thereof, are each selected independently from each other, with the proviso that at least one of R', $R^2$, $R^3$, $R^4$, $R^5$, $R^6$, $R^8$, and $R^9$ is not H.

Additional embodiments of this disclosure relate to uses of compounds of general formula (I), and pharmaceutically acceptable salts thereof. The compounds of general formula (I) may be useful as agents to induce immune responses, to induce STING-dependent type I interferon production, and/or to treat a cell proliferation disorder. In these embodiments, the compound of formula (I) is

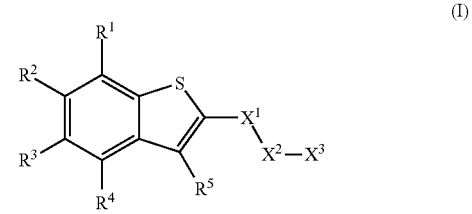

(I)

or a pharmaceutically acceptable salt thereof, wherein $R^1$ is selected from the group consisting of H, halogen, $OR^6$, $N(R^6)_2$, $C_1$-$C_6$ alkyl, $C_1$-$C_6$ haloalkyl, $C_1$-$C_6$ alkyl substituted by $OR^6$, $C_1$-$C_6$ alkyl substituted by $N(R^6)_2$, $COOR^6$, and $C(O)N(R^6)_2$; $R^2$ is selected from the group consisting of H, halogen, CN, $OR^6$, $N(R^6)_2$, $COOR^6$, $C(O)N(R^6)_2$, $SO_2R^6$, $C_1$-$C_6$ alkyl, $C_1$-$C_6$ haloalkyl, $C_1$-$C_6$ alkyl substituted by $OR^6$, $C_2$-$C_6$ alkenyl, $C_2$-$C_6$ haloalkenyl, $C_2$-$C_6$ alkenyl substituted by $OR^6$, $C_2$-$C_6$ alkynyl, $C_2$-$C_6$ haloalkynyl, $C_2$-$C_6$ alkynyl substituted by $OR^6$, $C_3$-$C_6$ cycloalkyl, and a 3- to 6-membered heterocyclic ring including 1 to 2 ring members selected from the group consisting of O, S, N, and $N(R^6)$; $R^3$ is selected from the group consisting of H, halogen, CN, $OR^6$, $N(R^6)_2$, $COOR^6$, $C(O)N(R^6)_2$, $SO_2R^6$, $C_1$-$C_6$ alkyl, $C_1$-$C_6$ haloalkyl, $C_1$-$C_6$ alkyl substituted by $OR^6$, $C_2$-$C_6$ alkenyl, $C_2$-$C_6$ haloalkenyl, $C_2$-$C_6$ alkenyl substituted by $OR^6$, $C_2$-$C_6$ alkynyl, $C_2$-$C_6$ haloalkynyl, $C_2$-$C_6$ alkynyl substituted by $OR^6$, $C_3$-$C_6$ cycloalkyl, and a 3- to 6-membered heterocyclic ring including 1 to 2 ring members selected from the group consisting of O, S, N, and $N(R^6)$; $R^4$ is selected from the group consisting of H, halogen, $OR^6$, $N(R^6)_2$, $C_1$-$C_6$ alkyl, $C_1$-$C_6$ haloalkyl, $C_1$-$C_6$ alkyl substituted by $OR^6$, $C_1$-$C_6$ alkyl substituted by $N(R^6)_2$, $COOR^6$, and $C(O)N(R^6)_2$; $R^5$ is selected from H, halogen, $OR^6$, $N(R^6)_2$, CN, $C_1$-$C_6$ alkyl, $C_1$-$C_6$ haloalkyl, $C_1$-$C_6$ alkyl substituted by $OR^6$, $COOR^6$, and $C(O)N(R^6)_2$; each $R^6$ is independently selected from the group consisting of H, $C_1$-$C_6$ alkyl, and $C_1$-$C_6$ haloalkyl; $X^1$ is C(O); $X^2$ is $(C(R^8)_2)_{(1-3)}$; each $R^8$ is independently selected from the group consisting of H, halogen, $C_1$-$C_6$ alkyl, CN, $OR^6$, $N(R^6)_2$, $C_1$-$C_6$ haloalkyl, $C_3$-$C_6$ cycloalkyl, $C_1$-$C_6$ alkyl substituted by $OR^6$, and $C_1$-$C_6$ alkyl substituted by $N(R^6)_2$; optionally 2 $R^8$ may be taken together, along with the atoms to which they are attached, to form a 3- to 6-membered fused ring; optionally 2 $R^8$ may be taken together, along with the atoms to which they are attached, to form a 3- to 6-membered spirocycle; $X^3$ is selected from the group consisting of $COOR^6$, $C(O)SR^6$, $C(S)OR^6$, $SO_2R^6$, and $C(O)N(R^9)_2$; and each $R^9$ is independently selected from the group consisting of H, $COOR^6$, and $SO_2R^6$.

An additional embodiment relates to methods of inducing an immune response in a subject, comprising administering a therapeutically effective amount of a compound of general formula (I) above or a pharmaceutically acceptable salt thereof to the subject.

An additional embodiment relates to methods of inducing an immune response in a subject, comprising administering a therapeutically effective amount of a composition comprising a compound of general formula (I) above or a pharmaceutically acceptable salt thereof to the subject.

An additional embodiment relates to methods of inducing STING-dependent type I interferon production in a subject, comprising administering a therapeutically effective amount of a compound of general formula (I) or a pharmaceutically acceptable salt thereof to the subject.

An additional embodiment relates to methods of inducing STING-dependent type I interferon production in a subject, comprising administering a therapeutically effective amount of a composition comprising a compound of general formula (I) above or a pharmaceutically acceptable salt thereof to the subject.

An additional embodiment relates to methods of inducing STING-dependent cytokine production in a subject, comprising administering a therapeutically effective amount of a compound of general formula (I) above or a pharmaceutically acceptable salt thereof to the subject.

An additional embodiment relates to methods of inducing STING-dependent cytokine production in a subject, comprising administering a therapeutically effective amount of a composition comprising a compound of general formula (I) above or a pharmaceutically acceptable salt thereof to the subject.

In each embodiment described herein, variables $R^1$, $R^2$, $R^3$, $R^4$, $R^5$, $R^6$, $R^8$, $R^9$, $X^1$, $X^2$, and $X^3$ of general formula (I), and the various aspects and instances thereof, are each selected independently from each other, with the proviso that at least one of $R^1$, $R^2$, $R^3$, $R^4$, $R^5$, $R^6$, $R^8$, and $R^9$ is not H.

An additional embodiment relates to a compound selected from the group consisting of

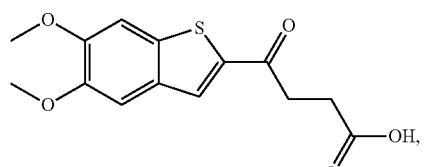

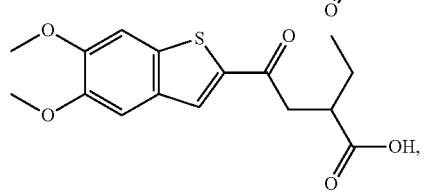

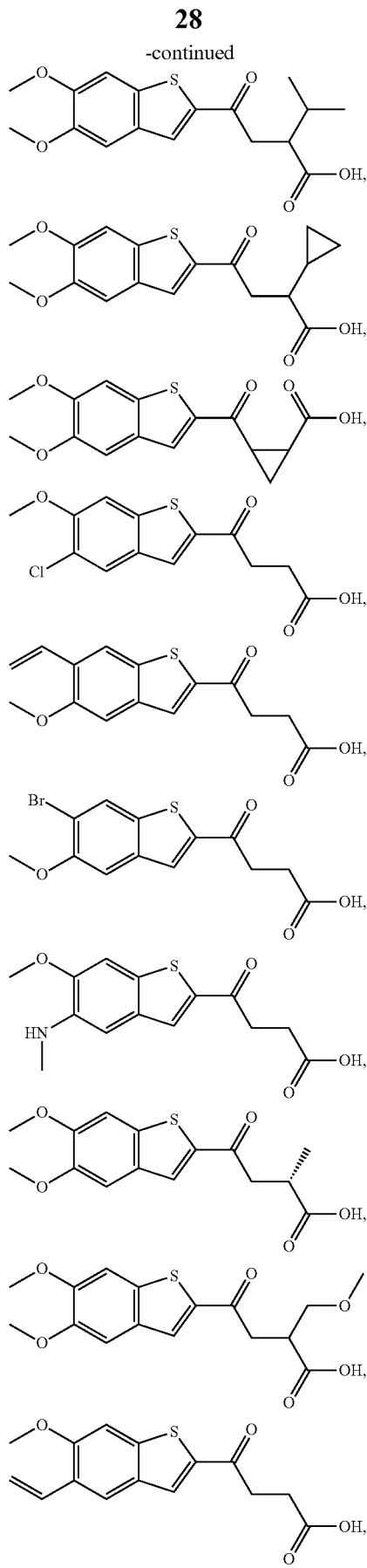

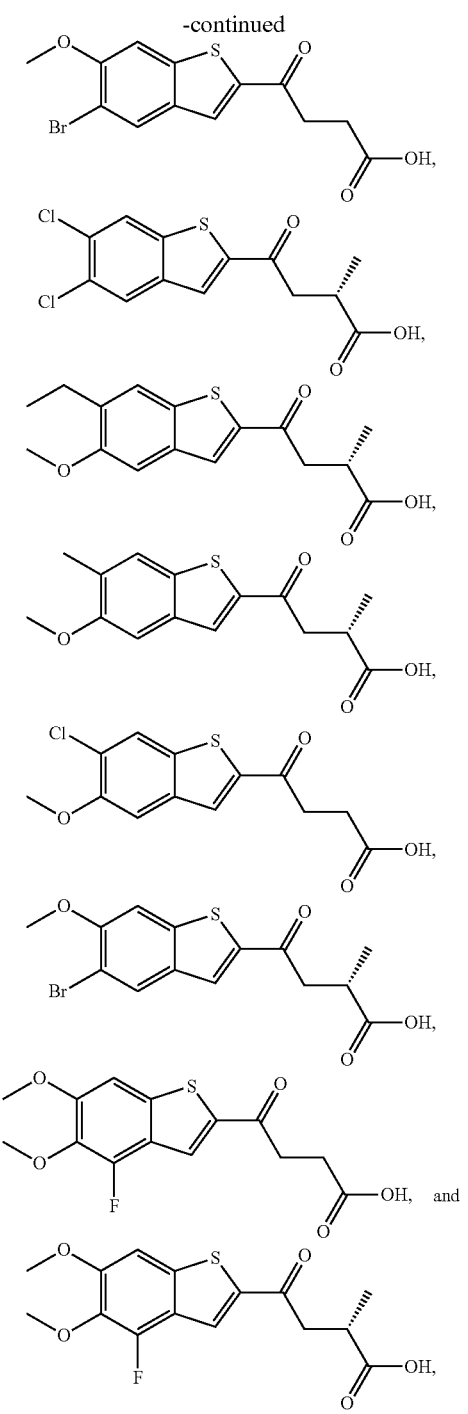
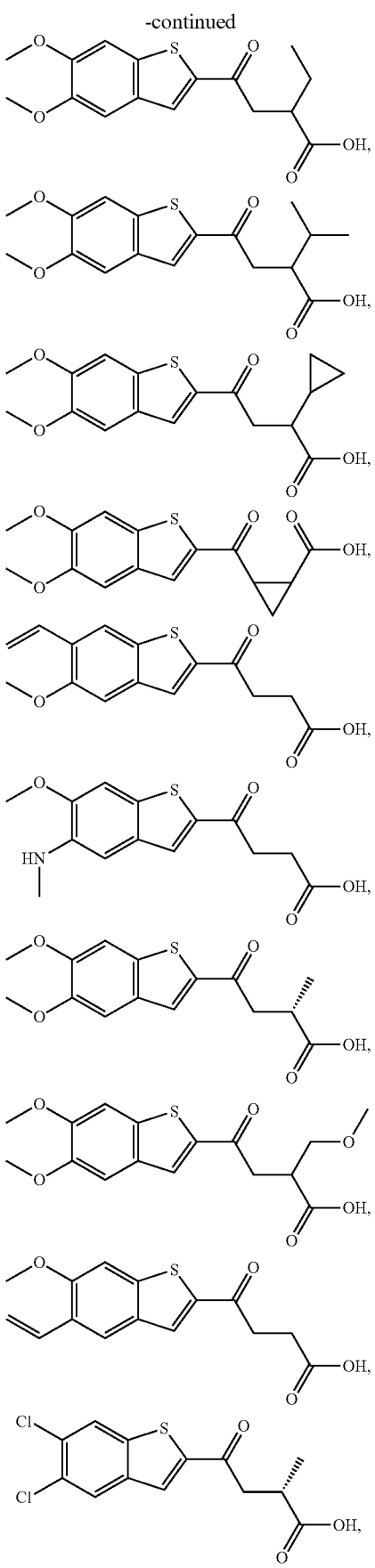
and pharmaceutically acceptable salts thereof. In aspects of this embodiment, the compound is selected from the group consisting of
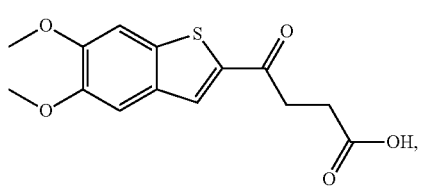

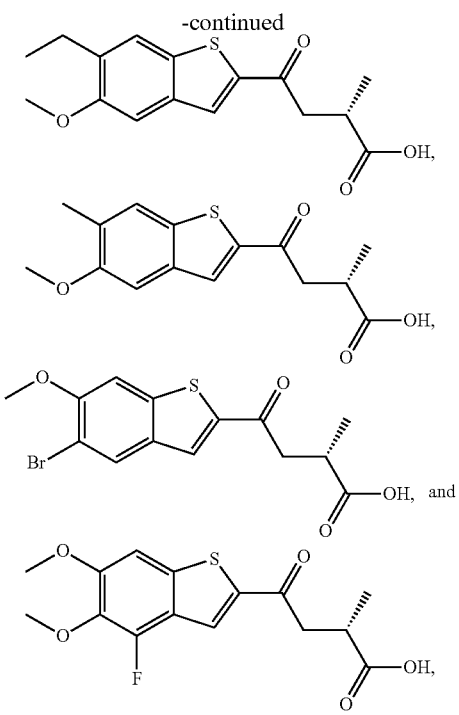

and pharmaceutically acceptable salts thereof.

Salts

As indicated above, the compounds of the present invention can be employed in the form of pharmaceutically acceptable salts. Those skilled in the art will recognize those instances in which the compounds of the invention may form salts. Examples of such compounds are described herein by reference to possible salts. Such reference is for illustration only. Pharmaceutically acceptable salts can be used with compounds for treating patients. Non-pharmaceutical salts may, however, be useful in the preparation of intermediate compounds.

The term "pharmaceutically acceptable salt" refers to a salt (including an inner salt such as a zwitterion) that possesses effectiveness similar to the parent compound and that is not biologically or otherwise undesirable (e.g., is neither toxic nor otherwise deleterious to the recipient thereof). Thus, an embodiment of the invention provides pharmaceutically acceptable salts of the compounds of the invention. The term "salt(s)", as employed herein, denotes any of the following: acidic salts formed with inorganic and/or organic acids, as well as basic salts formed with inorganic and/or organic bases. Salts of compounds of the invention may be formed by methods known to those of ordinary skill in the art, for example, by reacting a compound of the invention with an amount of acid or base, such as an equivalent amount, in a medium such as one in which the salt precipitates or in aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates ("mesylates"), naphthalenesulfonates, nitrates, oxalates, phosphates, propionates, salicylates, succinates, sulfates, tartarates, thiocyanates, toluenesulfonates (also known as tosylates) and the like. Suitable salts include acid addition salts that may, for example, be formed by mixing a solution of a compound with a solution of a pharmaceutically acceptable acid such as hydrochloric acid, sulfuric acid, acetic acid, trifluoroacetic acid, or benzoic acid. Additionally, acids that are generally considered suitable for the formation of pharmaceutically useful salts from basic pharmaceutical compounds are discussed, for example, by P. Stahl et al, Camille G. (eds.), *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in The Orange Book (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quaternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others. Compounds carrying an acidic moiety can be mixed with suitable pharmaceutically acceptable salts to provide, for example, alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

All such acid salts and base salts are intended to be pharmaceutically acceptable salts within the scope of the invention and all acid and base salts are considered equivalent to the free forms of the corresponding compounds for purposes of the invention.

In addition, when a compound of the invention contains both a basic moiety, such as, but not limited to an aliphatic primary, secondary, tertiary or cyclic amine, an aromatic or heteroaryl amine, pyridine or imidazole, and an acidic moiety, such as, but not limited to tetrazole or carboxylic acid, zwitterions ("inner salts") may be formed and are included within the terms "salt(s)" as used herein. It is understood that certain compounds of the invention may exist in zwitterionic form, having both anionic and cationic centers within the same compound and a net neutral charge. Such zwitterions are included within the invention.

Methods of Preparing Compounds

Several methods for preparing the compounds of general formula (Ia), the compounds of general formula (Ib), the compounds of general formula (I), and pharmaceutically acceptable salts of the foregoing, are described in the following Schemes and Examples. Starting materials and intermediates are purchased from commercial sources, made from known procedures, or are otherwise illustrated. In some cases the order of carrying out the steps of the reaction schemes may be varied to facilitate the reaction or to avoid unwanted reaction products.

In the following Methods and Schemes, LG represents a leaving group, which may be a halide or triflate group. The variables $R^2$, $R^3$, $R^4$, $R^6$, $R^8$, and $X^2$, have the same meaning as provided above.

Method 1

Benzo[b]thiophene 2-carboxylic acids are typically prepared from ortho-halo benzaldehydes. The sequence starts with treatment with an alpha-thio acetic acid ester under basic condition. Then, the ester in the resulting compound was cleaved to the carboxylic acid under basic condition to provide the desired substituted benzo[b]thiophene 2-carboxylic acid 1C.

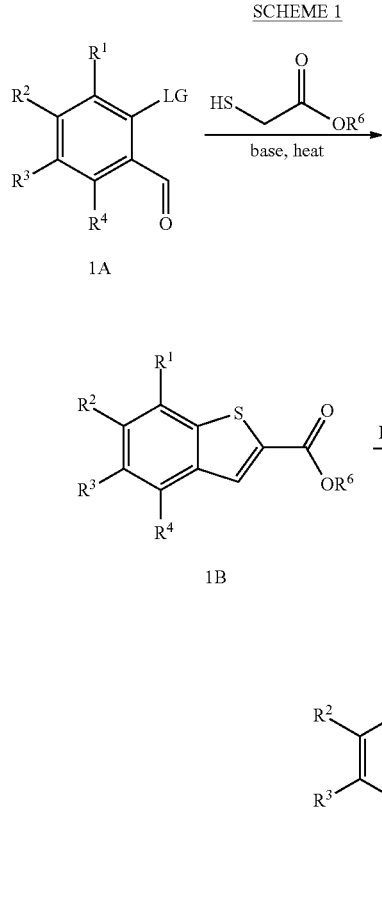

Method 2

One method for the preparation of the compounds of general formula (Ia), the compounds of general formula (Ib), the compounds of general formula (I), and pharmaceutically acceptable salts of the foregoing, is detailed in Scheme 2. The sequence starts with a benzo[b]thiophene substituted at the 2-position with an appropriate 1,3-dicarbonyl group, such as a beta-keto ester. It was reacted with an alpha-halo ester under basic condition to afford substitution at the 2 position of the alkyl chain. Then, both esters were hydrolyzed using either acidic or basic condition; upon further exposure to basic condition, the carboxylic acid corresponding to the ester in the starting material underwent decarboxylation to give the desired benzo[b]thiophene keto acid 2C.

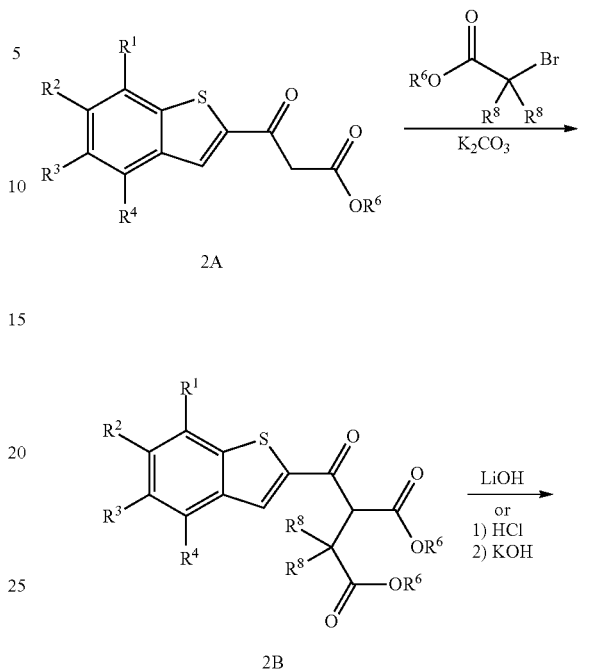

Method 3

Another method for the preparation of the compounds of general formula (Ia), the compounds of general formula (Ib), the compounds of general formula (I), and pharmaceutically acceptable salts of the foregoing, is detailed in Scheme 3. The sequence starts with a benzo[b]thiophene without substitution at the 2 position. It was treated with tert-butyllithium followed by a cyclic acid anhydride to give the desired 4-keto carboxylic acid product 3B.

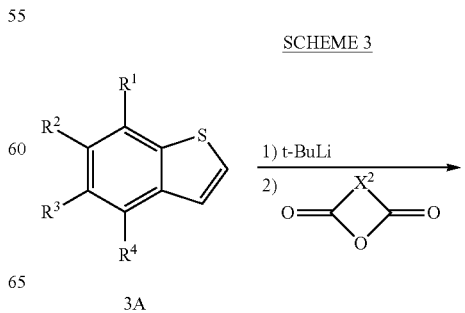

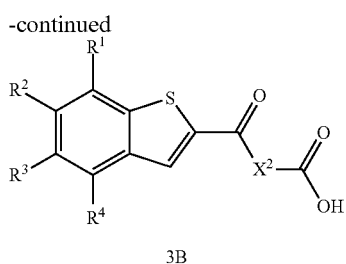

3B

Method 4

Another method for the preparation of the compounds of general formula (Ia), the compounds of general formula (Ib), the compounds of general formula (I), and pharmaceutically acceptable salts of the foregoing, is detailed in Scheme 4. The sequence starts with a benzo[b]thiophene substituted with a carboxylic acid at the 2 position. It was treated with oxalyl chloride/dichloromethane condition. The resulting acid chloride was reacted with an alkyl zinc reagent, typically containing an ester, using a transition metal such as copper or palladium to mediate the coupling. Then, the ester was cleaved under basic or acidic condition to provide the desired benzo[b]thiophene gamma-keto acid 4D.

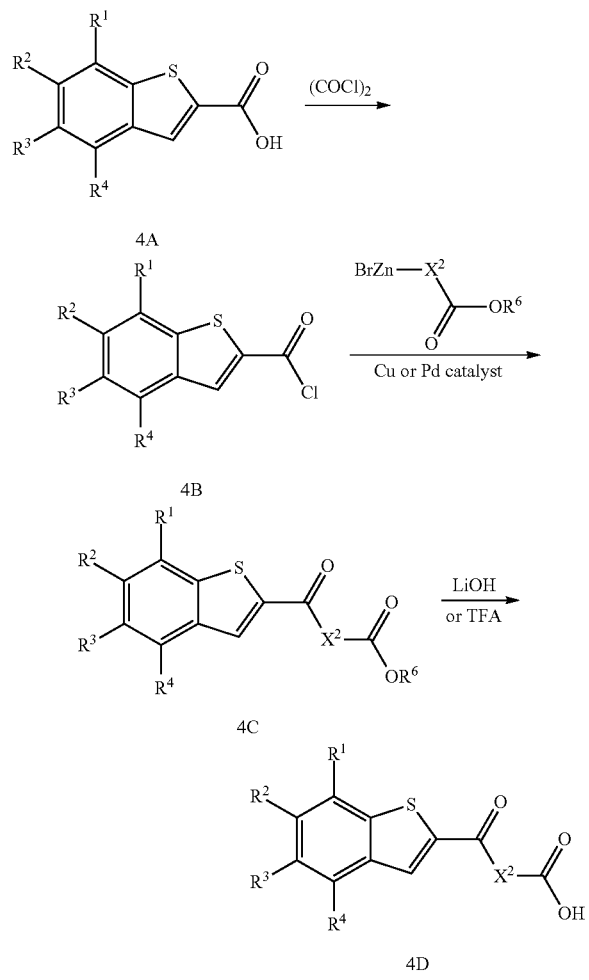

Method 5

Another method for the preparation of the compounds of general formula (Ia), the compounds of general formula (Ib), the compounds of general formula (I), and pharmaceutically acceptable salts of the foregoing, is detailed in Scheme 5. The sequence starts with a benzo[b]thiophene substituted at the 2 position with a gamma-keto ester and with a halide or triflate on the benzo[b]thiophene. It was treated with a boronic ester, acid, or trifluoroborate salt and a palladium catalyst under aqueous basic condition. Then the ester in the resulting compound was cleaved to the carboxylic acid under basic condition to provide the desired substituted benzo[b]thiophene 5C. The following scheme depicts introduction of the $R^2$ substituent, but this same general method couple bring in certain $R^3$ substituents as well when employing a related substrate with an appropriately placed LG.

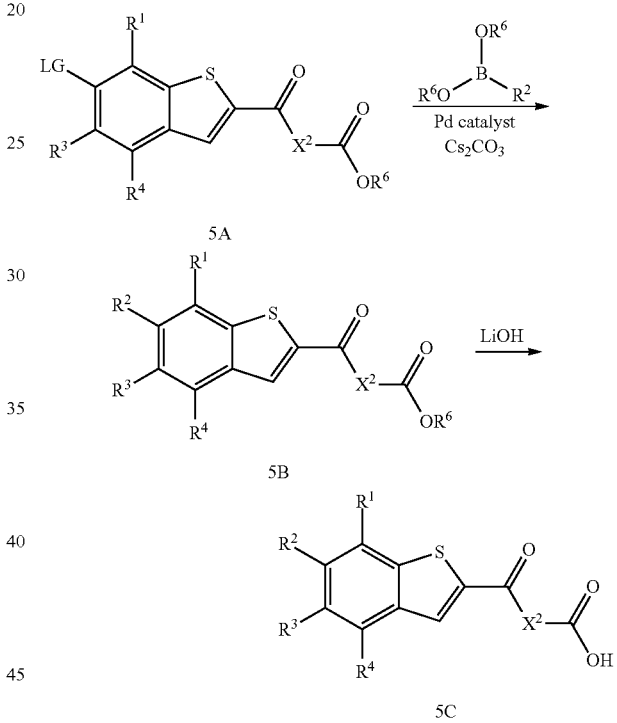

Administration

The present disclosure relates to methods of treating a cell-proliferation disorder, said method comprising administering to a subject in need thereof a combination therapy that comprises (a) a PD-1 antagonist; and (b) a benzo[b]thiophene STING agonist.

PD-1 antagonists may be provided by continuous infusion, or by doses administered, e.g., daily, 1-7 times per week, weekly, bi-weekly, monthly, bimonthly, quarterly, semiannually, annually etc. Doses may be provided, e.g., intravenously, subcutaneously, topically, orally, nasally, rectally, intramuscular, intracerebrally, intraspinally, or by inhalation. A total dose for a treatment interval is generally at least 0.05 µg/kg body weight, more generally at least 0.2 µg/kg, 0.5 µg/kg, 1 µg/kg, 10 ug/kg, 100 µg/kg, 0.25 mg/kg, 1.0 mg/kg, 2.0 mg/kg, 5.0 mg/ml, 10 mg/kg, 25 mg/kg, 50 mg/kg or more (see, e.g., Yang, et al. (2003) New Engl. J. Med. 349:427-434; Herold, et al. (2002) New Engl. J. Med. 346:1692-1698; Liu, et al. (1999) J. Neurol. Neurosurg.

Psych. 67:451-456; Portielji, et al. (20003) Cancer Immunol. Immunother. 52:133-144). Doses may also be provided to achieve a pre-determined target concentration of PD-1 antagonists in the subject's serum, such as 0.1, 0.3, 1, 3, 10, 30, 100, 300 µg/mL or more. In embodiments, the PD-1 antagonist is administered as a 200 mg dose once every 21 days. In other embodiments, PD-1 antagonists are administered subcutaneously or intravenously, on a weekly, biweekly, "every 4 weeks," monthly, bimonthly, or quarterly basis at 10, 20, 50, 80, 100, 200, 500, 1000 or 2500 mg/subject.

The benzo[b]thiophene STING agonists and a pharmaceutically acceptable carrier or excipient(s) will typically be formulated into a dosage form adapted for administration to a subject by a desired route of administration. For example, dosage forms include those adapted for (1) oral administration, such as tablets, capsules, caplets, pills, troches, powders, syrups, elixirs, suspensions, solutions, emulsions, sachets, and cachets; and (2) parenteral administration, such as sterile solutions, suspensions, and powders for reconstitution. Suitable pharmaceutically acceptable carriers or excipients will vary depending upon the particular dosage form chosen. In addition, suitable pharmaceutically acceptable carriers or excipients may be chosen for a particular function that they may serve in the composition. In embodiments, the benzo[b]thiophene STING agonist may be formulated into a dosage form that allows for systemic use, i.e., distribution of the benzo[b]thiophene STING agonist throughout the body of the subject; examples of such systemic administration include oral administration and intravenous administration. In additional embodiments, the benzo[b]thiophene STING agonist may be formulated into a dosage form that allows for targeted or isolated use, i.e., administration of the benzo[b]thiophene STING agonist only to the portion of the subject's body to be treated; examples of such targeted administration include intratumoral injection.

The benzo[b]thiophene STING agonist is administered once every 1 to 30 days. In embodiments, the benzo[b]thiophene STING agonist is administered once every 3 to 28 days. In particular embodiments, the benzo[b]thiophene STING agonist is administered once every 3, 7, 14, 21, or 28 days. In embodiments of such methods, the benzo[b]thiophene STING agonist is administered for from 2 to 36 months. In specific embodiments, the benzo[b]thiophene STING agonist is administered for up to 3 months. In additional embodiments of such methods, the benzo[b]thiophene STING agonist is administered once every 3, 7, 14, 21, or 28 days for from 2 to 36 months. In further embodiments, the benzo[b]thiophene STING agonist is administered once every 3, 7, 14, 21, or 28 days for up to 3 months. In specific embodiments, the benzo[b]thiophene STING agonist is administered once every 3, 7, 14, 21, or 28 days for up to 3 months, followed by a period, lasting at least 2 months, in which the time interval between doses is increased by at least two-fold. In more specific embodiments, the benzo[b]thiophene STING agonist is administered once every 3, 7, 14, 21, or 28 days for up to 3 months, followed by a period, lasting at least 2 months, in which the time interval between doses is increased by at least three-fold. For example, if the benzo[b]thiophene STING agonist is administered once every 7 days for up to 3 months, it may be followed by a period in which the benzo[b]thiophene STING agonist is administered once every 14 or 21 days for up to two years.

In some embodiments, at least one of the therapeutic agents (the PD-1 antagonist and the benzo[b]thiophene STING agonist) in the combination therapy is administered using the same dosage regimen (dose, frequency, and duration of treatment) that is typically employed when the agent is used as monotherapy for treating the same condition. In other embodiments, the patient receives a lower total amount of at least one of the therapeutic agents in the combination therapy than when the agent is used as monotherapy, e.g., smaller doses, less frequent doses, and/or shorter treatment duration.

A combination therapy of the invention may be used prior to or following surgery to remove a tumor and may be used prior to, during, or after radiation treatment.

In some embodiments, a combination therapy of the invention is administered to a patient who has not previously been treated with a biotherapeutic or chemotherapeutic agent, i.e., is treatment-naïve. In other embodiments, the combination therapy is administered to a patient who failed to achieve a sustained response after prior therapy with the biotherapeutic or chemotherapeutic agent, i.e., is treatment-experienced.

Thus, the present disclosure relates to methods of treating a cell-proliferation disorder, said method comprising administering to a subject in need thereof a combination therapy that comprises (a) a PD-1 antagonist; and (b) a benzo[b]thiophene STING agonist; wherein the PD-1 antagonist is administered once every 21 days; and the benzo[b]thiophene STING agonist is administered once every 1 to 30 days for 3 to 90 days, then optionally once every 1 to 30 days for up to 1050 days. In embodiments, the benzo[b]thiophene STING agonist is administered at least three times.

In specific embodiments, the benzo[b]thiophene STING agonist is administered once every 3 to 30 days for 9 to 90 days, then optionally once every 3 to 30 days for up to 1050 days. In specific embodiments, the benzo[b]thiophene STING agonist is administered once every 3 to 21 days for 9 to 63 days, then optionally once every 3 to 21 days for up to 735 days. In further specific embodiments, the benzo[b]thiophene STING agonist is administered once every 7 to 21 days for 21 to 63 days, then optionally once every 7 to 21 days for up to 735 days. In still further embodiments, the benzo[b]thiophene STING agonist is administered once every 7 to 10 days for 21 to 30 days, then optionally once every 21 days for up to 735 days. In still further embodiments, the benzo[b]thiophene STING agonist is administered once every 7 days for 21 days, then optionally once every 21 days for up to 735 days. In additional embodiments, the benzo[b]thiophene STING agonist is administered once every 21 days for 63 days, then optionally once every 21 days for up to 735 days. In specific embodiments of the foregoing, the benzo[b]thiophene STING agonist is administered at least three times.

In some embodiments, one or more optional "rest" periods, during which the benzo[b]thiophene STING agonist is not administered, may be included in the treatment period. In specific embodiments, the optional rest period may be for from 3 to 30 days, from 7 to 21 days, or from 7 to 14 days. Following the rest period, dosing of the benzo[b]thiophene STING agonist may be resumed as described above.

Cell-Proliferation Disorders

The combination therapies disclosed herein are potentially useful in treating diseases or disorders including, but not limited to, cell-proliferation disorders. Cell-proliferation disorders include, but are not limited to, cancers, benign papillomatosis, gestational trophoblastic diseases, and benign neoplastic diseases, such as skin papilloma (warts) and genital papilloma. The terms "cancer", "cancerous", or "malignant" refer to or describe the physiological condition in mammals that is typically characterized by unregulated cell growth. A variety of cancers where PD-L1 or PD-L2 are implicated, whether malignant or benign and whether primary or secondary, may be treated or prevented with a method provided by the disclosure. Particularly preferred cancers that may be treated in accordance with the present disclosure include those characterized by elevated expression of one or both of PD-L1 and PD-L2 in tested tissue samples.

In specific embodiments, the disease or disorder to be treated is a cell-proliferation disorder. In certain embodiments, the cell-proliferation disorder is cancer. In particular embodiments, the cancer is selected from brain and spinal cancers, cancers of the head and neck, leukemia and cancers of the blood, skin cancers, cancers of the reproductive system, cancers of the gastrointestinal system, liver and bile duct cancers, kidney and bladder cancers, bone cancers, lung cancers, malignant mesothelioma, sarcomas, lymphomas, glandular cancers, thyroid cancers, heart tumors, germ cell tumors, malignant neuroendocrine (carcinoid) tumors, midline tract cancers, and cancers of unknown primary (i.e., cancers in which a metastasized cancer is found but the original cancer site is not known). In particular embodiments, the cancer is present in an adult patient; in additional embodiments, the cancer is present in a pediatric patient. In particular embodiments, the cancer is AIDS-related.

In specific embodiments, the cancer is selected from brain and spinal cancers. In particular embodiments, the brain and spinal cancer is selected from the group consisting of anaplastic astrocytomas, glioblastomas, astrocytomas, and estheosioneuroblastomas (also known as olfactory blastomas). In particular embodiments, the brain cancer is selected from the group consisting of astrocytic tumor (e.g., pilocytic astrocytoma, subependymal giant-cell astrocytoma, diffuse astrocytoma, pleomorphic xanthoastrocytoma, anaplastic astrocytoma, astrocytoma, giant cell glioblastoma, glioblastoma, secondary glioblastoma, primary adult glioblastoma, and primary pediatric glioblastoma), oligodendroglial tumor (e.g., oligodendroglioma, and anaplastic oligodendroglioma), oligoastrocytic tumor (e.g., oligoastrocytoma, and anaplastic oligoastrocytoma), ependymoma (e.g., myxopapillary ependymoma, and anaplastic ependymoma); medulloblastoma, primitive neuroectodermal tumor, schwannoma, meningioma, atypical meningioma, anaplastic meningioma, pituitary adenoma, brain stem glioma, cerebellar astrocytoma, cerebral astorcytoma/malignant glioma, visual pathway and hypothalmic glioma, and primary central nervous system lymphoma. In specific instances of these embodiments, the brain cancer is selected from the group consisting of glioma, glioblastoma multiforme, paraganglioma, and suprantentorial primordial neuroectodermal tumors (sPNET).

In specific embodiments, the cancer is selected from cancers of the head and neck, including recurrent or metastatic head and neck squamous cell carcinoma (HNSCC), nasopharyngeal cancers, nasal cavity and paranasal sinus cancers, hypopharyngeal cancers, oral cavity cancers (e.g., squamous cell carcinomas, lymphomas, and sarcomas), lip cancers, oropharyngeal cancers, salivary gland tumors, cancers of the larynx (e.g., laryngeal squamous cell carcinomas, rhabdomyosarcomas), and cancers of the eye or ocular cancers. In particular embodiments, the ocular cancer is selected from the group consisting of intraocular melanoma and retinoblastoma.

In specific embodiments, the cancer is selected from leukemia and cancers of the blood. In particular embodiments, the cancer is selected from the group consisting of myeloproliferative neoplasms, myelodysplastic syndromes, myelodysplastic/myeloproliferative neoplasms, acute myeloid leukemia (AML), myelodysplastic syndrome (MDS), chronic myelogenous leukemia (CML), myeloproliferative neoplasm (MPN), post-MPN AML, post-MDS AML, del(5q)-associated high risk MDS or AML, blastphase chronic myelogenous leukemia, angioimmunoblastic lymphoma, acute lymphoblastic leukemia, Langerans cell histiocytosis, hairy cell leukemia, and plasma cell neoplasms including plasmacytomas and multiple myelomas. Leukemias referenced herein may be acute or chronic.

In specific embodiments, the cancer is selected from skin cancers. In particular embodiments, the skin cancer is selected from the group consisting of melanoma, squamous cell cancers, and basal cell cancers. In specific embodiments, the skin cancer is unresectable or metastatic melanoma.

In specific embodiments, the cancer is selected from cancers of the reproductive system. In particular embodiments, the cancer is selected from the group consisting of breast cancers, cervical cancers, vaginal cancers, ovarian cancers, endometrial cancers, prostate cancers, penile cancers, and testicular cancers. In specific instances of these embodiments, the cancer is a breast cancer selected from the group consisting of ductal carcinomas and phyllodes tumors. In specific instances of these embodiments, the breast cancer may be male breast cancer or female breast cancer. In more specific instances of these embodiments, the breast cancer is triple-negative breast cancer. In specific instances of these embodiments, the cancer is a cervical cancer selected from the group consisting of squamous cell carcinomas and adenocarcinomas. In specific instances of these embodiments, the cancer is an ovarian cancer selected from the group consisting of epithelial cancers.

In specific embodiments, the cancer is selected from cancers of the gastrointestinal system. In particular embodiments, the cancer is selected from the group consisting of esophageal cancers, gastric cancers (also known as stomach cancers), gastrointestinal carcinoid tumors, pancreatic cancers, gallbladder cancers, colorectal cancers, and anal cancer. In instances of these embodiments, the cancer is selected from the group consisting of esophageal squamous cell carcinomas, esophageal adenocarcinomas, gastric adenocarcinomas, gastrointestinal carcinoid tumors, gastrointestinal stromal tumors, gastric lymphomas, gastrointestinal lymphomas, solid pseudopapillary tumors of the pancreas, pancreatoblastoma, islet cell tumors, pancreatic carcinomas including acinar cell carcinomas and ductal adenocarcinomas, gallbladder adenocarcinomas, colorectal adenocarcinomas, and anal squamous cell carcinomas.

In specific embodiments, the cancer is selected from liver and bile duct cancers. In particular embodiments, the cancer is liver cancer (also known as hepatocellular carcinoma). In particular embodiments, the cancer is bile duct cancer (also known as cholangiocarcinoma); in instances of these embodiments, the bile duct cancer is selected from the group consisting of intrahepatic cholangiocarcinoma and extrahepatic cholangiocarcinoma.

In specific embodiments, the cancer is selected from kidney and bladder cancers. In particular embodiments, the cancer is a kidney cancer selected from the group consisting of renal cell cancer, Wilms tumors, and transitional cell cancers. In particular embodiments, the cancer is a bladder cancer selected from the group consisting of urothelial carcinoma (a transitional cell carcinoma), squamous cell carcinomas, and adenocarcinomas.

In specific embodiments, the cancer is selected from bone cancers. In particular embodiments, the bone cancer is selected from the group consisting of osteosarcoma, malignant fibrous histiocytoma of bone, Ewing sarcoma, chordoma (cancer of the bone along the spine).

In specific embodiments, the cancer is selected from lung cancers. In particular embodiments, the lung cancer is selected from the group consisting of non-small cell lung cancer, small cell lung cancers, bronchial tumors, and pleuropulmonary blastomas.

In specific embodiments, the cancer is selected from malignant mesothelioma. In particular embodiments, the cancer is selected from the group consisting of epithelial mesothelioma and sarcomatoids.

In specific embodiments, the cancer is selected from sarcomas. In particular embodiments, the sarcoma is selected from the group consisting of central chondrosarcoma, central and periosteal chondroma, fibrosarcoma, clear cell sarcoma of tendon sheaths, and Kaposi's sarcoma.

In specific embodiments, the cancer is selected from lymphomas. In particular embodiments, the cancer is selected from the group consisting of Hodgkin lymphoma (e.g., Reed-Sternberg cells), non-Hodgkin lymphoma (e.g., diffuse large B-cell lymphoma, follicular lymphoma, mycosis fungoides, Sezary syndrome, primary central nervous system lymphoma), cutaneous T-cell lymphomas, primary central nervous system lymphomas.

In specific embodiments, the cancer is selected from glandular cancers. In particular embodiments, the cancer is selected from the group consisting of adrenocortical cancer (also known as adrenocortical carcinoma or adrenal cortical carcinoma), pheochromocytomas, paragangliomas, pituitary tumors, thymoma, and thymic carcinomas.

In specific embodiments, the cancer is selected from thyroid cancers. In particular embodiments, the thyroid cancer is selected from the group consisting of medullary thyroid carcinomas, papillary thyroid carcinomas, and follicular thyroid carcinomas.

In specific embodiments, the cancer is selected from germ cell tumors. In particular embodiments, the cancer is selected from the group consisting of malignant extracranial germ cell tumors and malignant extragonadal germ cell tumors. In specific instances of these embodiments, the malignant extragonadal germ cell tumors are selected from the group consisting of nonseminomas and seminomas.

In specific embodiments, the cancer is selected from heart tumors. In particular embodiments, the heart tumor is selected from the group consisting of malignant teratoma, lymphoma, rhabdomyosacroma, angiosarcoma, chondrosarcoma, infantile fibrosarcoma, and synovial sarcoma.

In specific embodiments, the cell-proliferation disorder is selected from benign papillomatosis, benign neoplastic diseases and gestational trophoblastic diseases. In particular embodiments, the benign neoplastic disease is selected from skin papilloma (warts) and genital papilloma. In particular embodiments, the gestational trophoblastic disease is selected from the group consisting of hydatidiform moles, and gestational trophoblastic neoplasia (e.g., invasive moles, choriocarcinomas, placental-site trophoblastic tumors, and epithelioid trophoblastic tumors).

In embodiments, the cell-proliferation disorder is a cancer that has metastasized, for example, a liver metastases from colorectal cancer.

In embodiments, the cell-proliferation disorder is selected from the group consisting of solid tumors and lymphomas. In particular embodiments, the cell-proliferation disorder is selected from the group consisting of advanced or metastatic solid tumors and lymphomas. In more particular embodiments, the cell-proliferation disorder is selected from the group consisting of malignant melanoma, head and neck squamous cell carcminoma, breast adenocarcinoma, and lymphomas. In aspects of such embodiments, the lymphomas are selected from the group consisting of diffuse large B-cell lymphoma, follicular lymphoma, mantle cell lymphoma, small lymphocytic lymphoma, mediastinal large B-cell lymphoma, splenic marginal zone B-cell lymphoma, extranodal marginal zone B-cell lymphoma of mucosa-associated lymphoid tissue (malt), nodal marginal zone B-cell lymphoma, lymphoplasmacytic lymphoma, primary effusion lymphoma, Burkitt lymphoma, anaplastic large cell lymphoma (primary cutaneous type), anaplastic large cell lymphoma (systemic type), peripheral T-cell lymphoma, angioimmunoblastic T-cell lymphoma, adult T-cell lymphoma/leukemia, nasal type extranodal NK/T-cell lymphoma, enteropathy-associated T-cell lymphoma, gamma/delta hepatosplenic T-cell lymphoma, subcutaneous panniculitis-like T-cell lymphoma, mycosis fungoides, and Hodgkin lymphoma.

In particular embodiments, the cell-proliferation disorder is classified as stage III cancer or stage IV cancer. In instances of these embodiments, the cancer is not surgically resectable.

Methods, Uses, and Medicaments

Products provided as therapeutic combinations may include a composition comprising a PD-1 antagonist and a benzo[b]thiophene STING agonist together in the same pharmaceutical composition, or may include a composition comprising a PD-1 antagonist, and a composition comprising a benzo[b]thiophene STING agonist in separate form, e.g. in the form of a kit or in any form designed to enable separate administration either concurrently or on separate dosing schedules.

The combination therapy may also comprise one or more additional therapeutic agents. The additional therapeutic agent may be, e.g., a chemotherapeutic, a biotherapeutic agent (including but not limited to antibodies to VEGF, VEGFR, EGFR, Her2/neu, other growth factor receptors, CD20, CD40, CD-40L, CTLA-4, OX-40, 4-1BB, and ICOS), an immunogenic agent (for example, attenuated cancerous cells, tumor antigens, antigen presenting cells such as dendritic cells pulsed with tumor derived antigen or nucleic acids, immune stimulating cytokines (for example, IL-2, IFNα2, GM-CSF), and cells transfected with genes encoding immune stimulating cytokines such as but not limited to GM-CSF). The one or more additional active agents may be co-administered either with the PD-1 antagonist or with the benzo[b]thiophene STING agonist. The additional active agent(s) may be administered in a single dosage form with one or more co-administered agent selected from the PD-1 antagonist and the benzo[b]thiophene STING agonist, or the additional active agent(s) may be administered in separate dosage form(s) from the dosage forms containing the PD-1 antagonist and/or the benzo[b]thiophene STING agonist.

The therapeutic combination disclosed herein may be used in combination with one or more other active agents, including but not limited to, other anti-cancer agents that are used in the prevention, treatment, control, amelioration, or reduction of risk of a particular disease or condition (e.g., cell-proliferation disorders). In one embodiment, a compound disclosed herein is combined with one or more other anti-cancer agents for use in the prevention, treatment, control amelioration, or reduction of risk of a particular disease or condition for which the compounds disclosed herein are useful. Such other active agents may be administered, by a route and in an amount commonly used therefor, contemporaneously or sequentially with a compound of the present disclosure.

The additional active agent(s) may be one or more agents selected from the group consisting of STING agonists, anti-viral compounds, antigens, adjuvants, anti-cancer agents, CTLA-4, LAG-3 and PD-1 pathway antagonists, lipids, liposomes, peptides, cytotoxic agents, chemotherapeutic agents, immunomodulatory cell lines, checkpoint inhibitors, vascular endothelial growth factor (VEGF) receptor inhibitors, topoisomerase II inhibitors, smoothen inhibitors, alkylating agents, anti-tumor antibiotics, anti-metabolites, retinoids, and immunomodulatory agents including but not limited to anti-cancer vaccines. It will be understood the descriptions of the above additional active agents may be overlapping. It will also be understood that the treatment combinations are subject to optimization, and it is understood that the best combination to use of the PD-1 antagonist and/or the benzo[b]thiophene STING agonist, and one or more additional active agents will be determined based on the individual patient needs.

When the therapeutic combination disclosed herein is used contemporaneously with one or more other active agents, the PD-1 antagonist and/or the benzo[b]thiophene STING agonist may be administered either simultaneously with, or before or after, one or more other active agent(s). Either of the PD-1 antagonist and/or the benzo[b]thiophene STING agonist may be administered separately, by the same or different route of administration, or together in the same pharmaceutical composition as the other agent(s).

The weight ratio of the PD-1 antagonist to the benzo[b]thiophene STING agonist may be varied and will depend upon the therapeutically effective dose of each agent. Generally, a therapeutically effective dose of each will be used. Combinations including at least one PD-1 antagonist, at least one benzo[b]thiophene STING agonist, and other active agents will generally include a therapeutically effective dose of each active agent. In such combinations, the PD-1 antagonist and/or the benzo[b]thiophene STING agonist disclosed herein and other active agents may be administered separately or in conjunction. In addition, the administration of one element may be prior to, concurrent with, or subsequent to the administration of other agent(s).

In one embodiment, this disclosure provides a PD-1 antagonist and/or a benzo[b]thiophene STING agonist, and at least one other active agent as a combined preparation for simultaneous, separate or sequential use in therapy. In one embodiment, the therapy is the treatment of a cell-proliferation disorder, such as cancer.

In one embodiment, the disclosure provides a kit comprising two or more separate pharmaceutical compositions, one of which contains a PD-1 antagonist and another of which contains a benzo[b]thiophene STING agonist. In one embodiment, the kit comprises means for separately retaining said compositions, such as a container, divided bottle, or divided foil packet. A kit of this disclosure may be used for administration of different dosage forms, for example, oral and parenteral, for administration of the separate compositions at different dosage intervals, or for titration of the separate compositions against one another. To assist with compliance, a kit of the disclosure typically comprises directions for administration.

The disclosure also provides the use of a benzo[b]thiophene STING agonist for treating a cell-proliferation disorder, where the patient has previously (e.g., within 24 hours) been treated with a PD-1 antagonist. The disclosure also provides the use of a PD-1 antagonist for treating a cell-proliferation disorder, where the patient has previously (e.g., within 24 hours) been treated with a benzo[b]thiophene STING agonist.

Anti-viral compounds that may be used in combination with the therapeutic combinations disclosed herein include hepatitis B virus (HBV) inhibitors, hepatitis C virus (HCV) protease inhibitors, HCV polymerase inhibitors, HCV NS4A inhibitors, HCV NS5A inhibitors, HCV NS5b inhibitors, and human immunodeficiency virus (HIV) inhibitors.

Antigens and adjuvants that may be used in combination with the therapeutic combinations disclosed herein include B7 costimulatory molecule, interleukin-2, interferon-γ, GM-CSF, CTLA-4 antagonists, OX-40/OX-40 ligand, CD40/CD40 ligand, sargramostim, levamisol, vaccinia virus, Bacille Calmette-Guerin (BCG), liposomes, alum, Freund's complete or incomplete adjuvant, detoxified endotoxins, mineral oils, surface active substances such as lipolecithin, pluronic polyols, polyanions, peptides, and oil or hydrocarbon emulsions. Adjuvants, such as aluminum hydroxide or aluminum phosphate, can be added to increase the ability of the vaccine to trigger, enhance, or prolong an immune response. Additional materials, such as cytokines, chemokines, and bacterial nucleic acid sequences, like CpG, a toll-like receptor (TLR) 9 agonist as well as additional agonists for TLR 2, TLR 4, TLR 5, TLR 7, TLR 8, TLR9, including lipoprotein, lipopolysaccharide (LPS), monophosphoryllipid A, lipoteichoic acid, imiquimod, resiquimod, and in addition retinoic acid-inducible gene I (RIG-I) agonists such as poly I:C, used separately or in combination are also potential adjuvants.

Examples of cytotoxic agents that may be used in combination with the therapeutic combinations disclosed herein include, but are not limited to, arsenic trioxide (sold under the tradename TRISENOX®), asparaginase (also known as L-asparaginase, and Erwinia L-asparaginase, sold under the tradenames ELSPAR® and KIDROLASE®).

Chemotherapeutic agents that may be used in combination with the therapeutic combinations disclosed herein include abiraterone acetate, altretamine, anhydrovinblastine, auristatin, bexarotene, bicalutamide, BMS 184476, 2,3,4,5,6-pentafluoro-N-(3-fluoro-4-methoxyphenyl)benzene sulfonamide, bleomycin, N,N-dimethyl-L-valyl-L-valyl-N-methyl-L-valyl-L-prolyl-1-Lproline-t-butylamide, cachectin, cemadotin, chlorambucil, cyclophosphamide, 3',4'-didehydro-4'deoxy-8'-norvin-caleukoblastine, docetaxol, doxetaxel, cyclophosphamide, carboplatin, carmustine, cisplatin, cryptophycin, cyclophosphamide, cytarabine, dacarbazine (DTIC), dactinomycin, daunorubicin, decitabine dolastatin, doxorubicin (adriamycin), etoposide, 5-fluorouracil, finasteride, flutamide, hydroxyurea and hydroxyurea andtaxanes, ifosfamide, liarozole, lonidamine, lomustine (CCNU), MDV3100, mechlorethamine (nitrogen mustard), melphalan, mivobulin isethionate, rhizoxin, sertenef, streptozocin, mitomycin, methotrexate, taxanes, nilutamide, nivolumab, onapristone, paclitaxel, pembrolizumab, prednimustine, procarbazine, RPR109881, stramustine phosphate, tamoxifen, tasonermin, taxol, tretinoin, vinblastine, vincristine, vindesine sulfate, and vinflunine, and pharmaceutically acceptable salts thereof.

Examples of vascular endothelial growth factor (VEGF) receptor inhibitors include, but are not limited to, bevacizumab (sold under the trademark AVASTIN by Genentech/Roche), axitinib (described in PCT International Patent Publication No. WO01/002369), Brivanib Alaninate ((S)—((R)-1-(4-(4-Fluoro-2-methyl-1H-indol-5-yloxy)-5-methylpyrrolo[2,1-f][1,2,4]triazin-6-yloxy)propan-2-yl)2-aminopropanoate, also known as BMS-582664), motesanib (N-

(2,3-dihydro-3,3-dimethyl-1H-indol-6-yl)-2-[(4-pyridinylmethyl)amino]-3-pyridinecarboxamide. and described in PCT International Patent Application Publication No. WO02/068470), pasireotide (also known as SO 230, and described in PCT International Patent Publication No. WO02/010192), and sorafenib (sold under the tradename NEXAVAR).

Examples of topoisomerase II inhibitors, include but are not limited to, etoposide (also known as VP-16 and Etoposide phosphate, sold under the tradenames TOPOSAR, VEPESID, and ETOPOPHOS), and teniposide (also known as VM-26, sold under the tradename VUMON).

Examples of alkylating agents, include but are not limited to, 5-azacytidine (sold under the trade name VIDAZA), decitabine (sold under the trade name of DECOGEN), temozolomide (sold under the trade names TEMODAR and TEMODAL), dactinomycin (also known as actinomycin-D and sold under the tradename COSMEGEN), melphalan (also known as L-PAM, L-sarcolysin, and phenylalanine mustard, sold under the tradename ALKERAN), altretamine (also known as hexamethylmelamine (HMM), sold under the tradename HEXALEN), carmustine (sold under the tradename BCNU), bendamustine (sold under the tradename TREANDA), busulfan (sold under the tradenames BUSULFEX® and MYLERAN®), carboplatin (sold under the tradename PARAPLATIN®), lomustine (also known as CCNU, sold under the tradename CEENU®), cisplatin (also known as CDDP, sold under the tradenames PLATINOL® and PLATINOL®-AQ), chlorambucil (sold under the tradename LEUKERAN®), cyclophosphamide (sold under the tradenames CYTOXAN® and NEOSAR®), dacarbazine (also known as DTIC, DIC and imidazole carboxamide, sold under the tradename DTIC-DOME®), altretamine (also known as hexamethylmelamine (HMM) sold under the tradename HEXALEN®), ifosfamide (sold under the tradename IFEX®), procarbazine (sold under the tradename MATULANE®), mechlorethamine (also known as nitrogen mustard, mustine and mechloroethamine hydrochloride, sold under the tradename MUSTARGEN®), streptozocin (sold under the tradename ZANOSAR®), thiotepa (also known as thiophosphoamide, TESPA and TSPA, and sold under the tradename THIOPLEX®, and pharmaceutically acceptable salts thereof.

Examples of anti-tumor antibiotics include, but are not limited to, doxorubicin (sold under the tradenames ADRIAMYCIN® and RUBEX®, bleomycin (sold under the tradename LENOXANE®), daunorubicin (also known as dauorubicin hydrochloride, daunomycin, and rubidomycin hydrochloride, sold under the tradename CERUBIDINE®), daunorubicin liposomal (daunorubicin citrate liposome, sold under the tradename DAUNOXOME®, mitoxantrone (also known as DHAD, sold under the tradename NOVANTRONE®), epirubicin (sold under the tradename ELLENCE™), idarubicin (sold under the tradenames IDAMYCIN®, IDAMYCIN®, PFS®), and mitomycin C (sold under the tradename MUTAMYCIN®).

Examples of anti-metabolites include, but are not limited to, claribine (2-chlorodeoxyadenosine, sold under the tradename LEUSTATIN®), 5-fluorouracil (sold under the tradename ADRUCIL®), 6-thioguanine (sold under the tradename PURINETHOL®), pemetrexed (sold under the tradename ALIMTA®), cytarabine (also known as arabinosylcytosine (Ara-C), sold under the tradename CYROSAR-U®), cytarabine liposomal (also known as Liposomal Ara-C, sold under the tradename DEPOCYT™), decitabine (sold under the tradename DACOGEN®), hydroxyurea and (sold under the tradenames HYDREA®, DROXIA™ and MYLOCEL™) fludarabine (sold under the tradename FLUDARA®), floxuridine (sold under the tradename FUDR®), cladribine (also known as 2-chlorodeoxyadenosine (2-CdA) sold under the tradename LEUSTATIN™), methotrexate (also known as amethopterin, methotrexate sodium (MTX), sold under the tradenames RHEUMATREX® and TREXALL™), and pentostatin (sold under the tradename NIPENT®).

Examples of retinoids include, but are not limited to, alitretinoin (sold under the tradename PANRETIN®), tretinoin (all-trans retinoic acid, also known as ATRA, sold under the tradename VESANOID®), Isotretinoin (13-c/s-retinoic acid, sold under the tradenames ACCUTANE®, AMNESTEEM®, CLARAVIS®, CLARUS®, DECUTAN®, ISOTANE®, IZOTECH®, ORATANE®, ISOTRET®, and SOTRET®), and bexarotene (sold under the tradename TARGRETIN®).

Additional Embodiments

The present disclosure further relates to methods of treating a cell-proliferation disorder, said method comprising administering to a subject in need thereof a combination therapy that comprises (a) a PD-1 antagonist; and (b) a benzo[b]thiophene STING agonist; wherein the PD-1 antagonist is administered once every 21 days; and the benzo[b]thiophene STING agonist is administered once every 1 to 30 days. In embodiments, the benzo[b]thiophene STING agonist is administered once every 3 to 28 days. In particular embodiments, the benzo[b]thiophene STING agonist is administered once every 3, 7, 14, 21, or 28 days.

In embodiments of such methods, the benzo[b]thiophene STING agonist is administered for from 2 to 36 months. In specific embodiments, the benzo[b]thiophene STING agonist is administered for up to 3 months.

In additional embodiments of such methods, the benzo[b]thiophene STING agonist is administered once every 3, 7, 14, 21, or 28 days for from 2 to 36 months. In further embodiments, the benzo[b]thiophene STING agonist is administered once every 3, 7, 14, 21, or 28 days for up to 3 months. In specific embodiments, the benzo[b]thiophene STING agonist is administered once every 3, 7, 14, 21, or 28 days for up to 3 months, followed by a period, lasting at least 2 months, in which the time interval between doses is increased by at least two-fold. In more specific embodiments, the benzo[b]thiophene STING agonist is administered once every 3, 7, 14, 21, or 28 days for up to 3 months, followed by a period, lasting at least 2 months, in which the time interval between doses is increased by at least three-fold. For example, if the benzo[b]thiophene STING agonist is administered once every 7 days for up to 3 months, it may be followed by a period in which the benzo[b]thiophene STING agonist is administered once every 14 or 21 days for up to two years.

The present disclosure further relates to methods of treating a cell-proliferation disorder, said method comprising administering to a subject in need thereof a combination therapy that comprises (a) a PD-1 antagonist; and (b) a benzo[b]thiophene STING agonist; wherein the PD-1 antagonist is administered once every 21 days; and the benzo[b]thiophene STING agonist is administered once every 1 to 30 days for 3 to 90 days, then optionally once every 1 to 30 days for up to 1050 days. In embodiments, the benzo[b]thiophene STING agonist is administered at least three times.

In specific embodiments, the benzo[b]thiophene STING agonist is administered once every 3 to 30 days for 9 to 90 days, then optionally once every 3 to 30 days for up to 1050 days. In specific embodiments, the benzo[b]thiophene STING agonist is administered once every 3 to 21 days for 9 to 63 days, then optionally once every 3 to 21 days for up to 735 days. In further specific embodiments, the benzo[b]thiophene STING agonist is administered once every 7 to 21 days for 21 to 63 days, then optionally once every 7 to 21 days for up to 735 days. In still further embodiments, the benzo[b]thiophene STING agonist is administered once every 7 to 10 days for 21 to 30 days, then optionally once every 21 days for up to 735 days. In still further embodiments, the benzo[b]thiophene STING agonist is administered once every 7 days for 21 days, then optionally once every 21 days for up to 735 days. In additional embodiments, the benzo[b]thiophene STING agonist is administered once every 21 days for 63 days, then optionally once every 21 days for up to 735 days. In specific embodiments of the foregoing, the benzo[b]thiophene STING agonist is administered at least three times.

Additionally, the present disclosure relates to methods of treating a cell-proliferation disorder, said method comprising administering to a subject in need thereof a combination therapy that comprises (a) a PD-1 antagonist; and (b) a benzo[b]thiophene STING agonist; wherein the cell-proliferation disorder is cancer. In specific embodiments, the cancer occurs as one or more solid tumors or lymphomas. In further specific embodiments, the cancer is selected from the group consisting of advanced or metastatic solid tumors and lymphomas. In still further specific embodiments, the cancer is selected from the group consisting of malignant melanoma, head and neck squamous cell carcinoma, breast adenocarcinoma, and lymphomas. In additional embodiments, the lymphoma is selected from the group consisting of diffuse large B-cell lymphoma, follicular lymphoma, mantle cell lymphoma, small lymphocytic lymphoma, mediastinal large B-cell lymphoma, splenic marginal zone B-cell lymphoma, extranodal marginal zone B-cell lymphoma of mucosa-associated lymphoid tissue (malt), nodal marginal zone B-cell lymphoma, lymphoplasmacytic lymphoma, primary effusion lymphoma, Burkitt lymphoma, anaplastic large cell lymphoma (primary cutaneous type), anaplastic large cell lymphoma (systemic type), peripheral T-cell lymphoma, angioimmunoblastic T-cell lymphoma, adult T-cell lymphoma/leukemia, nasal type extranodal NK/T-cell lymphoma, enteropathy-associated T-cell lymphoma, gamma/delta hepatosplenic T-cell lymphoma, subcutaneous panniculitis-like T-cell lymphoma, mycosis fungoides, and Hodgkin lymphoma. In particular embodiments, the cell-proliferation disorder is a cancer that has metastasized, for example, a liver metastases from colorectal cancer. In additional embodiments, the cell-proliferation disorder is a cancer is classified as stage III cancer or stage IV cancer. In instances of these embodiments, the cancer is not surgically resectable.

In embodiments of the methods disclosed herein, the PD-1 antagonist is an anti-PD-1 monoclonal antibody. In particular aspects of these embodiments, the PD-1 antagonist is selected from the group consisting of nivolumab, pembrolizumab, pidilizumab, and AMP-224. In specific aspects of these embodiments, the PD-1 antagonist is selected from nivolumab and pembrolizumab. In a more specific aspect, the PD-1 antagonist is nivolumab. In a further specific aspect, the PD-1 antagonist is pembrolizumab.

In embodiments of the methods disclosed herein, the benzo[b]thiophene STING agonist is selected from compounds of formula (Ia):

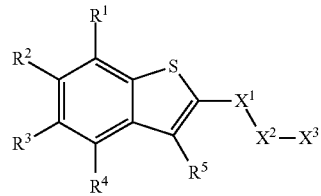

or a pharmaceutically acceptable salt thereof, wherein $R^1$ is selected from the group consisting of H, halogen, $OR^6$, $N(R^6)_2$, $C_1$-$C_6$ alkyl, $C_1$-$C_6$ haloalkyl, $C_1$-$C_6$ alkyl substituted by $OR^6$, $C_1$-$C_6$ alkyl substituted by $N(R^6)_2$, $COOR^6$, and $C(O)N(R^6)_2$; $R^2$ is selected from the group consisting of halogen, CN, $OR^6$, $N(R^6)_2$, $COOR^6$, $C(O)N(R^6)_2$, $SO_2R^6$, $C_1$-$C_6$ alkyl, $C_1$-$C_6$ haloalkyl, $C_1$-$C_6$ alkyl substituted by $OR^6$, $C_2$-$C_6$ alkenyl, $C_2$-$C_6$ haloalkenyl, $C_2$-$C_6$ alkenyl substituted by $OR^6$, $C_2$-$C_6$ alkynyl, $C_2$-$C_6$ haloalkynyl, $C_2$-$C_6$ alkynyl substituted by $OR^6$, $C_3$-$C_6$ cycloalkyl, and a 3- to 6-membered heterocyclic ring including 1 to 2 ring members selected from the group consisting of O, S, N, and $N(R^6)$; $R^3$ is selected from the group consisting of halogen, CN, $OR^6$, $N(R^6)_2$, $COOR^6$, $C(O)N(R^6)_2$, $SO_2R^6$, $C_1$-$C_6$ alkyl, $C_1$-$C_6$ haloalkyl, $C_1$-$C_6$ alkyl substituted by $OR^6$, $C_2$-$C_6$ alkenyl, $C_2$-$C_6$ haloalkenyl, $C_2$-$C_6$ alkenyl substituted by $OR^6$, $C_2$-$C_6$ alkynyl, $C_2$-$C_6$ haloalkynyl, $C_2$-$C_6$ alkynyl substituted by $OR^6$, $C_3$-$C_6$ cycloalkyl, and a 3- to 6-membered heterocyclic ring including 1 to 2 ring members selected from the group consisting of O, S, N, and $N(R^6)$; $R^4$ is selected from the group consisting of H, halogen, $OR^6$, $N(R^6)_2$, $C_1$-$C_6$ alkyl, $C_1$-$C_6$ haloalkyl, $C_1$-$C_6$ alkyl substituted by $OR^6$, $C_1$-$C_6$ alkyl substituted by $N(R^6)_2$, $COOR^6$, and $C(O)N(R^6)_2$; $R^5$ is selected from H, halogen, $OR^6$, $N(R^6)_2$, CN, $C_1$-$C_6$ alkyl, $C_1$-$C_6$ haloalkyl, $C_1$-$C_6$ alkyl substituted by $OR^6$, $COOR^6$, and $C(O)N(R^6)_2$; each $R^6$ is independently selected from the group consisting of H, $C_1$-$C_6$ alkyl, and $C_1$-$C_6$ haloalkyl; $X^1$ is C(O); $X^2$ is $(C(R^8)_2)_{(1-3)}$; each $R^8$ is independently selected from the group consisting of H, halogen, $C_1$-$C_6$ alkyl, CN, $OR^6$, $N(R^6)_2$, $C_1$-$C_6$ haloalkyl, $C_3$-$C_6$ cycloalkyl, $C_1$-$C_6$ alkyl substituted by $OR^6$, and $C_1$-$C_6$ alkyl substituted by $N(R^6)_2$; optionally 2 $R^8$ may be taken together, along with the atoms to which they are attached, to form a 3- to 6-membered fused ring; optionally 2 $R^8$ may be taken together, along with the atoms to which they are attached, to form a 3- to 6-membered spirocycle; $X^3$ is selected from the group consisting of $COOR^6$, $C(O)SR^6$, $C(S)OR^6$, $SO_2R^6$, and $C(O)N(R^9)_2$; and each $R^9$ is independently selected from the group consisting of H, $COOR^6$, and $SO_2R^6$; wherein when $X^1$—$X^2$—$X^3$ is $X^1$—$CHR^8$—$X^3$ or $X^1$—$CHR^8CH_2$—$X^3$, and at least one of $R^2$ and $R^3$ is not selected from the group consisting of halogen, $OR^6$, $C_1$-$C_6$ alkyl, and $C_1$-$C_6$ haloalkyl.

In instances of these embodiments, the benzo[b]thiophene STING agonist is selected from the group consisting of:

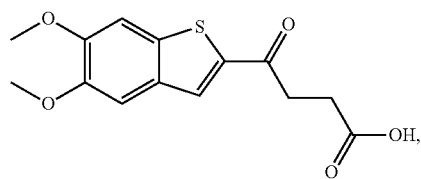

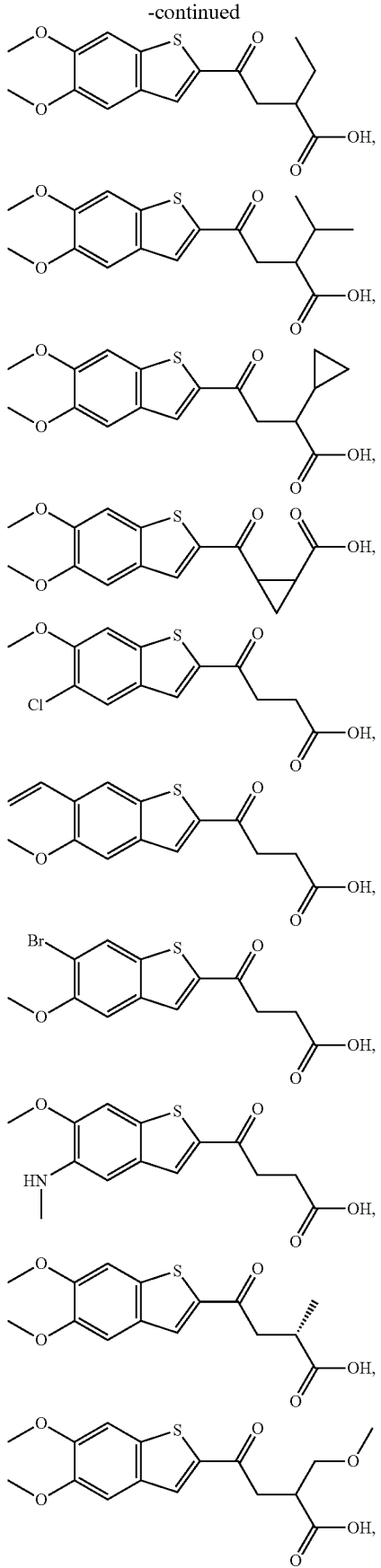
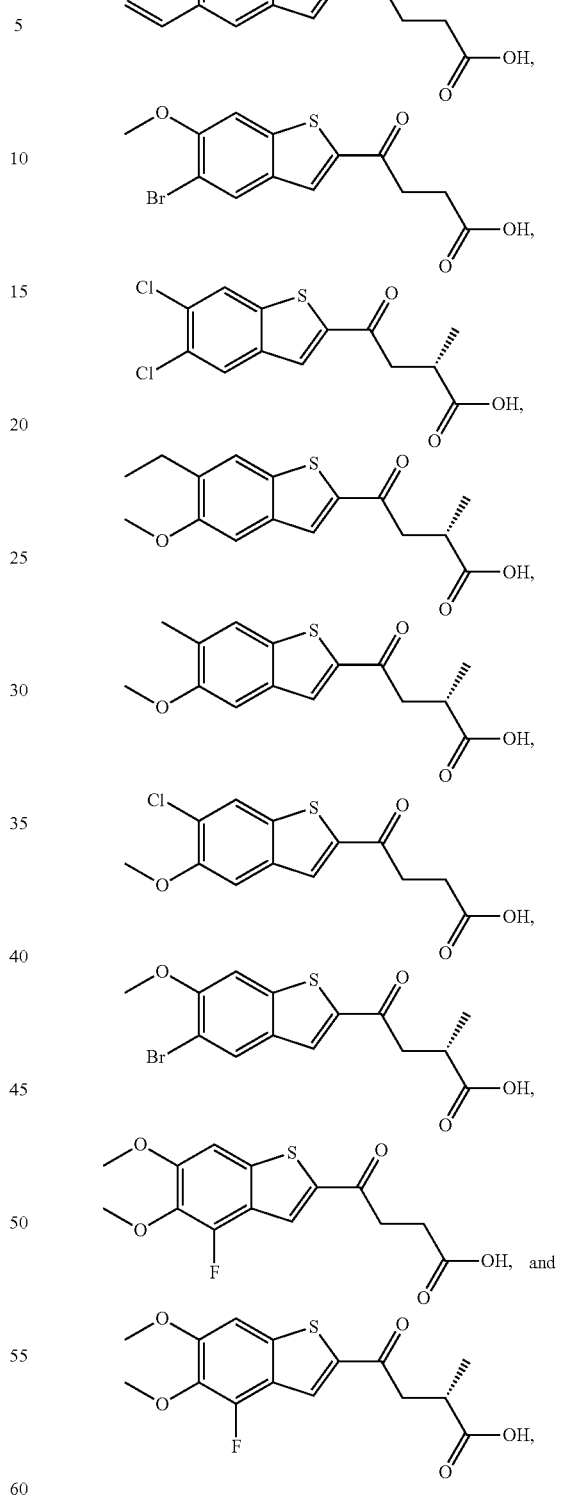
and pharmaceutically acceptable salts thereof.
In embodiments of the methods disclosed herein, the PD-1 antagonist is administered by intravenous infusion, and the benzo[b]thiophene STING agonist is orally, by intravenous infusion, by intertumoral injection, or by subcutaneous injection.

In embodiments of the methods disclosed herein, the PD-1 antagonist is administered prior to administration of the benzo[b]thiophene STING agonist. In alternative embodiments of the methods disclosed herein, the benzo[b]thiophene STING agonist is administered prior to administration of the PD-1 antagonist.

In embodiments of the methods disclosed herein, the PD-1 antagonist is administered at a dose of 200 mg; and the benzo[b]thiophene STING agonist is administered at a dose of from 10 µg to 3000 µg. In aspects of such embodiments, the benzo[b]thiophene STING agonist is administered at a dose of from 10 µg to 270 µg.

Additional embodiments of the disclosure include the pharmaceutical compositions, combinations, uses and methods set forth in above, wherein it is to be understood that each embodiment may be combined with one or more other embodiments, to the extent that such a combination is consistent with the description of the embodiments. It is further to be understood that the embodiments provided above are understood to include all embodiments, including such embodiments as result from combinations of embodiments.

General Methods

Standard methods in molecular biology are described Sambrook, Fritsch and Maniatis (1982 & 1989 $2^{nd}$ Edition, 2001 $3^{rd}$ Edition) *Molecular Cloning, A Laboratory Manual*, Cold Spring Harbor Laboratory Press, Cold Spring Harbor, N.Y.; Sambrook and Russell (2001) *Molecular Cloning*, $3^{rd}$ ed., Cold Spring Harbor Laboratory Press, Cold Spring Harbor, N.Y.; Wu (1993) *Recombinant DNA*, Vol. 217, Academic Press, San Diego, Calif.). Standard methods also appear in Ausbel, et al. (2001) *Current Protocols in Molecular Biology*, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science, Vol. 1*, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science, Vol. 2*, John Wiley and Sons, Inc., New York; Ausubel, et al. (2001) *Current Protocols in Molecular Biology, Vol. 3*, John Wiley and Sons, Inc., NY, NY, pp. 16.0.5-16.22.17; Sigma-Aldrich, Co. (2001) *Products for Life Science Research*, St. Louis, Mo.; pp. 45-89; Amersham Pharmacia Biotech (2001) BioDirectory, Piscataway, N.J., pp. 384-391). Production, purification, and fragmentation of polyclonal and monoclonal antibodies are described (Coligan, et al. (2001) *Current Protocols in Immunology, Vol. 1*, John Wiley and Sons, Inc., New York; Harlow and Lane (1999) *Using Antibodies*, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) *Current Protocols in Immunology, Vol. 4*, John Wiley, Inc., New York).

Monoclonal, polyclonal, and humanized antibodies can be prepared (see, e.g., Sheperd and Dean (eds.) (2000) *Monoclonal Antibodies*, Oxford Univ. Press, New York, N.Y.; Kontermann and Dubel (eds.) (2001) *Antibody Engineering*, Springer-Verlag, New York; Harlow and Lane (1988) *Antibodies A Laboratory Manual*, Cold Spring Harbor Laboratory Press, Cold Spring Harbor, N.Y., pp. 139-243; Carpenter, et al. (2000) *J. Immunol*. 165:6205; He, et al. (1998) *J. Immunol*. 160:1029; Tang et al. (1999) *J. Biol. Chem*. 274:27371-27378; Baca et al. (1997) *J. Biol. Chem*. 272:10678-10684; Chothia et al. (1989) *Nature* 342:877-883; Foote and Winter (1992) *J. Mol. Biol*. 224:487-499; U.S. Pat. No. 6,329,511).

An alternative to humanization is to use human antibody libraries displayed on phage or human antibody libraries in transgenic mice (Vaughan et al. (1996) *Nature Biotechnol*. 14:309-314; Barbas (1995) *Nature Medicine* 1:837-839; Mendez et al. (1997) *Nature Genetics* 15:146-156; Hoogenboom and Chames (2000) *Immunol. Today* 21:371-377; Barbas et al. (2001) *Phage Display: A Laboratory Manual*, Cold Spring Harbor Laboratory Press, Cold Spring Harbor, N.Y.; Kay et al. (1996) *Phage Display of Peptides and Proteins: A Laboratory Manual*, Academic Press, San Diego, Calif.; de Bruin et al. (1999) *Nature Biotechnol*. 17:397-399).

Purification of antigen is not necessary for the generation of antibodies. Animals can be immunized with cells bearing the antigen of interest. Splenocytes can then be isolated from the immunized animals, and the splenocytes can fused with a myeloma cell line to produce a hybridoma (see, e.g., Meyaard et al. (1997) *Immunity* 7:283-290; Wright et al. (2000) *Immunity* 13:233-242; Preston et al., supra; Kaithamana et al. (1999) *J. Immunol*. 163:5157-5164).

Methods for flow cytometry, including fluorescence activated cell sorting (FACS), are available (see, e.g., Owens, et al. (1994) *Flow Cytometry Principles for Clinical Laboratory Practice*, John Wiley and Sons, Hoboken, N.J.; Givan (2001) *Flow Cytometry*, $2^{nd}$ ed.; Wiley-Liss, Hoboken, N.J.; Shapiro (2003) *Practical Flow Cytometry*, John Wiley and Sons, Hoboken, N.J.). Fluorescent reagents suitable for modifying nucleic acids, including nucleic acid primers and probes, polypeptides, and antibodies, for use, e.g., as diagnostic reagents, are available (Molecular Probesy (2003) *Catalogue*, Molecular Probes, Inc., Eugene, Oreg.; Sigma-Aldrich (2003) *Catalogue*, St. Louis, Mo.).

Standard methods of histology of the immune system are described (see, e.g., Muller-Harmelink (ed.) (1986) *Human Thymus: Histopathology and Pathology*, Springer Verlag, New York, N.Y.; Hiatt, et al. (2000) *Color Atlas of Histology*, Lippincott, Williams, and Wilkins, Phila, Pa.; Louis, et al. (2002) *Basic Histology: Text and Atlas*, McGraw-Hill, New York, N.Y.).

Software packages and databases for determining, e.g., antigenic fragments, leader sequences, protein folding, functional domains, glycosylation sites, and sequence alignments, are available (see, e.g., GenBank, Vector NTI® Suite (Informax, Inc., Bethesda, Md.); GCG Wisconsin Package (Accelrys, Inc., San Diego, Calif.); DeCypher® (TimeLogic Corp., Crystal Bay, Nev.); Menne, et al. (2000) *Bioinformatics* 16: 741-742; Menne, et al. (2000) *Bioinformatics Applications Note* 16:741-742; Wren, et al. (2002) *Comput. Methods Programs Biomed*. 68:177-181; von Heijne (1983) *Eur. J. Biochem*. 133:17-21; von Heijne (1986) *Nucleic Acids Res*. 14:4683-4690).

The benzo[b]thiophene STING agonists of the disclosure may be prepared according to the methods disclosed in Provisional U.S. Patent Application No. 62/404,062, filed Oct. 4, 2016.

Advanced MC38 Mouse Syngenic Tumor Model

Synergistic tumor models are recognized to be appropriate models to evaluate anti-tumor efficacy of agents that target specific molecules, pathways, or cell types and to provide mechanistic rationale that targeting similar specific molecules, pathways, or cell types in human tumors will lead to favorable clinical outcomes. The mouse syngeneic MC38 tumor model is a mouse colon adenocarcinoma cell line that was established by carcinogenic induction of tumors in the C57BL/6 background. This cell line is considered immunogenic and is responsive to immune modulation. It is generally injected subcutaneously (SC) to evaluate tumor growth and response to treatment. Specifically, each animal is inoculated in the right lower flank with a SC dose of 1×10$^6$ MC38 colon adenocarcinoma cells in 100 µL of serum-free Dulbecco's modified Eagle's medium. Tumor progression is monitored by measuring tumor volume using Vernier calipers. See T. H. Corbett et al., *Tumor Induction Relationships in Development of Transplantable Cancers of the Colon in Mice for Chemotherapy Assays, with a Note on Carcinogen Structure*, 35(9) Cancer Res. 2434-2439 (Sep. 1, 1975).

Anti-Mouse PD-1 Antibody

In the Example below, the anti-tumor effects of selected benzo[b]thiophene STING agonists in combination with an anti-mouse PD1 antibody are evaluated in mouse syngeneic tumor models. Anti-tumor activity (tumor growth inhibition, tumor regression) is observed on treatment of mouse syngeneic tumors with the combination. Both mouse and human tumor infiltrating T cells express high levels of PD-1, associated with what is referred to as an "exhausted phenotype" (See Y. Jiang et al., "T-cell exhaustion in the tumor microenvironment", *Cell Death and Disease* 2015, 6, e1792). Induction of anti-tumor efficacy in mouse syngeneic tumor models following treatment with anti-mouse PD-1 antibodies provides a mechanistic rationale that treatment of cancer patients with anti-human PD-1 antibodies will induce anti-tumor efficacy (See S. Hu-Lieskovan et al., "Improved antitumor activity of immunotherapy with BRAF and MEK inhibitors in BRAF(V600E) melanoma", *Sci. Transl. Med.* 2015 Mar. 18; 7(279):279ra41; C. D. Pham et al., "Differential immune microenvironments and response to immune checkpoint blockade among molecular subtypes of murine medulloblastoma", *Clin. Cancer Res.* 2016 Feb. 1; 22(3):582-595; S. Budhu et al., "The importance of animal models in tumor immunity and immunotherapy", *Curr. Opin. Genet. Dev.* 2014, 24, 46-51). Suitable anti-mouse PD-1 antibodies that may be used include muDX400 (Merck), InVivoMAb and InVivoPlusMAb anti-mouse PD-1 clone J43 (commercially available from BioXCell as catalog number BE0033-2), InVivoMAb anti-mouse PD-1 clone 29F.1A12 (commercially available from BioXCell as catalog number BE0273), and InVivoMAb and InVivoPlusMAb anti-mouse PD-1 clone RMP1-14 (commercially available from BioXCell as catalog number BE0146).

Examples

Example 1: Anti-Tumor Efficacy of a Benzo[b]Thiophene STING Agonist in Combination with an Anti-PD-1 Antibody in Advanced MC38 Mouse Syngenic Tumor Model To assess the combination anti-tumor efficacy of a benzo[b]thiophene STING agonist and anti-mouse PD-1 antibody muDX400 in the advanced MC38 mouse syngeneic tumor model, a cohort of 8-12 week old female C57Bl/6 mice are implanted with 1×10$^6$ MC38 cells. When the tumors reach a median size of approximately 350 mm$^3$, the animals are randomized into 6 treatment groups of 10 mice per group:

Treatment Group A: PBS and mIgG1 (5 mg/kg)
Treatment Group B: PBS and anti-PD-1 antibody muDX400 (5 mg/kg)
Treatment Group C: benzo[b]thiophene STING agonist (5 µg) and mIgG1 (5 mg/kg)
Treatment Group D: benzo[b]thiophene STING agonist (5 µg) and anti-PD-1 antibody muDX400 (5 mg/kg)

Benzo[b]thiophene STING agonist is administered intratumorally on every 3 to 7 days for up to 30 days. Antibodies are administered intraperitoneally every 5 days for 5 doses. The study period will be 30 days post initiation of the dosing regimens.

Tumors on animals in Treatment Group A are anticipated to progress rapidly. The remaining groups are observed for tumor regression and number of CRs. It is anticipated that benzo[b]thiophene STING agonist in combination with anti PD-1 muDX400 treatment (Treatment Group D) will demonstrate superior efficacy to single agent treatment groups.

When the foregoing experiment was conducted with selected combinations as described herein, the combination treatment (Treatment Group D) resulted in significant antitumor efficacy compared to Treatment Group A.

Example 2: Clinical Study Evaluating a Benzo[b]Thiophene STING Agonist in Combination with an Anti-PD-1 Antibody in Treatment of Patients with Advanced/Metastatic Solid Tumors or Lymphomas A Phase I clinical study will be conducted to evaluate, in part, the effects of a combination therapy, consisting of administration of a pembrolizumab intravenous infusion and of a benzo[b]thiophene STING agonist as described above intratumoral injection, on advanced or metastatic solid tumors or lymphomas. The study is a non-randomized, 2-arm, multi-site, open-label trial of benzo[b]thiophene STING agonist monotherapy and benzo[b]thiophene STING agonist in combination with pembrolizumab in subjects with advanced/metastatic solid tumors or lymphomas. benzo[b]thiophene STING agonist will be administered intratumorally (IT).

Unless deemed medically unsafe by the Investigator, all subjects will be required to provide a sample of the tumor to be injected and a sample from a distant site prior to benzo [b]thiophene STING agonist administration during screening, as well as on Cycle 3, Day 15. Subjects with amenable lesions at both injected and non-injected sites may undergo an additional optional tumor biopsy on Cycle 6, Day 15 of both the injected lesion and the non-injected lesion. Subjects will undergo a 24-hour observation period following the first dose administration on Cycle 1, Day 1. Each cycle within the trial is a 21-day cycle. Dosing in the first 3 cycles is once a week (Q1W) and dosing in cycles 4 and beyond is once every 3 weeks (Q3W).

Dose escalation will proceed based on emerging safety and tolerability data of benzo[b]thiophene STING agonist as monotherapy and as combination therapy with pembrolizumab. For each dose level, an assessment will be made of the safety and tolerability data in order to define the next dose level to be tested. Both treatment arms will start with an accelerated titration design (ATD) followed by the modified toxicity probability interval (mTPI) method to identify a maximum tolerated dose (MTD) or maximum administered dose (MAD) of benzo[b]thiophene STING agonist alone (Arm 1) or benzo[b]thiophene STING agonist in combination with pembrolizumab (Arm 2). Starting with a dose of 10 µg of benzo[b]thiophene STING agonist in single patient cohorts (Arm 1, Part A), the trial will proceed in an ATD up to a dose that meets at least 1 of the following 3 criteria: 1) The 270 µg cohort is completed, 2) ≥Grade 2 non-disease-related toxicity at any dose level, or 3) Elevation of systemic TNF-α in blood above baseline levels by ≥3 fold increase for a given subject at any time during the first cycle of benzo[b]thiophene STING agonist. Upon completion of the ADT phase by reaching at least one of the above triggering criteria, the monotherapy arm (Arm 1) of the study will proceed to a dose escalation and confirmation phase (Part B), using an mTPI design. In addition, Arm 2 (Part C), the combination therapy arm, will initiate once 2 dose levels within Arm 1 have been cleared by dose-limiting toxicity (DLT) evaluation.

Starting with a dose that is at least 2 dose levels behind benzo[b]thiophene STING agonist monotherapy, benzo[b]thiophene STING agonist combination therapy with pembrolizumab (Arm 2 Part C) will begin in single patient cohorts. In Arm 2 Part C, benzo[b]thiophene STING agonist combination arm with pembrolizumab, dose escalation will proceed in an ATD up to a dose level which meets at least 1 of the following 3 criteria: 1) The 270 µg cohort in combination is completed, 2) ≥Grade 2 non-disease-related toxicity at any dose level in combination, or 3) Elevation of systemic TNF-α in blood above baseline levels by ≥3 fold for a given subject at any time during the first cycle of benzo[b]thiophene STING agonist in combination with pembrolizumab. Arm 2 will then proceed to mTPI (Arm 2, Part D) to determine the MTD/MAD of the combination of benzo[b]thiophene STING agonist and pembrolizumab.

Intra-subject dose escalation of benzo[b]thiophene STING agonist to the next dose level is permitted only in Arm 1, including Parts A and B. Intrasubject dose escalation will be at the discretion of the Investigator, provided that the subject remains on study after receiving 3 cycles of treatment without ≥Grade 2 toxicity, and provided that the dose escalation has proceeded beyond the next dose level. Intra-subject dose escalation is not permitted in Arm 2 (Parts C and D).

During benzo[b]thiophene STING agonist dose escalation in both Arm 1 (Parts A and (b) and Arm 2 (Parts C and D), at least 7 days of observation will occur between each of the first 2 subjects at each dose level. Over-enrollment in ATD up to 3 subjects per cohort is permitted, provided that the first 2 subjects will receive benzo[b]thiophene STING agonist treatment at least 7 days apart. Dose escalation of benzo[b]thiophene STING agonist to determine the MTD/MAD will be guided by the mTPI design, targeting a DLT rate of 30%. Doses of benzo[b]thiophene STING agonist used in combination with pembrolizumab will be at least 2 dose levels behind the monotherapy benzo[b]thiophene STING agonist dose, and will not exceed the MTD for monotherapy. If an MTD for the monotherapy arm is established, then the dose of benzo[b]thiophene STING agonist in combination may continue escalation up to that dose. For example, if the MTD for monotherapy (Arm 1, Part A) is 90 µg, then the starting dose for combination therapy (Arm 2, Part C), if no DLTs occurred in monotherapy, may be 10 µg, with a maximum dose escalation to 90 µg. If the MTD for monotherapy (Arm 1, Part A) is ≤30 µg, then the starting dose for combination therapy will be 10 µg. In monotherapy (Arm 1, Part A), if the 270 µg dose level is completed, then the starting dose in combination therapy (Arm 2, Part C) will be 90 µg.

A fixed dose of intravenous pembrolizumab 200 mg will be administered every 3 weeks in Arm 2. A minimum of 3 subjects are required at each dose level during mTPI in both Arm 1 and Arm 2. The mTPI phase will have up to 3 to 6 subjects per cohort, and based on the occurrence of DLTs, up to 14 subjects may enroll per dose level. Therefore, during mTPI, up to 14 subjects may be enrolled per dose level, depending on the occurrence of a dose-limiting toxicity (DLT). Subjects may continue on their assigned treatment for up to 35 cycles (approximately 2 years) from the start of treatment. Treatment may continue until one of the following occurs: disease progression, unacceptable adverse event(s), intercurrent illness that prevents further administration of treatment, Investigator decision to withdraw the subject, subject withdraws consent, pregnancy of the subject, noncompliance with trials treatment or procedure requirements, or administrative reasons requiring cessation of treatment.

Subjects who progress by either clinical or radiographic evaluation on monotherapy with benzo[b]thiophene STING agonist (Arm 1), may cross over into the combination arm of benzo[b]thiophene STING agonist and pembrolizumab (Arm 2), provided that they meet crossover eligibility criteria. Subjects who cross over from Arm 1 to Arm 2 are eligible for up to 35 cycles of treatment within Arm 2. Subjects who cross over will enter Arm 2 at the start of Arm 2.

Treatment allocation to Arm 1 will be accomplished by non-random assignment through an interactive voice response system/integrated web response system (IVRS/IWRS). When both treatment arms are open for enrollment, IVRS/IWRS will alternate subject assignment between Arm 1 and 2, starting with Arm 1. Establishment of the MTD/MAD in the combination therapy of benzo[b]thiophene STING agonist and pembrolizumab (Arm 2) requires that at least half of the subjects in Arm 2 have had no prior exposure to benzo[b]thiophene STING agonist (i.e. non-crossover subjects). New subjects who are benzo[b]thiophene STING agonist-naïve (non-crossover subjects) will be given priority for enrollment into Arm 2.

The final number of subjects enrolled in the dose escalation and confirmation parts of the study will depend on the empirical safety data (DLT observations, in particular, at which dose the mTPI design is triggered and at which dose the preliminary recommended Phase 2 dose is identified). For example, in a scenario where benzo[b]thiophene STING agonist monotherapy starts at 10 µg and continues to the highest dose, the sample size across Parts A and B may be approximately 40 subjects. For combination therapy of benzo[b]thiophene STING agonist with pembrolizumab, in a scenario where Arm 2 starts at 10 µg of benzo[b]thiophene STING agonist with 200 mg of pembrolizumab, and continues to the highest dose, the sample size across Parts C and D may be approximately 40 subjects. In this scenario, the total sample size across Parts A-D will be approximately 80 subjects. An administrative analysis may be conducted to enable future trial planning at the Sponsor's discretion, and data will be examined on a continuous basis to allow for dose escalation and confirmation decisions.

The trial will be conducted in conformance with Good Clinical Practices.

Adverse Experiences (AEs) will be evaluated according to criteria outlined in the National Cancer Institute (NCI) Common Terminology Criteria for Adverse Events (CT-CAE) v4.

It will be appreciated that various of the above-discussed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A method of treating cancer, said method comprising administering to a subject in need thereof a combination therapy that comprises a) a PD-1 antagonist; and b) a benzo[b]thiophene STING agonist; wherein the PD-1 antagonist is administered once every 21 days; and the benzo[b]thiophene STING agonist is administered once every 3 to 28 days; and the benzo[b]thiophene STING agonist is selected from the group consisting of:

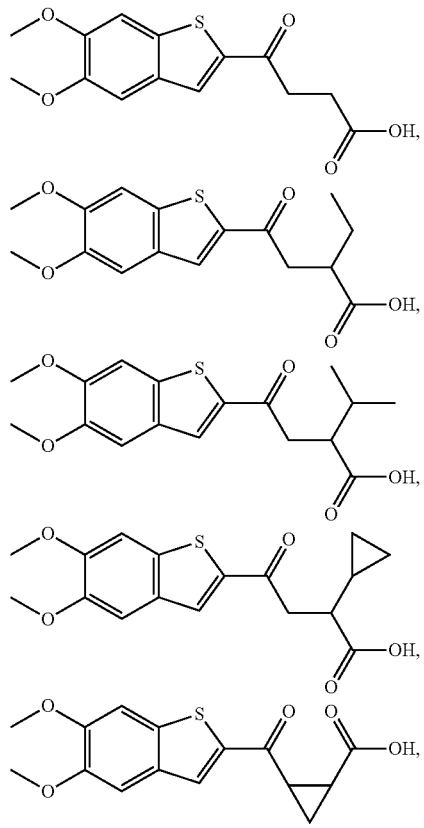

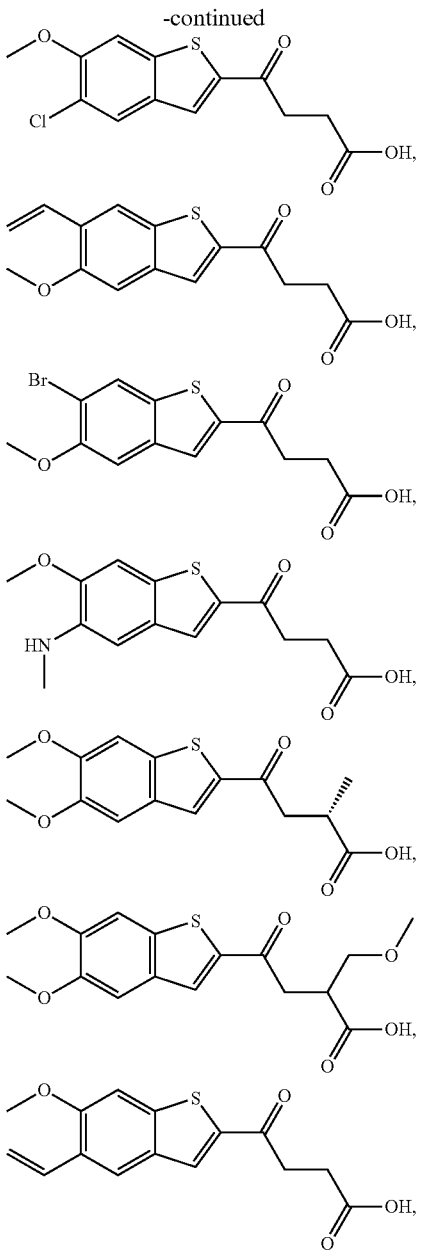

-continued

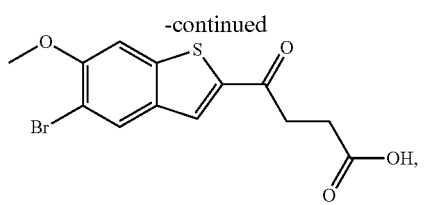

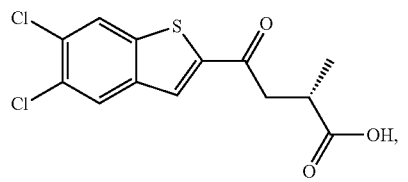

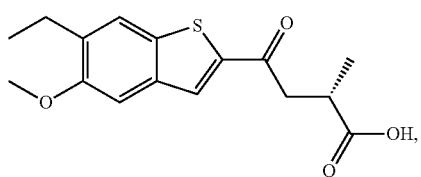

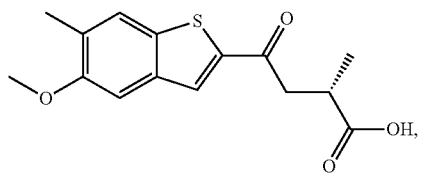

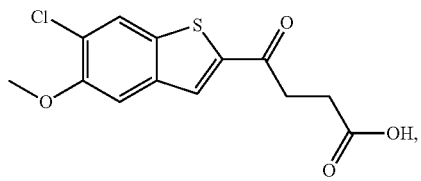

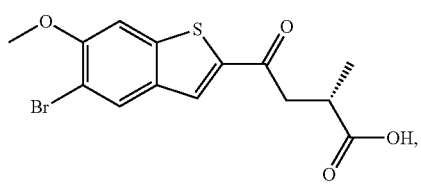

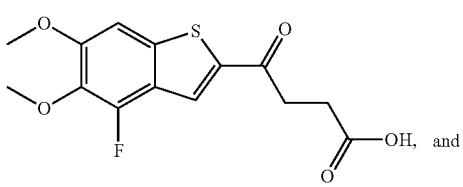

-continued

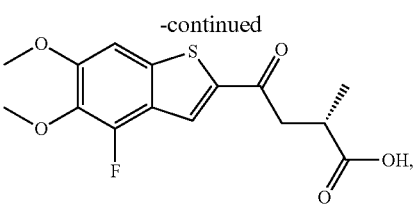

or a pharmaceutically acceptable salt thereof.

2. The method according to claim 1, wherein the cancer occurs as one or more solid tumors or lymphomas.

3. The method according to claim 1, wherein the cancer is selected from the group consisting of advanced or metastatic solid tumors and lymphomas.

4. The method according to claim 1, wherein the cancer is selected from the group consisting of malignant melanoma, head and neck squamous cell carcinoma, breast adenocarcinoma, and lymphoma.

5. The method according to claim 2, wherein the lymphoma is selected from the group consisting of diffuse large B-cell lymphoma, follicular lymphoma, mantle cell lymphoma, small lymphocytic lymphoma, mediastinal large B-cell lymphoma, splenic marginal zone B-cell lymphoma, extranodal marginal zone B-cell lymphoma of mucosa-associated lymphoid tissue (malt), nodal marginal zone B-cell lymphoma, lymphoplasmacytic lymphoma, primary effusion lymphoma, Burkitt lymphoma, anaplastic large cell lymphoma (primary cutaneous type), anaplastic large cell lymphoma (systemic type), peripheral T-cell lymphoma, angioimmunoblastic T-cell lymphoma, adult T-cell lymphoma, nasal type extranodal NK/T-cell lymphoma, enteropathy-associated T-cell lymphoma, gamma/delta hepatosplenic T-cell lymphoma, subcutaneous panniculitis-like T-cell lymphoma, mycosis fungoides, and Hodgkin lymphoma.

6. The method according to claim 1, wherein the cancer has metastasized.

7. The method according to claim 1, wherein the PD-1 antagonist is an anti-PD-1 monoclonal antibody.

8. The method according to claim 7, wherein the PD-1 antagonist is selected from the group consisting of nivolumab, pembrolizumab, pidilizumab, and AMP-224.

9. The method according to claim 8, wherein the PD-1 antagonist is nivolumab.

10. The method according to claim 8, wherein the PD-1 antagonist is pembrolizumab.

11. The method of claim 1, wherein the PD-1 antagonist is administered by intravenous infusion, and the benzo[b]thiophene STING agonist is administered orally, by intravenous infusion, by intertumoral injection or by subcutaneous injection.

\* \* \* \* \*

SEQUENCE LISTING

<160> NUMBER OF SEQ ID NOS: 21

<210> SEQ ID NO 1
<211> LENGTH: 111
<212> TYPE: PRT
<213> ORGANISM: Artificial
<220> FEATURE:
<223> OTHER INFORMATION: Pembrolizumab: variable light chain, amino acid

<400> SEQUENCE: 1

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
                20                  25                  30

Gly Tyr Ser Tyr Leu His Trp Tyr Gln Gln Lys Pro Gly Gln Ala Pro
            35                  40                  45

Arg Leu Leu Ile Tyr Leu Ala Ser Tyr Leu Glu Ser Gly Val Pro Ala
        50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys
            100                 105                 110
```

<210> SEQ ID NO 2
<211> LENGTH: 120
<212> TYPE: PRT
<213> ORGANISM: Artificial
<220> FEATURE:
<223> OTHER INFORMATION: Pembrolizumab: variable heavy chain, amino acid

<400> SEQUENCE: 2

```
Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Tyr Met Tyr Trp Val Arg Gln Ala Pro Gly Gln Gly Leu Glu Trp Met
            35                  40                  45

Gly Gly Ile Asn Pro Ser Asn Gly Gly Thr Asn Phe Asn Glu Lys Phe
        50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser
        115                 120
```

<210> SEQ ID NO 3
<211> LENGTH: 218
<212> TYPE: PRT
<213> ORGANISM: Artificial
<220> FEATURE:
<223> OTHER INFORMATION: Pembrolizumab: light chain, amino acid

<400> SEQUENCE: 3

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 4
<211> LENGTH: 447
<212> TYPE: PRT
<213> ORGANISM: Artificial
<220> FEATURE:
<223> OTHER INFORMATION: Pembrolizumab: heavy chain, amino acid

<400> SEQUENCE: 4

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

-continued

```
Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 5
<211> LENGTH: 15
<212> TYPE: PRT
<213> ORGANISM: Artificial
<220> FEATURE:
<223> OTHER INFORMATION: Pembrolizumab: CDRL1

<400> SEQUENCE: 5

Arg Ala Ser Lys Gly Val Ser Thr Ser Gly Tyr Ser Tyr Leu His
1               5                   10                  15

<210> SEQ ID NO 6
<211> LENGTH: 7
<212> TYPE: PRT
<213> ORGANISM: Artificial
<220> FEATURE:
```

<223> OTHER INFORMATION: Pembrolizumab: CDRL2

<400> SEQUENCE: 6

Leu Ala Ser Tyr Leu Glu Ser
1               5

<210> SEQ ID NO 7
<211> LENGTH: 9
<212> TYPE: PRT
<213> ORGANISM: Artificial
<220> FEATURE:
<223> OTHER INFORMATION: Pembrolizumab: CDRL3

<400> SEQUENCE: 7

Gln His Ser Arg Asp Leu Pro Leu Thr
1               5

<210> SEQ ID NO 8
<211> LENGTH: 5
<212> TYPE: PRT
<213> ORGANISM: Artificial
<220> FEATURE:
<223> OTHER INFORMATION: Pembrolizumab: CDRH1

<400> SEQUENCE: 8

Asn Tyr Tyr Met Tyr
1               5

<210> SEQ ID NO 9
<211> LENGTH: 16
<212> TYPE: PRT
<213> ORGANISM: Artificial
<220> FEATURE:
<223> OTHER INFORMATION: Pembrolizumab: CDRH2

<400> SEQUENCE: 9

Gly Ile Asn Pro Ser Asn Gly Gly Thr Asn Phe Asn Glu Lys Phe Lys
1               5                   10                  15

<210> SEQ ID NO 10
<211> LENGTH: 11
<212> TYPE: PRT
<213> ORGANISM: Artificial
<220> FEATURE:
<223> OTHER INFORMATION: Pembrolizumab: CDRH3

<400> SEQUENCE: 10

Arg Asp Tyr Arg Phe Asp Met Gly Phe Asp Tyr
1               5                   10

<210> SEQ ID NO 11
<211> LENGTH: 107
<212> TYPE: PRT
<213> ORGANISM: Artificial
<220> FEATURE:
<223> OTHER INFORMATION: Nivolumab: variable light chain, amino acid

<400> SEQUENCE: 11

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly

```
                   50                   55                   60
Ser Gly Ser Gly Thr Asp Phe Thr Leu Thr Ile Ser Ser Leu Glu Pro
 65                  70                   75                   80

Glu Asp Phe Ala Val Tyr Tyr Cys Gln Gln Ser Ser Asn Trp Pro Arg
                 85                   90                   95

Thr Phe Gly Gln Gly Thr Lys Val Glu Ile Lys
                100                  105
```

<210> SEQ ID NO 12
<211> LENGTH: 113
<212> TYPE: PRT
<213> ORGANISM: Artificial
<220> FEATURE:
<223> OTHER INFORMATION: Nivolumab: variable heavy chain, amino acid

<400> SEQUENCE: 12

```
Gln Val Gln Leu Val Glu Ser Gly Gly Gly Val Val Gln Pro Gly Arg
 1               5                   10                  15

Ser Leu Arg Leu Asp Cys Lys Ala Ser Gly Ile Thr Phe Ser Asn Ser
                20                  25                  30

Gly Met His Trp Val Arg Gln Ala Pro Gly Lys Gly Leu Glu Trp Val
            35                  40                  45

Ala Val Ile Trp Tyr Asp Gly Ser Lys Arg Tyr Tyr Ala Asp Ser Val
        50                  55                  60

Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Tyr Cys
                 85                  90                  95

Ala Thr Asn Asp Asp Tyr Trp Gly Gln Gly Thr Leu Val Thr Val Ser
            100                 105                 110

Ser
```

<210> SEQ ID NO 13
<211> LENGTH: 214
<212> TYPE: PRT
<213> ORGANISM: Artificial
<220> FEATURE:
<223> OTHER INFORMATION: Nivolumab: light chain, amino acid

<400> SEQUENCE: 13

```
Glu Ile Val Leu Thr Gln Ser Pro Ala Thr Leu Ser Leu Ser Pro Gly
 1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ser Ser Asn Trp Pro Arg
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
```

```
                130              135              140
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
                210

<210> SEQ ID NO 14
<211> LENGTH: 440
<212> TYPE: PRT
<213> ORGANISM: Artificial
<220> FEATURE:
<223> OTHER INFORMATION: Nivolumab: heavy chain, amino acid

<400> SEQUENCE: 14

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
                20                  25                  30

Gly Met His Trp Val Arg Gln Ala Pro Gly Lys Gly Leu Glu Trp Val
                35                  40                  45

Ala Val Ile Trp Tyr Asp Gly Ser Lys Arg Tyr Tyr Ala Asp Ser Val
50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
                100                 105                 110

Ser Ala Ser Thr Lys Gly Pro Ser Val Phe Pro Leu Ala Pro Cys Ser
                115                 120                 125

Arg Ser Thr Ser Glu Ser Thr Ala Ala Leu Gly Cys Leu Val Lys Asp
                130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
                180                 185                 190

Thr Tyr Thr Cys Asn Val Asp His Lys Pro Ser Asn Thr Lys Val Asp
                195                 200                 205

Lys Arg Val Glu Ser Lys Tyr Gly Pro Pro Cys Pro Pro Cys Pro Ala
                210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
                260                 265                 270

Asp Gly Val Glu Val His Asn Ala Lys Thr Lys Pro Arg Glu Glu Gln
```

```
                    275                 280                 285
Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 15
<211> LENGTH: 11
<212> TYPE: PRT
<213> ORGANISM: Artificial
<220> FEATURE:
<223> OTHER INFORMATION: Nivolumab: CDRL1

<400> SEQUENCE: 15

Arg Ala Ser Gln Ser Val Ser Ser Tyr Leu Ala
1               5                   10

<210> SEQ ID NO 16
<211> LENGTH: 7
<212> TYPE: PRT
<213> ORGANISM: Artificial
<220> FEATURE:
<223> OTHER INFORMATION: Nivolumab: CDRL2

<400> SEQUENCE: 16

Asp Ala Ser Asn Arg Ala Thr
1               5

<210> SEQ ID NO 17
<211> LENGTH: 9
<212> TYPE: PRT
<213> ORGANISM: Artificial
<220> FEATURE:
<223> OTHER INFORMATION: Nivolumab: CDRL3

<400> SEQUENCE: 17

Gln Gln Ser Ser Asn Trp Pro Arg Thr
1               5

<210> SEQ ID NO 18
<211> LENGTH: 5
<212> TYPE: PRT
<213> ORGANISM: Artificial
<220> FEATURE:
<223> OTHER INFORMATION: Nivolumab: CDRH1
```

```
<400> SEQUENCE: 18

Asn Ser Gly Met His
1               5

<210> SEQ ID NO 19
<211> LENGTH: 17
<212> TYPE: PRT
<213> ORGANISM: Artificial
<220> FEATURE:
<223> OTHER INFORMATION: Nivolumab: CDRH2

<400> SEQUENCE: 19

Val Ile Trp Tyr Asp Gly Ser Lys Arg Tyr Tyr Ala Asp Ser Val Lys
1               5                   10                  15

Gly

<210> SEQ ID NO 20
<211> LENGTH: 4
<212> TYPE: PRT
<213> ORGANISM: Artificial
<220> FEATURE:
<223> OTHER INFORMATION: Nivolumab: CDRH3

<400> SEQUENCE: 20

Asn Asp Asp Tyr
1

<210> SEQ ID NO 21
<211> LENGTH: 290
<212> TYPE: PRT
<213> ORGANISM: Homo sapiens

<400> SEQUENCE: 21

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205
```

```
Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
                260                 265                 270

Gly Ile Gln Asp Thr Asn Ser Lys Lys Gln Ser Asp Thr His Leu Glu
                275                 280                 285

Glu Thr
    290
```